US009364198B2

(12) United States Patent
Kumazawa

(10) Patent No.: US 9,364,198 B2
(45) Date of Patent: Jun. 14, 2016

(54) ULTRASOUND PROBE DIAGNOSING APPARATUS, ULTRASOUND DIAGNOSTIC APPARATUS, AND ULTRASOUND PROBE DIAGNOSING METHOD

(75) Inventor: Takashi Kumazawa, Otawara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 146 days.

(21) Appl. No.: 13/184,092

(22) Filed: Jul. 15, 2011

(65) Prior Publication Data
US 2011/0271762 A1 Nov. 10, 2011

Related U.S. Application Data

(62) Division of application No. 11/213,700, filed on Aug. 30, 2005.

(30) Foreign Application Priority Data

| Aug. 31, 2004 | (JP) | 2004-252973 |
| Aug. 31, 2004 | (JP) | 2004-252974 |
| Aug. 31, 2004 | (JP) | 2004-252975 |
| Aug. 31, 2004 | (JP) | 2004-252976 |
| Aug. 31, 2004 | (JP) | 2004-252977 |
| Sep. 14, 2004 | (JP) | 2004-267216 |
| Sep. 22, 2004 | (JP) | 2004-275982 |

(51) Int. Cl.
G01N 29/24 (2006.01)
A61B 8/00 (2006.01)
(Continued)

(52) U.S. Cl.
CPC . *A61B 8/587* (2013.01); *A61B 8/58* (2013.01); *G01S 7/5205* (2013.01);
(Continued)

(58) Field of Classification Search
USPC .......... 600/459, 446, 437, 407, 409, 443; 73/610, 1.82, 1.86; 310/322, 334, 365; 324/727; 702/117
See application file for complete search history.

(56) References Cited

U.S. PATENT DOCUMENTS 4,237,902 A * 12/1980 Okazaki .................. 600/444
4,241,608 A 12/1980 Dees et al.
(Continued)

FOREIGN PATENT DOCUMENTS

| EP | 0 426 276 A2 | 5/1991 |
| EP | 0 713 102 A1 | 5/1996 |

(Continued)

OTHER PUBLICATIONS

Japanese Office Action issued Jan. 25, 2011, in Patent Application No. 2005-250919 (with English-language translation).
(Continued)

*Primary Examiner* — Long V Le
*Assistant Examiner* — Katherine McDonald
(74) *Attorney, Agent, or Firm* — Oblon, McClelland, Maier & Neustadt, L.L.P

(57) ABSTRACT

An ultrasound probe diagnosing apparatus which diagnoses an ultrasound probe having an array of a plurality of ultrasound transducing elements on the basis of how the ultrasound probe receives reflected ultrasound waves from a test object placed to face the ultrasound probe, includes a part which detects a posture of the ultrasound probe with respect to the test object by comparing reflected ultrasound signals received by at least some of the plurality of ultrasound transducing elements, and a presenting part which presents information based on the detected posture.

3 Claims, 34 Drawing Sheets

(51) Int. Cl.
*G01S 7/52* (2006.01)
*G01S 15/89* (2006.01)

(52) U.S. Cl.
CPC .............. *G01S 7/52052* (2013.01); *A61B 8/00* (2013.01); *A61B 8/4245* (2013.01); *A61B 8/4438* (2013.01); *A61B 8/463* (2013.01); *G01S 15/8915* (2013.01)

(56) References Cited

U.S. PATENT DOCUMENTS

| | | | |
|---|---|---|---|
| 4,390,025 | A | 6/1983 | Takemura et al. |
| 4,630,612 | A | 12/1986 | Uchida et al. |
| 4,791,915 | A | 12/1988 | Barsotti et al. |
| 5,230,339 | A | 7/1993 | Charlebois |
| 5,276,654 | A * | 1/1994 | Mallart et al. .................. 367/7 |
| 5,517,994 | A | 5/1996 | Burke et al. |
| 5,538,004 | A | 7/1996 | Bamber |
| 5,660,179 | A | 8/1997 | Matsumoto et al. |
| 5,993,391 | A | 11/1999 | Kamiyama |
| 2002/0134133 | A1 | 9/2002 | Ogawa |
| 2004/0019270 | A1 | 1/2004 | Takeuchi |
| 2004/0211239 | A1 | 10/2004 | Gessert et al. |
| 2004/0211240 | A1 | 10/2004 | Gessert et al. |
| 2004/0213417 | A1 | 10/2004 | Gessert et al. |
| 2004/0230116 | A1 * | 11/2004 | Cowan et al. ................. 600/437 |
| 2004/0258127 | A1 * | 12/2004 | Ramamurthy et al. ....... 374/117 |
| 2005/0090742 | A1 | 4/2005 | Mine et al. |

FOREIGN PATENT DOCUMENTS

| | | |
|---|---|---|
| JP | 57-156749 | 9/1982 |
| JP | 60-29140 | 2/1985 |
| JP | 61-123981 | 6/1986 |
| JP | 5-48906 | 2/1993 |
| JP | 5-49642 | 3/1993 |
| JP | 5-115476 | 5/1993 |
| JP | 5-188138 | 7/1993 |
| JP | 8-238243 | 9/1996 |
| JP | 9-84785 | 3/1997 |
| JP | 9-182749 | 7/1997 |
| JP | 9-313488 | 12/1997 |
| JP | 10-227772 | 8/1998 |
| JP | 11-160293 | 6/1999 |
| JP | 2001-237497 | 8/2001 |
| JP | 2002-159492 | 6/2002 |
| JP | 2002-174592 | 6/2002 |
| JP | 2002-243654 | 8/2002 |
| JP | 2002-248101 | 9/2002 |
| JP | 2002-306478 | 10/2002 |
| JP | 2003-144432 | 5/2003 |
| JP | 2003-210458 | 7/2003 |
| JP | 2003-290224 | 10/2003 |
| JP | 2004-144685 | 5/2004 |
| JP | 2004-174227 | 6/2004 |
| WO | WO 92/21982 | 12/1992 |
| WO | WO 98/26281 | 6/1998 |
| WO | WO 99/33394 | 7/1999 |
| WO | WO 02/069807 A1 | 9/2002 |

OTHER PUBLICATIONS

Japanese Office Action issued Jan. 25, 2011, in Patent Application No. 2005-250923 (with English-language translation).
Japanese Office Action issued Jan. 25, 2011, in Patent Application No. 2005-250925 (with English-language translation).
Japanese Office Action issued Jan. 18, 2011, in Patent Application No. 2005-250922 (with English-language translation).

* cited by examiner

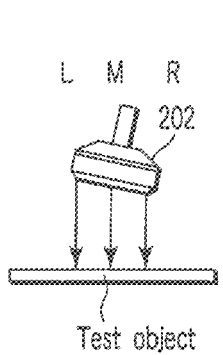
FIG. 4
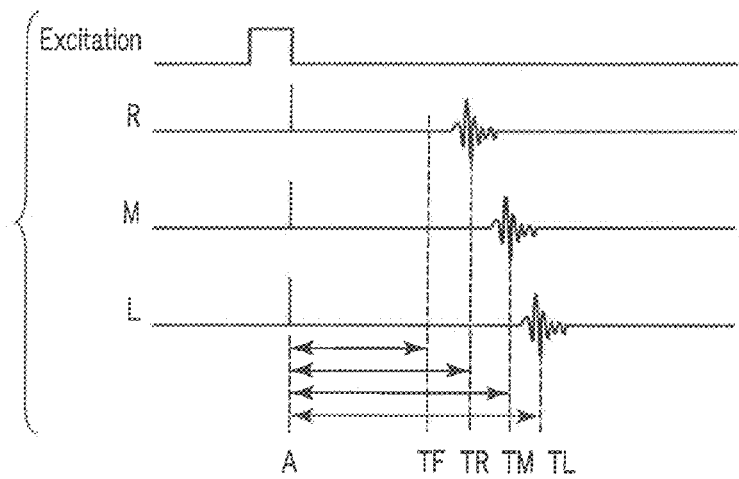
FIG. 5
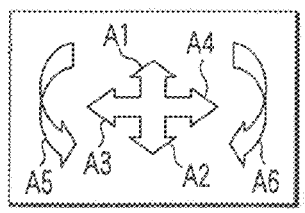
FIG. 6A
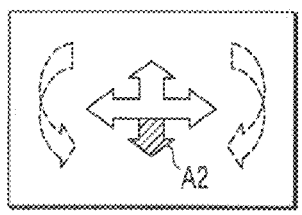   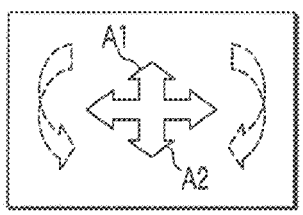   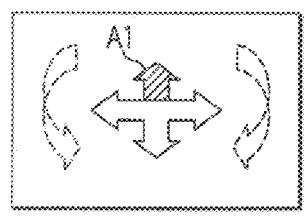
FIG. 6B    FIG. 6C    FIG. 6D
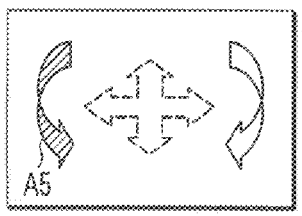   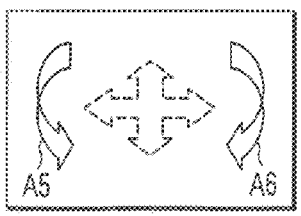   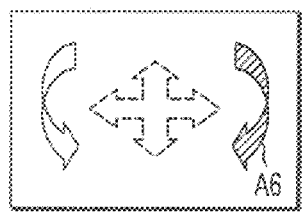
FIG. 6E    FIG. 6F    FIG. 6G

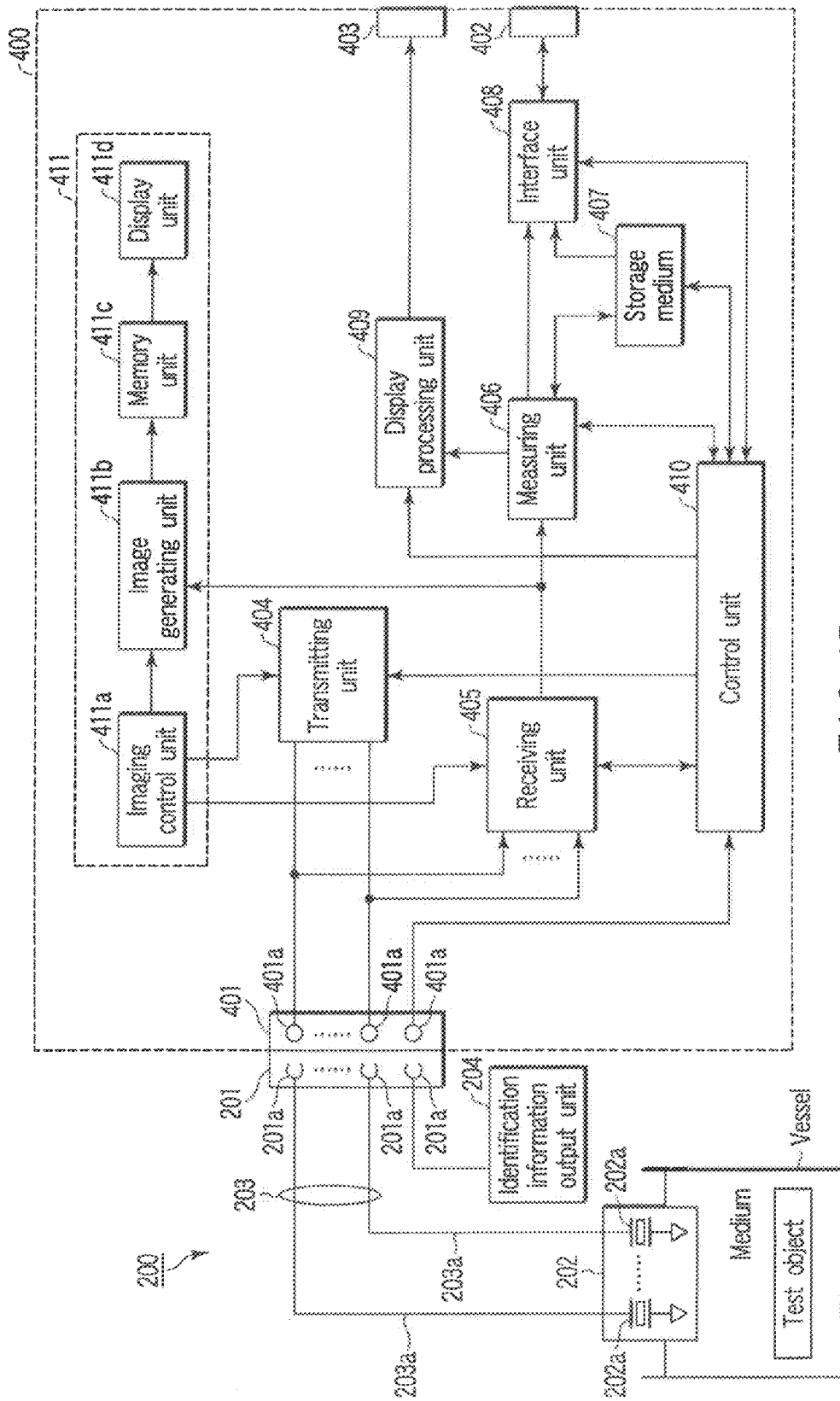
F I G. 15

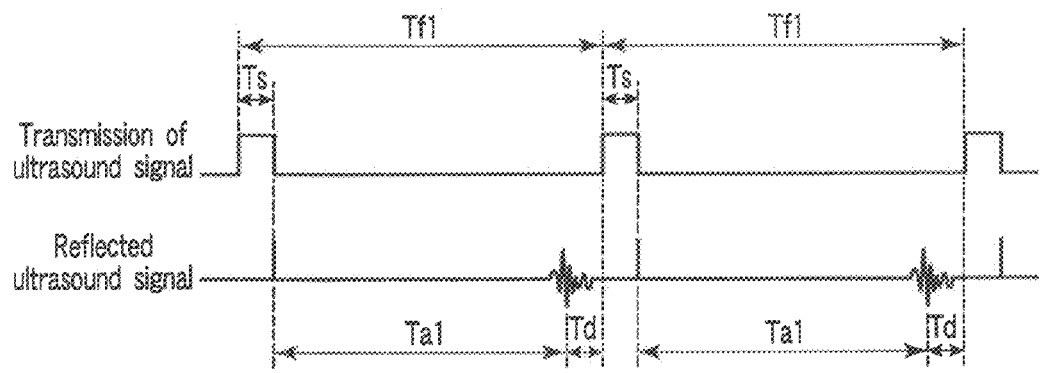
F I G. 16A
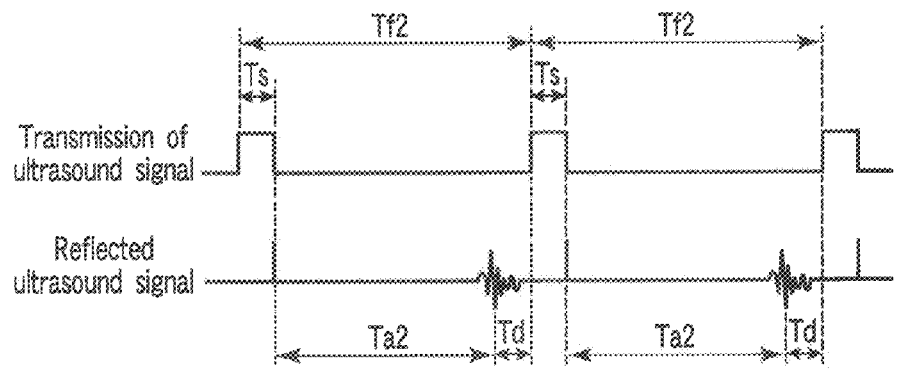
F I G. 16B

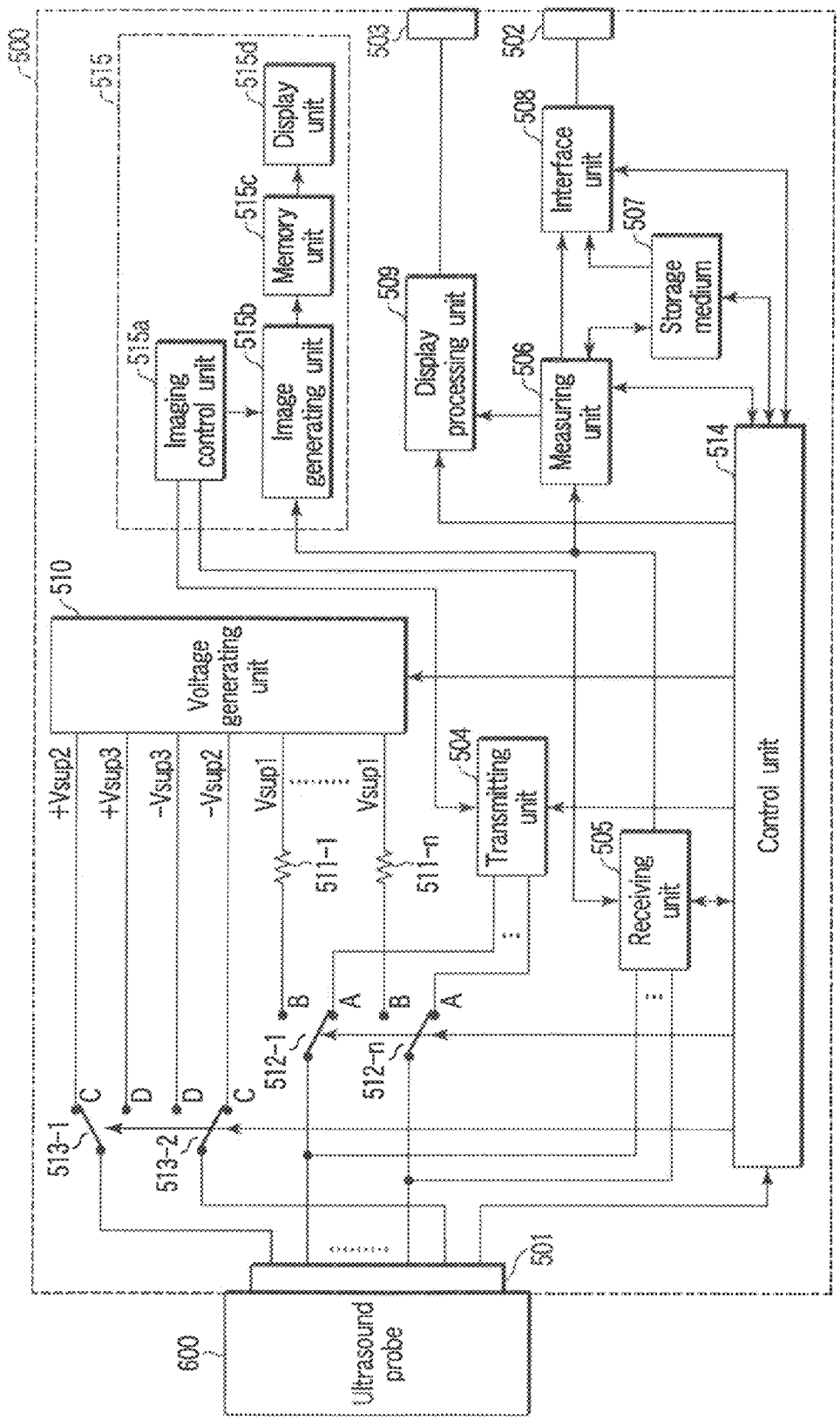
F I G. 19

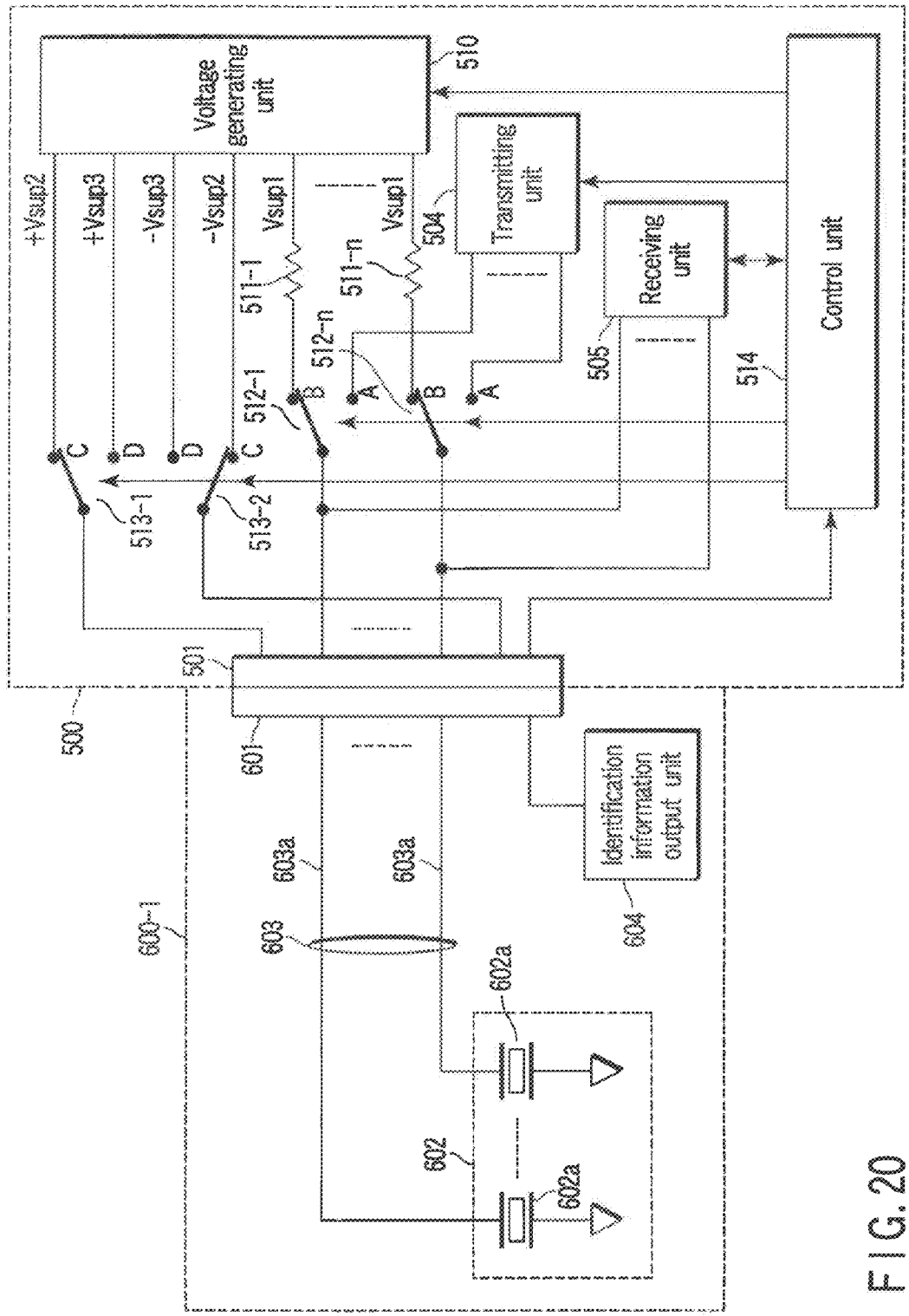
F I G. 20

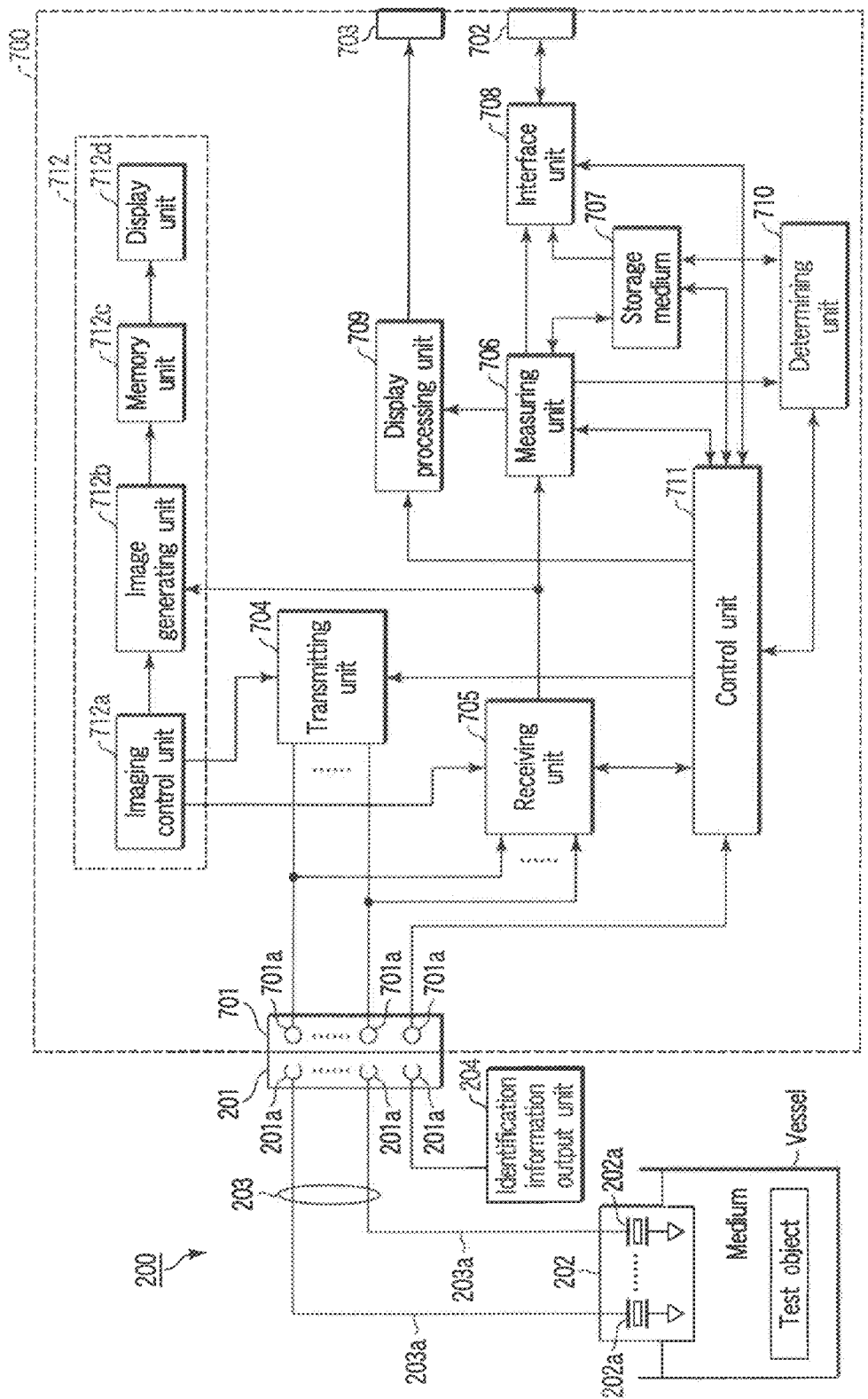
F I G. 24

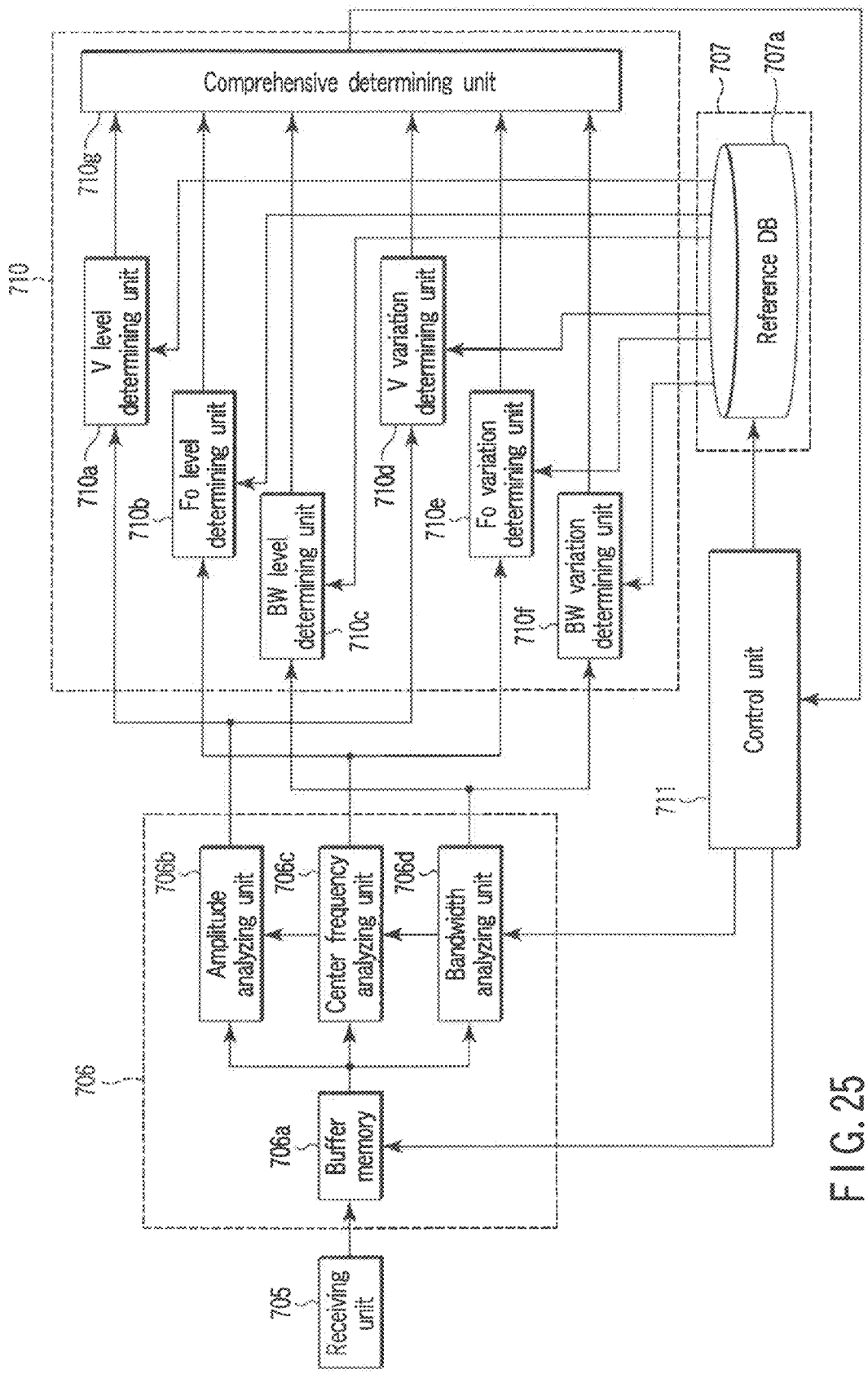
F I G. 25

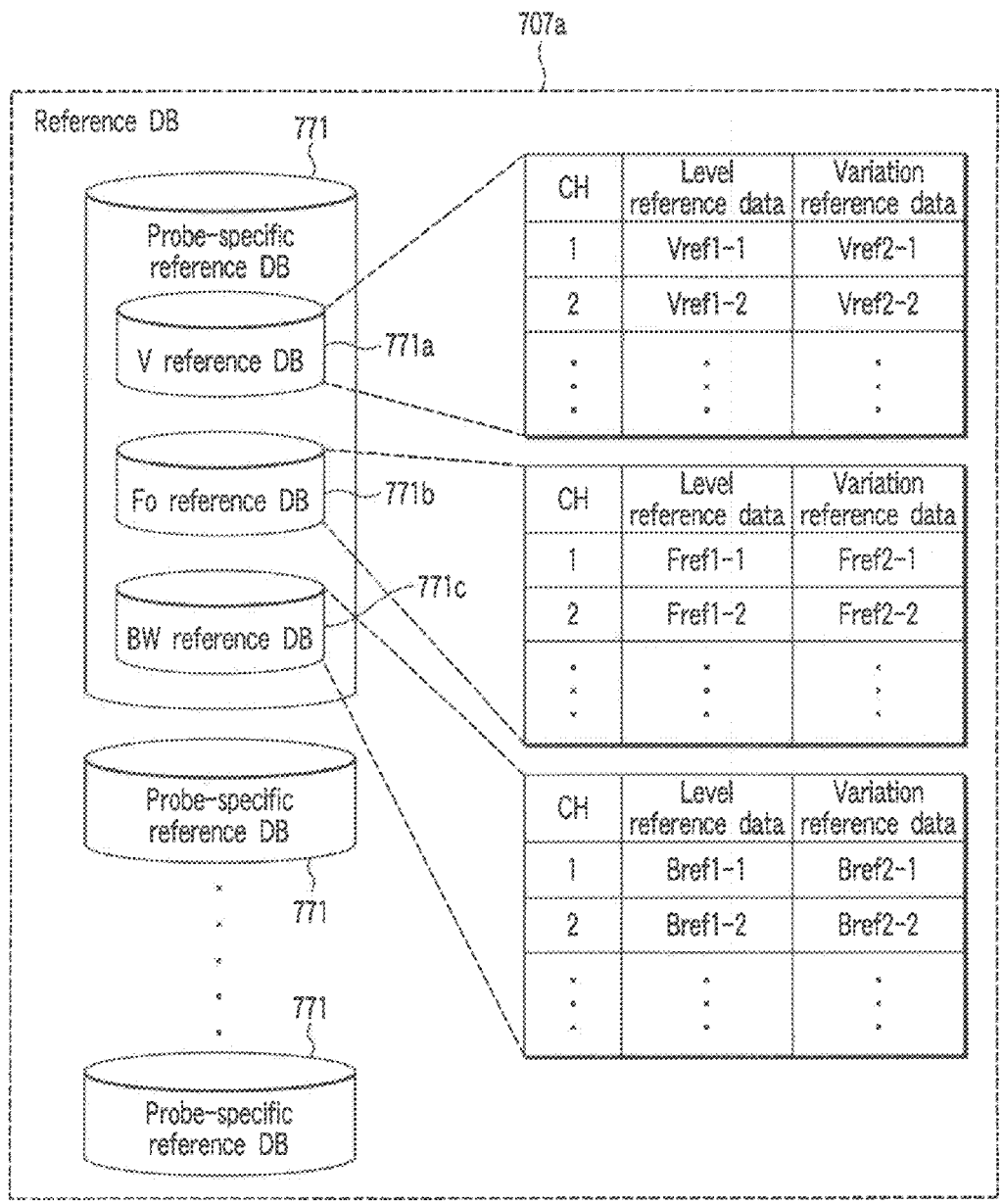
F I G. 26

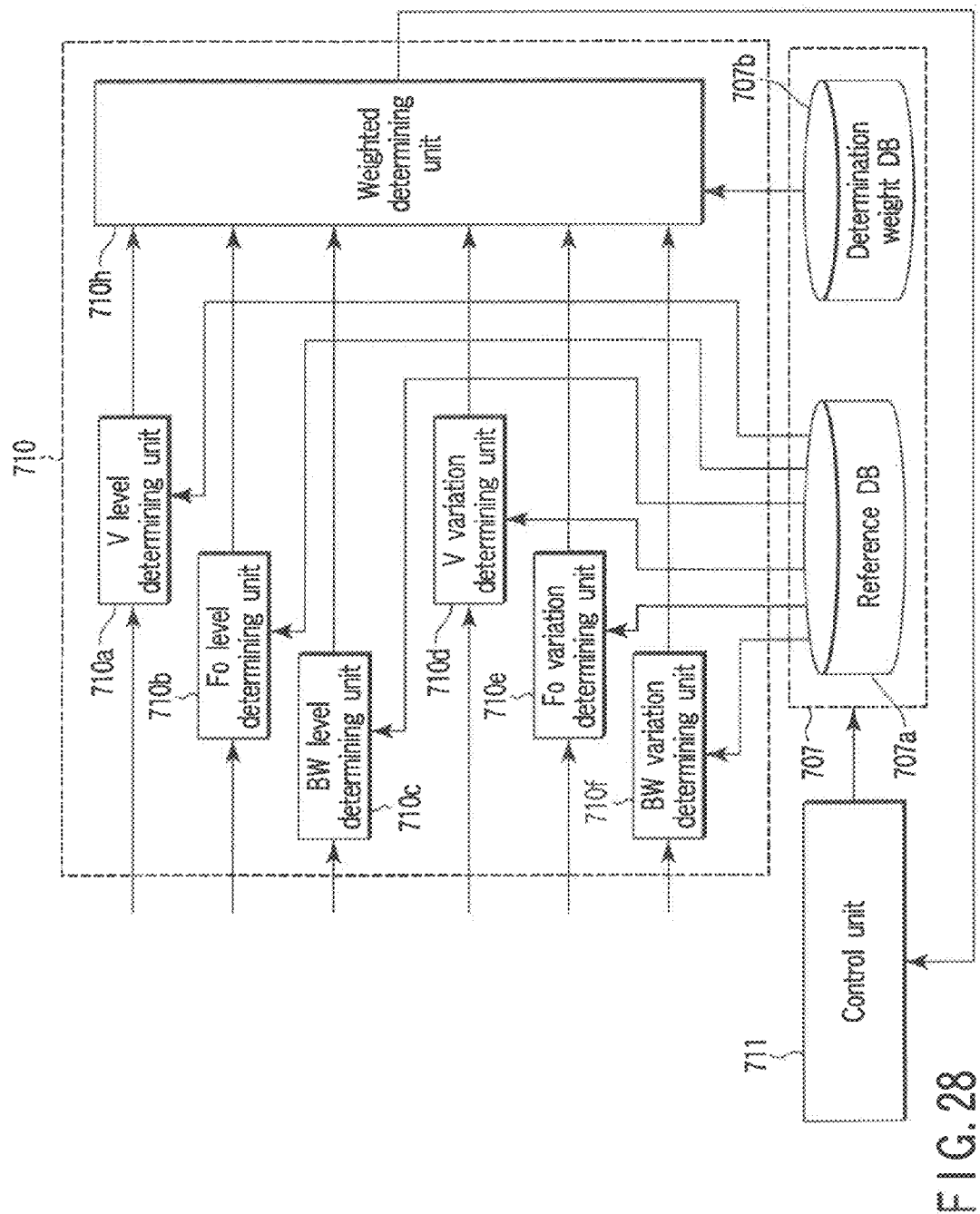
F I G. 28

| Outside reference | Inside reference (Pass) | | | | |
|---|---|---|---|---|---|
| Fail | 1 | 2 | 3 | 4 | 5 |

FIG. 32

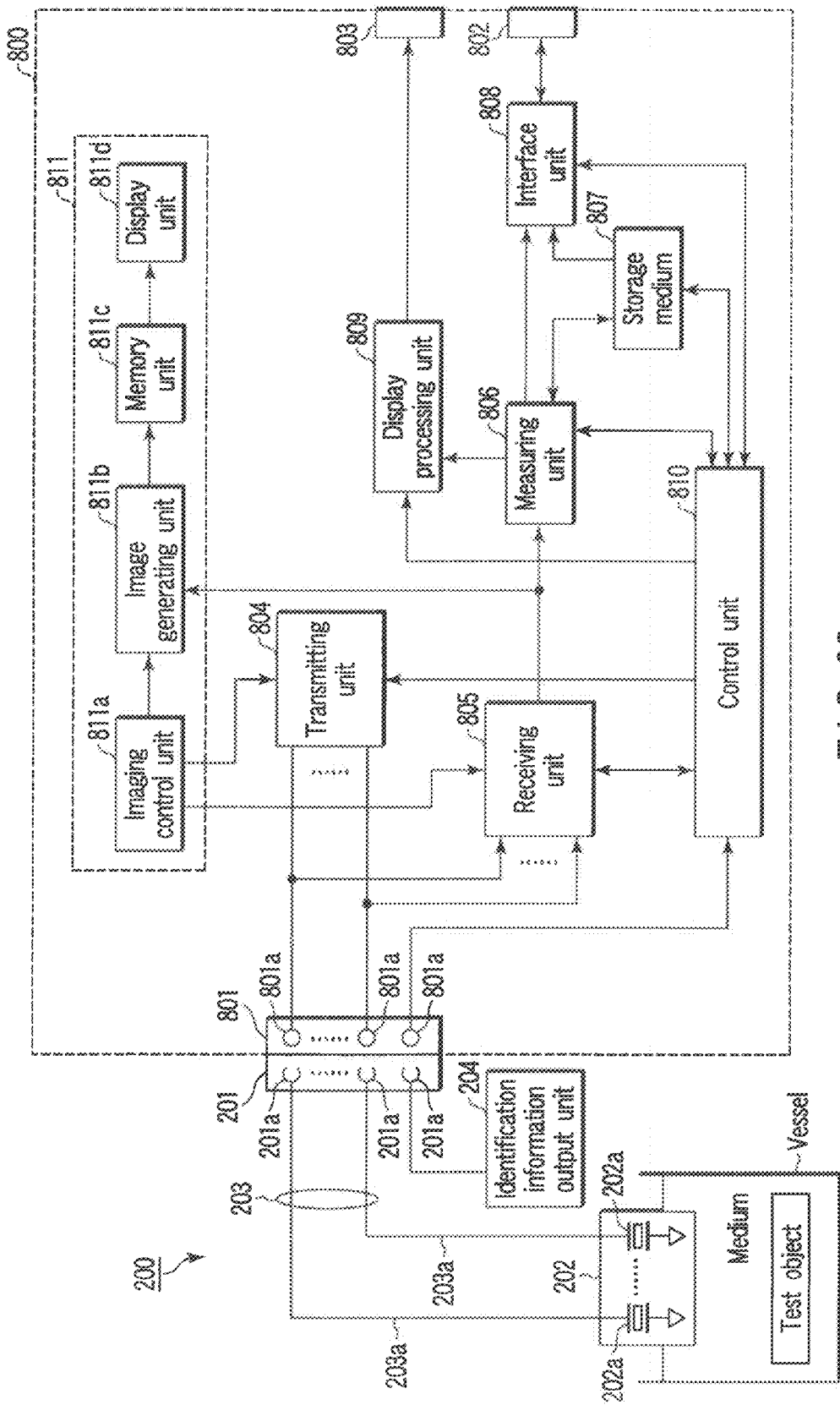
F I G. 33

FIG. 34

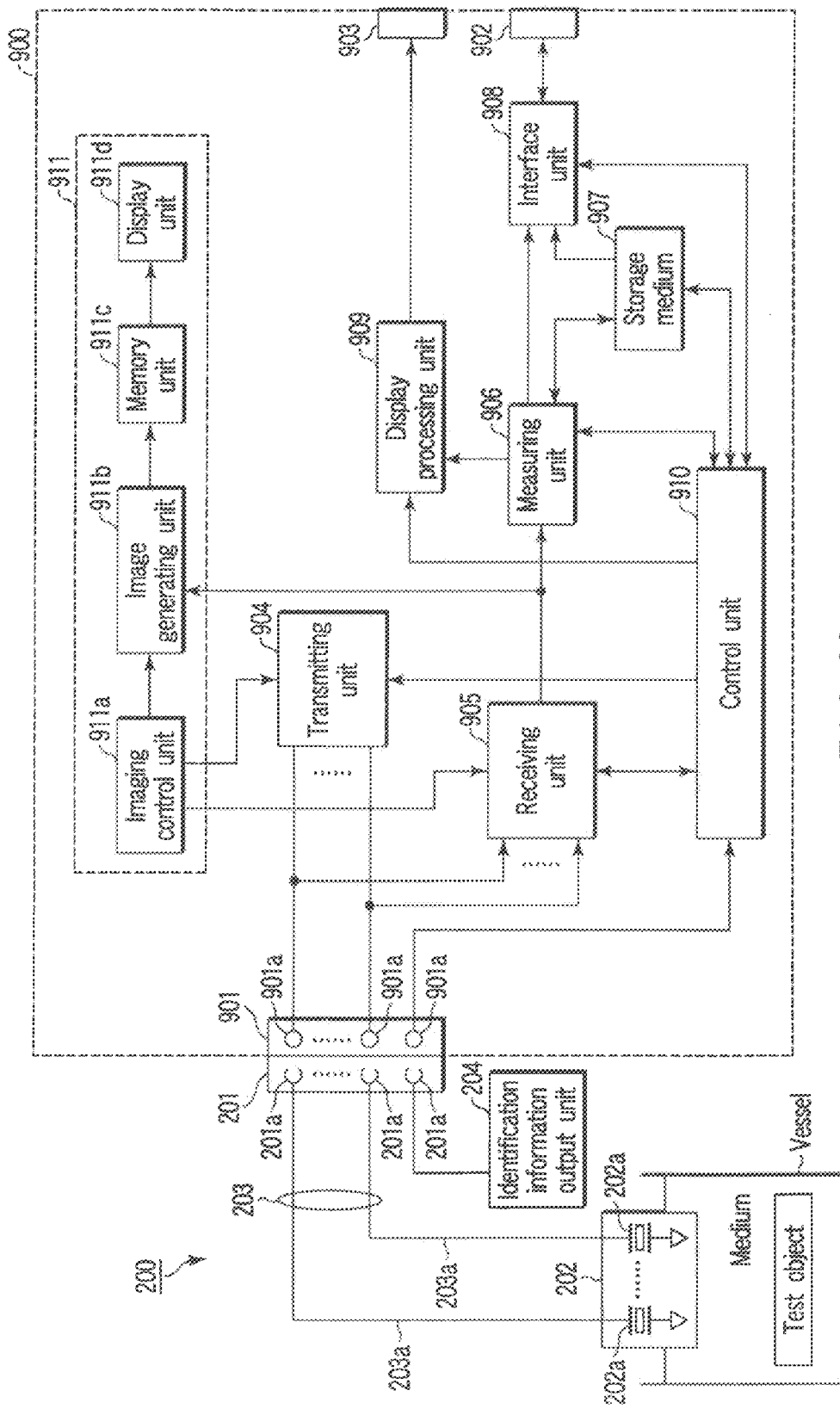
F I G. 36

| CH | Connector location | Determination | Signal cable | Head |
|---|---|---|---|---|
| 1 | A-12 | PASS | PASS | PASS |
| 2 | A-15 | PASS | PASS | PASS |
| 3 | A-17 | PASS | PASS | PASS |
| 4 | B-12 | PASS | PASS | PASS |

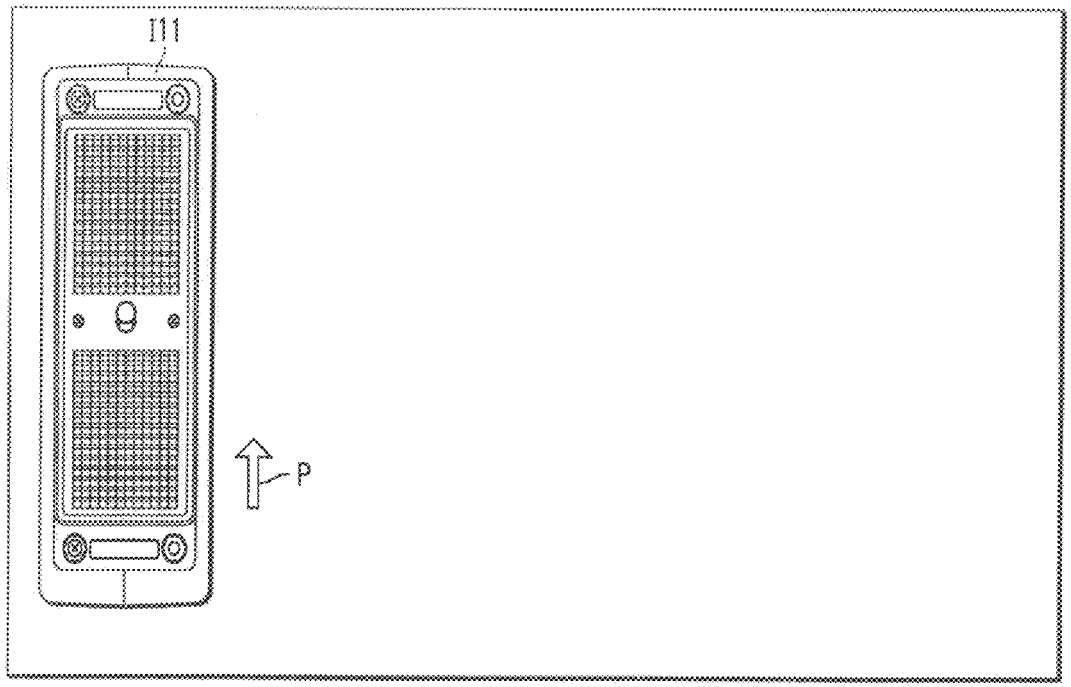
F I G. 40A
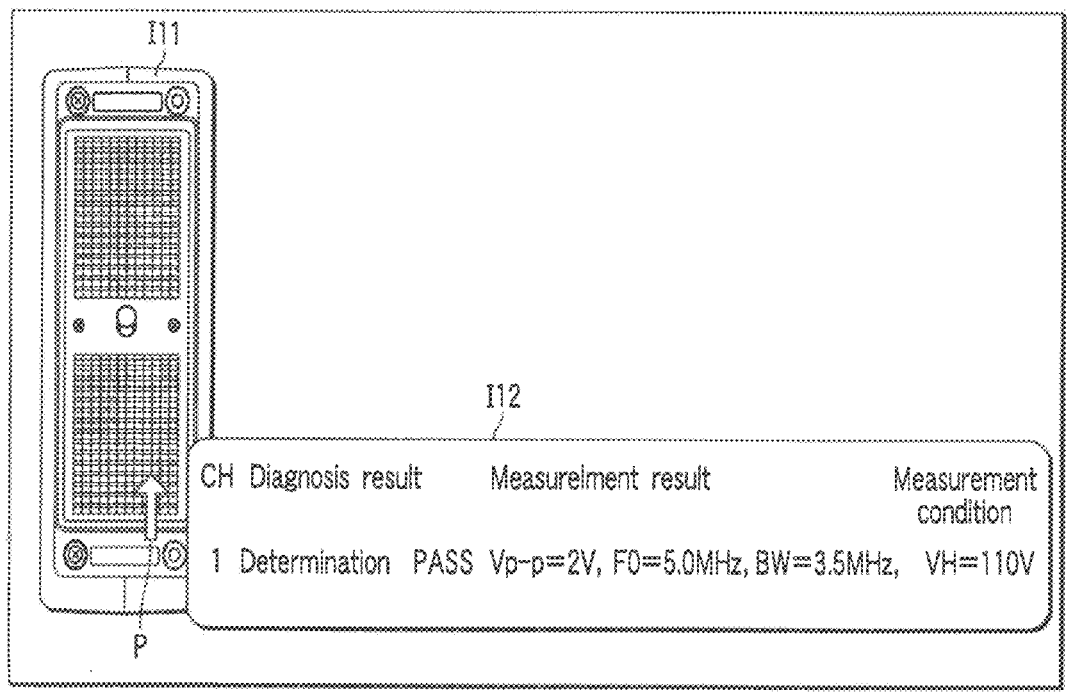
F I G. 40B

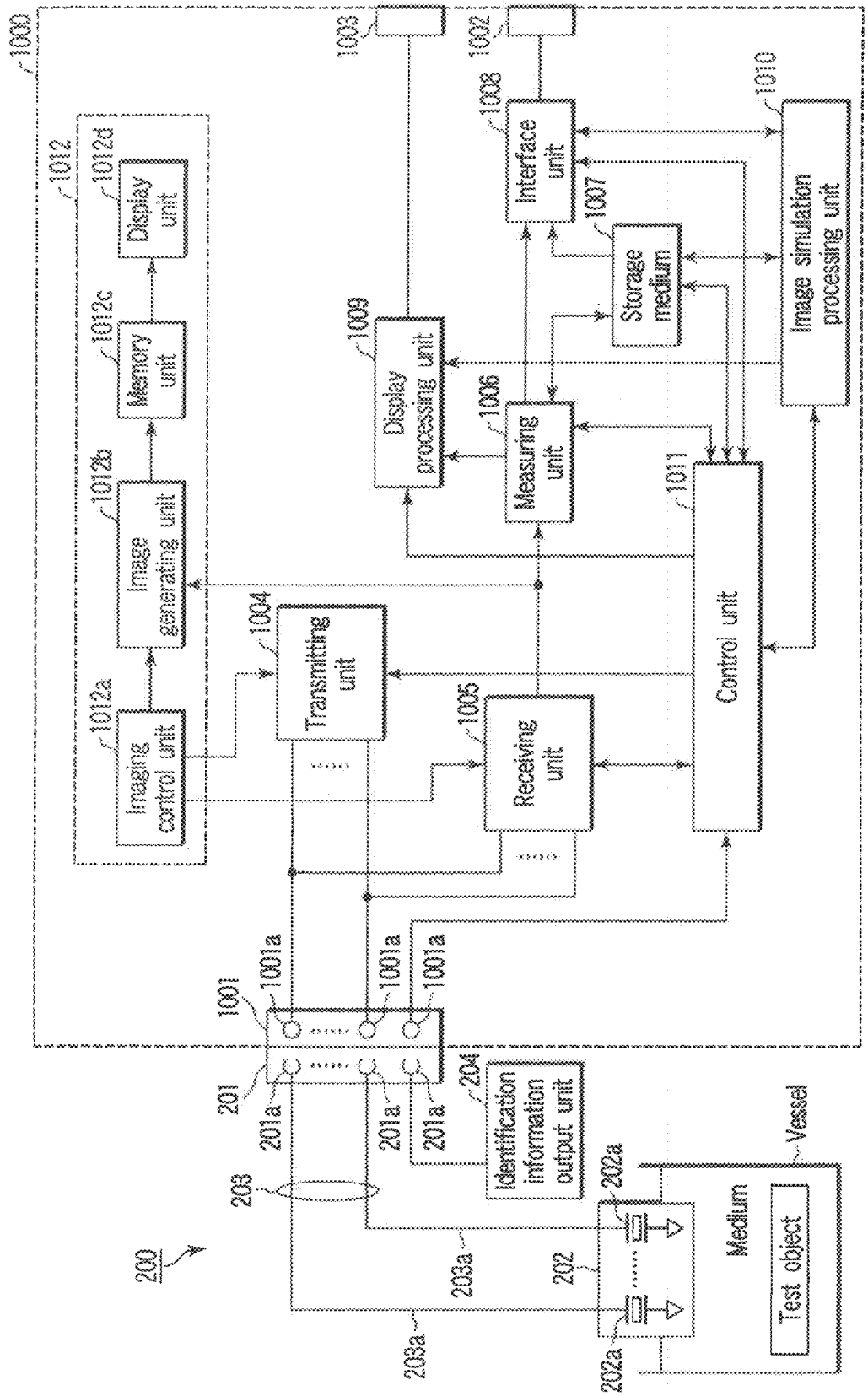
F I G. 41

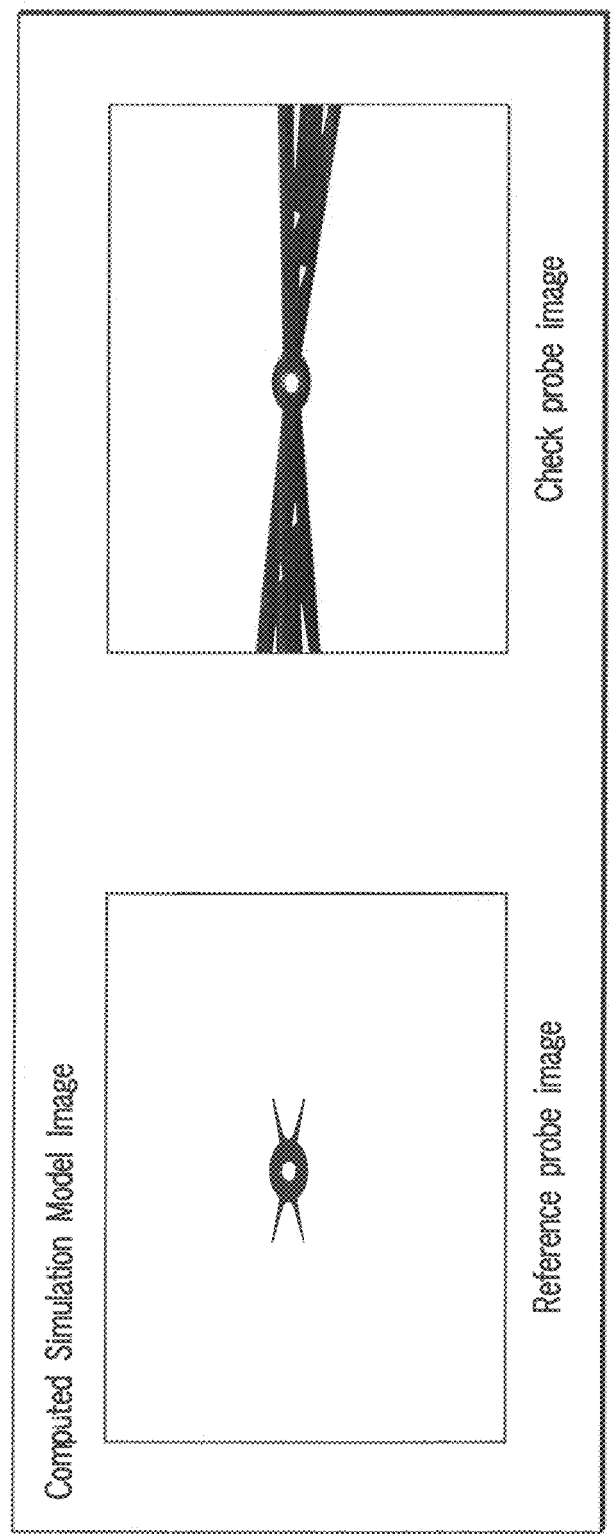

ULTRASOUND PROBE DIAGNOSING APPARATUS, ULTRASOUND DIAGNOSTIC APPARATUS, AND ULTRASOUND PROBE DIAGNOSING METHOD

CROSS-REFERENCE TO RELATED APPLICATIONS

This application is a divisional of U.S. application Ser. No. 11/213,700 filed Aug. 30, 2005, and is based upon and claims the benefit of priority from prior Japanese Patent Applications No. 2004-252973, filed Aug. 31, 2004; No. 2004-252974, filed Aug. 31, 2004; No. 2004-252975, filed Aug. 31, 2004; No. 2004-252976, filed Aug. 31, 2004; No. 2004-252977, filed Aug. 31, 2004; No. 2004-267216, filed Sep. 14, 2004; and No. 2004-275982, filed Sep. 22, 2004, the entire contents of all of which are incorporated herein by reference.

BACKGROUND OF THE INVENTION

1. Field of the Invention

The present invention relates to an ultrasound probe diagnosing apparatus and ultrasound probe diagnosing method which diagnose an ultrasound probe used by an ultrasound diagnostic apparatus, and an ultrasound diagnostic apparatus having a function of diagnosing an ultrasound probe.

2. Description of the Related Art

A technique of diagnosing an ultrasound probe on the basis of signals received by the ultrasound probe has been known through, for example, Jpn. Pat. Appln. KOKAI Publication Nos. 8-238243 and 10-227772.

A technique of detecting the transmission/reception characteristics of an ultrasound probe by using signals obtained by receiving ultrasound waves reflected by a test object like a reflector placed to face the ultrasound probe through the ultrasound probe has been know through, for example, Jpn. Pat. Appln. KOKAI Publication No. 2003-144432.

It has been difficult to efficiently diagnose an ultrasound probe by using these related arts.

BRIEF SUMMARY OF THE INVENTION

It has therefore been required to efficiently diagnose an ultrasound probe.

According to a first aspect of the present invention, there is provided an ultrasound probe diagnosing apparatus which diagnoses an ultrasound probe having an array of a plurality of ultrasound transducing elements on the basis of how the ultrasound probe receives reflected ultrasound waves from a test object placed to face the ultrasound probe, comprising: a part which detects a posture of the ultrasound probe with respect to the test object by comparing reflected ultrasound signals received by at least some of the plurality of ultrasound transducing elements; and a presenting part which presents information based on the detected posture.

According to a second aspect of the present invention, there is provided an ultrasound diagnostic apparatus which includes an ultrasound probe having an array of a plurality of ultrasound transducing elements, and obtains information for diagnosing a subject to be examined on the basis of reflected ultrasound waves received from the subject by the ultrasound probe, comprising: a part which is placed to face the ultrasound probe and detects a posture of the ultrasound probe with respect to a test object different from the subject by causing at least some of the plurality of ultrasound transducing elements to receive reflected ultrasound waves from the test object and comparing reflected ultrasound signals output from the ultrasound transducing elements with each other, and a presenting part which presents information based on the detected posture.

According to a third aspect of the present invention, there is provided an ultrasound probe diagnosing method of diagnosing an ultrasound probe having an array of a plurality of ultrasound transducing elements on the basis of how the ultrasound probe receives reflected ultrasound waves from a test object placed to face the ultrasound probe, comprising: causing at least some of the plurality of ultrasound transducing elements to receive the ultrasound waves; detecting a posture of the ultrasound probe with respect to the test object by comparing reflected ultrasound signals output from the some ultrasound transducing elements; and presenting information based on the detected posture.

According to a fourth aspect of the present invention, there is provided an ultrasound probe diagnosing apparatus which diagnoses an ultrasound probe on the basis of how the ultrasound probe receives a reflected ultrasound wave from a test object placed to face the ultrasound probe, comprising: a setting part which variably sets a repetition period of ultrasound wave transmission/reception; a part which adds reflected ultrasound signals from the ultrasound probe in corresponding phases for the each set period; and a diagnosing part which diagnoses the ultrasound probe on the basis of the added signals.

According to a fifth aspect of the present invention, there is provided an ultrasound probe diagnosing apparatus which diagnoses an ultrasound probe on the basis of how the ultrasound probe receives reflected ultrasound waves from a test object placed to face the ultrasound probe, comprising: a setting part which variably sets a transmission/reception period in repetitive ultrasound wave transmission/reception for each ultrasound wave transmission/reception; a part which adds reflected ultrasound signals from the ultrasound probe for the each set period while leading edges of the signals are matched with each other; and a diagnosing part which diagnoses the ultrasound probe on the basis of the added signals.

According to a sixth aspect of the present invention, there is provided an ultrasound diagnostic apparatus which includes an ultrasound probe and obtains information for diagnosis on a subject to be examined on the basis of reflected ultrasound waves received from the subject by the ultrasound probe, comprising: a setting part which variably sets a repetition period of ultrasound wave transmission/reception with respect to a test object different from the subject; a part which adds reflected ultrasound signals from the ultrasound probe in corresponding phases for the each set period; and a diagnosing part which diagnoses the ultrasound probe on the basis of the added signals.

According to a seventh aspect of the present invention, there is provided an ultrasound diagnostic apparatus which includes an ultrasound probe and obtains information for diagnosis on a subject to be examined on the basis of reflected ultrasound waves received from the subject by the ultrasound probe, comprising: a setting part which variably sets a repetition transmission/reception period for each ultrasound wave transmission/reception with respect to a test object different from the subject; a part which adds reflected ultrasound signals from the ultrasound probe for the each set period while leading edges of the signals are matched with each other; and a diagnosing part which diagnoses the ultrasound probe on the basis of the added signals.

According to an eighth aspect of the present invention, there is provided an ultrasound probe diagnosing method of diagnosing an ultrasound probe on the basis of how the ultrasound probe receives a reflected ultrasound wave from a test object placed to face the ultrasound probe, comprising: variably setting a repetition period of ultrasound wave transmission/reception; adding reflected ultrasound signals from the ultrasound probe in corresponding phases for the each set period; and diagnosing the ultrasound probe on the basis of the added signals.

According to a ninth aspect of the present invention, there is provided an ultrasound probe diagnosing method of diagnosing an ultrasound probe on the basis of how the ultrasound probe receives reflected ultrasound waves from a test object placed to face the ultrasound probe, comprising: variably setting a transmission/reception period in repetitive ultrasound wave transmission/reception for each ultrasound wave transmission/reception; adding reflected ultrasound signals output from the ultrasound probe for the each set period while leading edges of the signals are matched with each other; and diagnosing the ultrasound probe on the basis of the added signals.

According to a 10th aspect of the present invention, there is provided an ultrasound probe diagnosing apparatus which diagnoses an ultrasound probe having signal lines for transmitting signals transmitted/received by ultrasound transducing elements, comprising: a part which applies a test voltage to the signal line; and a determining part which determines a state of the ultrasound transducing element or the signal line on the basis of a voltage value of the ultrasound transducing element or the signal line upon application of the test voltage.

According to a 11th aspect of the present invention, there is provided an ultrasound probe diagnosing apparatus which diagnoses an ultrasound probe including an electronic circuit which has a signal line for transmitting a signal transmitted/received by an ultrasound transducing element and is configured to apply a bias voltage to the signal line, comprising: a detecting part which detects the bias voltage applied to the signal line; and a determining part which determines a state of the signal line on the basis of whether the bias voltage is detected by the detecting part.

According to a 12th aspect of the present invention, there is provided an ultrasound probe diagnosing apparatus which diagnoses an ultrasound probe of a first type which has a signal line for transmitting a signal to be transmitted/received by an ultrasound transducing element or an ultrasound probe of a second type which includes an electronic circuit which has a signal line for transmitting a signal to be transmitted/received by an ultrasound transducing element and is configured to apply a bias voltage to the signal line, comprising: a probe identifying part which identifies a diagnosis target as an ultrasound probe of the first type or an ultrasound probe of the second type; a part which changes an application state of a test voltage to the signal line in accordance with identification of the diagnosis target as an ultrasound probe of the first type; a first determining part which determines a state of the signal line on the basis of a transient response characteristic of a signal line voltage of the signal line when the application state of the test voltage is changed; a detecting part which detects the bias voltage applied to the signal line, in accordance with identification of a diagnosis target as an ultrasound probe of the second type by the probe identifying part; and a second determining part which determines a state of the signal line on the basis of whether the bias voltage is detected by the detecting part.

According to a 13th aspect of the present invention, there is provided an ultrasound diagnostic apparatus which includes an ultrasound probe having a signal line for transmitting a signal to be transmitted/received by an ultrasound transducing element, and obtains information for diagnosis on a subject to be examined on the basis of a reflected ultrasound wave received from the subject by the ultrasound probe, comprising: a part which applies a test voltage to the signal line; and a determining part which determines a state of the ultrasound transducing element or the signal line on the basis of a voltage value of the ultrasound transducing element or the signal line upon application of the test voltage.

According to a 14th aspect of the present invention, there is provided an ultrasound diagnostic apparatus which includes an ultrasound probe having an electronic circuit which has a signal line for transmitting a signal to be transmitted/received by an ultrasound transducing element and is configured to apply a bias voltage to the signal line, and obtains information for diagnosis on a subject to be examined on the basis of a reflected ultrasound wave received from the subject by the ultrasound probe, comprising: a detecting part which detects the bias voltage applied to the signal line; and a determining part which determines a state of the signal line on the basis of whether the bias voltage is detected by the detecting part.

According to a 15th aspect of the present invention, there is provided an ultrasound diagnostic apparatus which includes an ultrasound probe of a first type which has a signal line for transmitting a signal to be transmitted/received by an ultrasound transducing element or an electronic circuit which has a signal line for transmitting a signal to be transmitted/received by an ultrasound transducing element and is configured to apply a bias voltage to the signal line, and obtains information for diagnosis on a subject to be examined on the basis of a reflected ultrasound wave received from the subject by the ultrasound probe, comprising: a probe identifying part which identifies the ultrasound probe as the first type or second type; a part which changes an application state of a test voltage to the signal line in accordance with identification of the ultrasound probe as the first type; a first determining part which determines a state of the signal line on the basis of a transient response characteristic of a signal line voltage of the signal line when the application state of the test voltage is changed; a detecting part which detects the bias voltage applied to the signal line, in accordance with identification of the ultrasound probe as the second type; and a second determining part which determines a state of the signal line on the basis of whether the bias voltage is detected by the detecting part.

According to a 16th aspect of the present invention, there is provided an ultrasound probe diagnosing method of diagnosing an ultrasound probe having signal lines for transmitting signals transmitted/received by ultrasound transducing elements, comprising: applying a test voltage to the signal line; and determining a state of the ultrasound transducing element or the signal line on the basis of a voltage value of the ultrasound transducing element or the signal line upon application of the test voltage.

According to a 17th aspect of the present invention, there is provided an ultrasound probe diagnosing method of diagnosing an ultrasound probe including an electronic circuit which has a signal line for transmitting a signal transmitted/received by an ultrasound transducing element and is configured to apply a bias voltage to the signal line, comprising: detecting the bias voltage applied to the signal line; and determining a state of the signal line on the basis of whether the bias voltage is detected by the detecting part.

According to a 18th aspect of the present invention, there is provided an ultrasound probe diagnosing method of diagnosing an ultrasound probe of a first type which has a signal line for transmitting a signal to be transmitted/received by an ultrasound transducing element or an ultrasound probe of a second type which includes an electronic circuit which has a signal line for transmitting a signal to be transmitted/received by an ultrasound transducing element and is configured to apply a bias voltage to the signal line, comprising: identifying a diagnosis target as an ultrasound probe of the first type or an ultrasound probe of the second type; changing an application state of a test voltage to the signal line in accordance with identification of the diagnosis target as an ultrasound probe of the first type; determining a state of the signal line on the basis of a transient response characteristic of a signal line voltage of the signal line when the application state of the test voltage is changed; detecting the bias voltage applied to the signal line in accordance with identification of a diagnosis target as an ultrasound probe of the second type; and determining a state of the signal line on the basis of whether the bias voltage is detected.

According to a 19th aspect of the present invention, there is provided an ultrasound probe diagnosing apparatus which diagnoses an ultrasound probe, of a plurality of ultrasound probes, which is set as a diagnosis target, comprising: a measuring part which measures a feature value of a reflected ultrasound signal received from a test object by the ultrasound probe set as the diagnosis target; and a determining part which determines, on the basis of a reference value, of reference values corresponding to the plurality of ultrasound probes, which corresponds to the ultrasound probe set as the diagnosis target and the measured feature value, whether the ultrasound probe set as the diagnosis target is normal.

According to a 20th aspect of the present invention, there is provided an ultrasound probe diagnosing apparatus which is configured to access a first database in which a first reference value concerning feature values corresponding to a plurality of ultrasound probes is written and a second database in which a second reference value concerning variation degrees of the feature values is written, and diagnoses an ultrasound probe set as a diagnosis target, comprising: a measuring part which measures the feature value of a reflected ultrasound signal received from a test object by the ultrasound probe set as the diagnosis target; a part which obtains a variation degree of the measured feature value; an acquiring part which acquires the first reference value and second reference value corresponding to the ultrasound probe set as the diagnosis target from the first database and second database; and a determining part which determines, on the basis of comparison results obtained by comparing the measured feature value with the first reference value and comparing the obtained variation degree with the second reference value, whether the ultrasound probe set as the diagnosis target is normal.

According to a 21st aspect of the present invention, there is provided an ultrasound probe diagnosing apparatus which is configured to access a database in which reference values concerning at least two of an amplitude, center frequency, and bandwidth with respect to each of a plurality of ultrasound probes are written, and diagnoses an ultrasound probe set as a diagnosis target, comprising: a measuring part which measures, as feature values, at least two of an amplitude, center frequency, and bandwidth of a reflected ultrasound signal received from a test object by the ultrasound probe set as the diagnosis target; an acquiring part which acquires a reference value concerning each of the measured feature values from the database in accordance with the ultrasound probe set as the diagnosis target; and a determining part which determines, on the basis of comparison results obtained by comparing each of the measured feature values with the reference value corresponding to the each feature value, whether the ultrasound probe set as the diagnosis target is normal.

According to a 22nd aspect of the present invention, there is provided an ultrasound probe diagnosing apparatus which is configured to access a first database and second database, and diagnoses an ultrasound probe, of a plurality of ultrasound probes, which is set as a diagnosis target, the first database having a first reference value written concerning values of at least two of an amplitude, center frequency, and bandwidth with respect to each of the plurality of ultrasound probes, and the second database having a second reference value written concerning variation degrees of at least two of an amplitude, center frequency, and bandwidth with respect to each of the plurality of ultrasound probes, the apparatus comprising: a measuring part which measures, as feature values, at least two of an amplitude, center frequency, and bandwidth of a reflected ultrasound signal received from a test object by the ultrasound probe set as the diagnosis target; a part which obtains a variation degree of each of the measured feature values; an acquiring part which acquires a first reference value and second reference value concerning each of the measured feature values from the database in accordance with the ultrasound probe set as the diagnosis target; and a determining part which determines, on the basis of comparison results obtained by comparing each of the measured feature values with the first reference value corresponding to the each feature value and comparing each of the obtained variation degrees with the second reference value corresponding to the each variation degree, whether the ultrasound probe set as the diagnosis target is normal.

According to a 23rd aspect of the present invention, there is provided an ultrasound diagnostic apparatus in which one of a plurality of ultrasound probes is selectively mounted to obtain information for diagnosis on a subject to be examined on the basis of a reflected ultrasound wave received from the subject by the mounted ultrasound probe, comprising: a measuring part which measures a feature value of a reflected ultrasound signal received from a test object, by the mounted ultrasound probe; and a determining part which determines, on the basis of a reference value, of reference values corresponding to the plurality of ultrasound probes, which corresponds to the mounted ultrasound probe and the measured feature value, whether the mounted ultrasound probe is normal.

According to a 24th aspect of the present invention, there is provided an ultrasound probe diagnosing apparatus in which one of a plurality of ultrasound probes is selectively mounted to obtain information for diagnosis on a subject to be examined on the basis of a reflected ultrasound wave received from the subject by the mounted ultrasound probe, the ultrasound diagnostic apparatus being configured to access a first database in which a first reference value concerning a feature value of each of the plurality of ultrasound probes and to access a second database in which a second reference value concerning a variation degree of the feature value, comprising: a measuring part which measures the feature value of a reflected ultrasound signal received from a test object by the mounted ultrasound probe; a part which obtains a variation degree of the measured feature value; an acquiring part which acquires the first reference value and second reference value corresponding to the mounted ultrasound probe from the first database and second database; and a determining part which determines, on the basis of comparison results obtained by comparing the measured feature value with the first reference value and comparing the obtained variation degree with the second reference value, whether the mounted ultrasound probe is normal.

According to a 25th aspect of the present invention, there is provided an ultrasound diagnostic apparatus in which one of a plurality of ultrasound probes is selectively mounted to obtain information for diagnosis on a subject to be examined on the basis of a reflected ultrasound wave received from the subject by the mounted ultrasound probe, and which is configured to access a database in which reference values concerning at least two of an amplitude, center frequency, and bandwidth with respect to each of the plurality of ultrasound probes are written, comprising: a measuring part which measures, as feature values, at least two of an amplitude, center frequency, and bandwidth of a reflected ultrasound signal received from a test object by the mounted ultrasound probe; an acquiring part which acquires a reference value concerning each of the measured feature values from the database in accordance with the mounted ultrasound probe; and a determining part which determines, on the basis of comparison results obtained by comparing each of the measured feature values with the reference value corresponding to the each feature value, whether the mounted ultrasound probe is normal.

According to a 26th aspect of the present invention, there is provided an ultrasound diagnostic apparatus in which one of a plurality of ultrasound probes is selectively mounted to obtain information for diagnosis on a subject to be examined on the basis of a reflected ultrasound wave received from the subject by the mounted ultrasound probe, the ultrasound diagnostic apparatus being configured to access the first database and second database, the first database having a first reference value written concerning values of at least two of an amplitude, center frequency, and bandwidth with respect to each of the plurality of ultrasound probes, and the second database having a second reference value written concerning variation degrees of at least two of an amplitude, center frequency, and bandwidth with respect to each of the ultrasound probes, the apparatus comprising: a measuring part which measures at least two of an amplitude, center frequency, and bandwidth of a reflected ultrasound signal received from a test object by the mounted ultrasound probe as feature values; a part which obtains a variation degree of each of the measured feature values; an acquiring part which acquires a first reference value and second reference value concerning the measured feature values from the database in accordance with the mounted ultrasound probe; and a determining part which determines, on the basis of comparison results obtained by comparing each of the measured feature values with the first reference value corresponding to the each feature value and comparing each of the obtained variation degrees with the second reference value corresponding to the each variation degree, whether the mounted ultrasound probe is normal.

According to a 27th aspect of the present invention, there is provided an ultrasound probe diagnosing method of diagnosing an ultrasound probe, of a plurality of ultrasound probes, which is set as a diagnosis target, comprising: measuring a feature value of a reflected ultrasound signal received from a test object by the ultrasound probe set as the diagnosis target; and determining, on the basis of a reference value, of reference values corresponding to the plurality of ultrasound probes, which corresponds to the ultrasound probe set as the diagnosis target and the measured feature value, whether the ultrasound probe set as the diagnosis target is normal.

According to a 28th aspect of the present invention, there is provided an ultrasound probe diagnosing method of diagnosing an ultrasound probe set as a diagnosis target by using a first database in which a first reference value concerning feature values corresponding to a plurality of ultrasound probes is written and a second database in which a second reference value concerning variation degrees of the feature values is written, comprising: measuring the feature value of a reflected ultrasound signal received from a test object by the ultrasound probe set as the diagnosis target; obtaining a variation degree of the measured feature value; acquiring the first reference value and second reference value corresponding to the ultrasound probe set as the diagnosis target from the first database and second database; and determining, on the basis of comparison results obtained by comparing the measured feature value with the first reference value and comparing the obtained variation degree with the second reference value, whether the ultrasound probe set as the diagnosis target is normal.

According to a 29th aspect of the present invention, there is provided an ultrasound probe diagnosing method of diagnosing an ultrasound probe set as a diagnosis target by using a database in which reference values concerning at least two of an amplitude, center frequency, and bandwidth with respect to each of a plurality of ultrasound probes are written, comprising: measuring, as feature values, at least two of an amplitude, center frequency, and bandwidth of a reflected ultrasound signal received from a test object by the ultrasound probe set as the diagnosis target; acquiring a reference value concerning each of the measured feature values from the database in accordance with the ultrasound probe set as the diagnosis target; and determining, on the basis of comparison results obtained by comparing each of the measured feature values with the reference value corresponding to the each feature value, whether the ultrasound probe set as the diagnosis target is normal.

According to a 30th aspect of the present invention, there is provided an ultrasound probe diagnosing method of diagnosing an ultrasound probe, of a plurality of ultrasound probes, which is set as a diagnosis target, by using a first database and second database, the first database having a first reference value written concerning values of at least two of an amplitude, center frequency, and bandwidth with respect to each of the plurality of ultrasound probes, and the second database having a second reference value written concerning variation degrees of at least two of an amplitude, center frequency, and bandwidth with respect to each of the plurality of ultrasound probes, the method comprising: measuring, as feature values, at least two of an amplitude, center frequency, and bandwidth of a reflected ultrasound signal received from a test object by the ultrasound probe set as the diagnosis target; obtaining a variation degree of each of the measured feature values; acquiring a first reference value and second reference value concerning each of the measured feature values from the database in accordance with the ultrasound probe set as the diagnosis target; and determining, on the basis of comparison results obtained by comparing each of the measured feature values with the first reference value corresponding to the each feature value and comparing each of the obtained variation degrees with the second reference value corresponding to the each variation degree, whether the ultrasound probe set as the diagnosis target is normal.

According to a 31st aspect of the present invention, there is provided an ultrasound probe diagnosing apparatus which diagnoses an ultrasound probe, comprising: a checking part which checks a state of the ultrasound probe on the basis of a feature value of the ultrasound probe; an acquiring part which acquires outer appearance information concerning an appearance state of the ultrasound probe; and a presenting part which presents both the check result and the acquired outer appearance information.

According to a 32nd aspect of the present invention, there is provided an ultrasound diagnostic apparatus which includes an ultrasound probe, and obtains information for diagnosis on a subject to be examined on the basis of a reflected ultrasound wave received from the subject by the ultrasound probe, comprising: an ultrasound probe diagnosing apparatus; a checking part which checks a state of the ultrasound probe on the basis of a feature value of the ultrasound probe; an acquiring part which acquires outer appearance information concerning an appearance state of the ultrasound probe; and a presenting part which presents both the check result and the acquired outer appearance information.

According to a 33rd aspect of the present invention, there is provided an ultrasound probe diagnosing method of diagnosing an ultrasound probe, comprising: checking a state of the ultrasound probe on the basis of a feature value of the ultrasound probe; acquiring outer appearance information concerning an appearance state of the ultrasound probe; and presenting both the check result and the acquired outer appearance information.

According to a 34th aspect of the present invention, there is provided an ultrasound probe diagnosing apparatus which diagnoses an ultrasound probe having a plurality of channels each including an ultrasound transducing element, a signal line for transmitting a signal concerning the ultrasound transducing element, and an contact with the plurality of contacts being arrayed to form a connector, comprising: a part which checks each of the plurality of channels; and a presenting part which presents the check result in correspondence with an array of the plurality of contacts in the connector.

According to a 35th aspect of the present invention, there is provided an ultrasound diagnostic apparatus which includes an ultrasound probe having a plurality of channels each including an ultrasound transducing element, a signal line for transmitting a signal concerning the ultrasound transducing element, and an contact with the plurality of contacts being arrayed to form a connector, and obtains information for diagnosis on a subject to be examined on the basis of a reflected ultrasound wave received from the subject by the ultrasound probe, comprising: a part which checks each of the plurality of channels; and a presenting part which presents the check result in correspondence with an array of the plurality of contacts in the connector.

According to a 36th aspect of the present invention, there is provided an ultrasound probe diagnosing apparatus which diagnoses an ultrasound probe, comprising: a part which obtains a predetermined feature value of a reflected ultrasound signal received from a test object by the ultrasound probe; and a generating part which generates a simulation image simulating an ultrasound diagnostic apparatus using a virtual ultrasound probe constructed on the basis of the obtained feature value.

According to a 37th aspect of the present invention, there is provided an ultrasound probe diagnosing method of diagnosing an ultrasound probe, comprising: obtaining a predetermined feature value of a reflected ultrasound signal received from a test object by the ultrasound probe; and generating a simulation image simulating an ultrasound diagnostic apparatus using a virtual ultrasound probe constructed on the basis of the obtained feature value.

According to a 38th aspect of the present invention, there is provided an ultrasound probe diagnosing apparatus which diagnoses an ultrasound probe having an array of a plurality of ultrasound transducing elements on the basis of how the ultrasound probe receives reflected ultrasound waves from a test object placed to face the ultrasound probe, comprising: a part which makes a reception state of a reflected ultrasound wave in the ultrasound probe appropriate; a part which checks quality of a physical property of the ultrasound probe by comparison with a predetermined reference value; and a part which presents the check result.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a view showing a state wherein the posture of a head unit in FIG. 1 is inappropriate;

FIG. 5 is a timing chart showing the state of a reflected ultrasound signal in the state shown in FIG. 4;

FIGS. 6A, 6B, 6C, 6D, 6E, 6F, 6G are views for explaining the generation of a navigation window by the navigation processing unit in FIG. 1;

FIG. 15 is a block diagram showing the arrangement of an ultrasound diagnostic apparatus having a function of diagnosing an ultrasound probe according to the second and third embodiments;

FIGS. 16A, 16B are timing charts showing how the repetition period is changed in accordance with a difference in the focal length of the ultrasound probe shown in FIG. 15 in the second embodiment;

FIG. 19 is a block diagram showing the arrangement of an ultrasound diagnostic apparatus having a function of diagnosing an ultrasound probe according to the fourth embodiment;

FIG. 20 is a view showing how an ultrasound probe of the first type is connected to a connector in FIG. 19;

FIG. 24 is a block diagram showing the basic arrangement of an ultrasound diagnostic apparatus having a function of diagnosing an ultrasound probe according to the fifth to eighth embodiments;

FIG. 25 is a block diagram showing the characteristic arrangement of the ultrasound diagnostic apparatus according to the fifth embodiment;

FIG. 26 is a view showing the arrangement of a reference database in FIG. 25;

FIG. 28 is a block diagram showing the characteristic arrangement of an ultrasound diagnostic apparatus according to the sixth embodiment;

FIG. 32 is a view showing an example of how normal degrees are ranked;

FIG. 33 is a block diagram showing the arrangement of an ultrasound diagnostic apparatus having a function of diagnosing an ultrasound probe according to the ninth embodiment;

FIG. 34 is a view showing an example of a report generated by the ultrasound diagnostic apparatus in FIG. 33;

FIG. 36 is a block diagram showing the arrangement of an ultrasound diagnostic apparatus having a function of diagnosing an ultrasound probe according to the embodiment;

FIGS. 40A, 40B are views showing an example of an image displayed by the third display method;

FIG. 41 is a block diagram showing the arrangement of an ultrasound diagnostic apparatus having a function of diagnosing an ultrasound probe according to the 11th embodiment;

FIG. 43 is a view showing an example of a comparative display image.

DETAILED DESCRIPTION OF THE INVENTION

The embodiments of the present invention will be described below with reference to the views of the accompanying drawing.

First Embodiment

Figure 1:
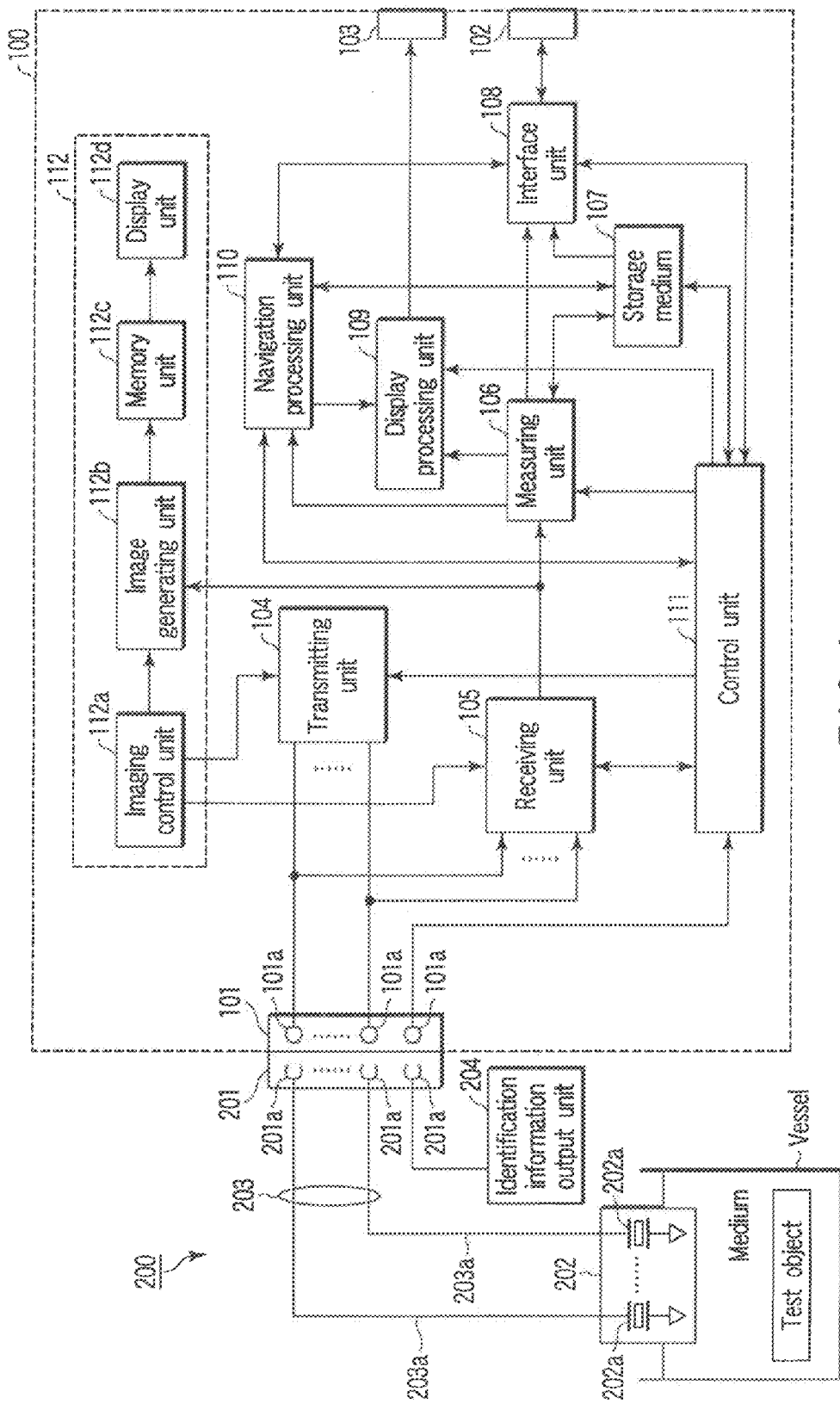
FIG. 1 is a block diagram showing the basic arrangement of an ultrasound probe diagnosing apparatus having a function of diagnosing an ultrasound probe according to the first embodiment of the present invention.

FIG. 1 is a block diagram showing the basic arrangement of an ultrasound diagnostic apparatus having a function of diagnosing an ultrasound probe according to the first embodiment. This ultrasound diagnostic apparatus includes a main unit 100 and ultrasound probe 200. The ultrasound probe 200 includes a connector 201, head unit 202, cable unit 203, and identification information output unit 204.

The connector 201 is connected to the main unit 100. The head unit 202 is formed by arraying a plurality of ultrasound transducing elements 202a one-dimensionally or two-dimensionally. Each of the ultrasound transducing elements 202a is connected to the connector 201 through a signal line 203a provided in the cable unit 203. The connector 201 is provided with contacts 201a connected to the signal lines 203a. That is, the ultrasound probe 200 comprises a plurality of channels in parallel, each including the contact 201a, ultrasound transducing element 202a, and signal line 203a.

The identification information output unit 204 outputs identification information assigned to the ultrasound probe 200. The connector 201 is also provided with a contact 201a connected to the identification information output unit 204.

The main unit 100 includes connectors 101, 102, and 103, a transmitting unit 104, a receiving unit 105, a measuring unit 106, a storage medium 107, an interface unit 108, a display processing unit 109, a navigation processing unit 110, a control unit 111, and a medical diagnosing unit 112.

The connector 201 provided in the ultrasound probe 200 is attached to the connector 101. The connector 101 has contacts 101a equal in number to the contacts 201a provided on the connector 201. The contacts 101a are so arranged as to come into contact with the contacts 201a, respectively, when the connector 201 is attached to the connector 101. An external device (not shown) is connected to the connector 102 through a communication cable (not shown) such as a USB (Universal Serial Bus) cable. This external device is, for example, a printer, network, personal computer, keyboard, and pointing device. A monitor device (not shown) is connected to the connector 103 through a monitor cable (not shown).

The transmitting unit 104 transmits excitation signals for exciting the ultrasound transducing elements 202a. The transmitting unit 104 can transmit excitation signals for the respective ultrasound transducing elements 202a in parallel. The receiving unit 105 receives the signals received by the ultrasound transducing elements 202a. The receiving unit 105 can receive the signals received by the ultrasound transducing elements 202a in parallel. The receiving unit 105 outputs the received signals.

The measuring unit 106 measures the feature values of the signals output from the receiving unit 105. A feature value includes, for example, the time required between transmitting an ultrasound wave and receiving the reflected ultrasound wave. The measuring unit 106 outputs measurement information indicating the measured feature values to the storage medium 107, interface unit 108, display processing unit 109, navigation processing unit 110, or control unit 111 under the control of the control unit 111. The storage medium 107 is, for example, a semiconductor memory. The storage medium 107 stores various kinds of information such as the above measurement information. The interface unit 108 performs communication processing conforming to, for example, the USB standard to realize communication with the external device connected to the connector 102. The display processing unit 109 generates an image signal for causing the monitor device connected to the connector 103 to display an image on the basis of the above measurement information, information supplied from the control unit 111, and the like.

The navigation processing unit 110 comprises, for example, a microprocessor. The navigation processing unit 110 determines the posture of the ultrasound probe 200, and more specifically, the posture of the head unit 202 by properly referring to the measurement information output from the measuring unit 106 and the data supplied from the storage medium 107 under the control of the control unit 111. The navigation processing unit 110 generates navigation window information for navigating the operation of changing the posture of the ultrasound probe 200 so as to eliminate the difference between the determined posture and the predetermined reference posture. The navigation window information is output to an external device through the interface unit 108 and connector 102 or output to the display processing unit 109.

The control unit 111 comprises, for example, a microprocessor. The control unit 111 systematically controls the respective units of the main unit 100 to realize operation for the diagnosis of the ultrasound probe 200. The control unit 111 also has a function of sending data necessary for processing in the navigation processing unit 110 from the storage medium 107 to the navigation processing unit 110.

The medical diagnosing unit 112 also includes an imaging control unit 112*a*, image generating unit 112*b*, memory unit 112*c*, and display unit 112*d*. The imaging control unit 112*a* controls the transmitting unit 104, receiving unit 105, and image generating unit 112*b* so as to perform proper imaging processing in accordance with diagnosis contents or the like. The image generating unit 112*b* generates display data for displaying an image for medical diagnosis on the basis of the signals output from the receiving unit 105. The image represented by display data includes, for example, a reconstructed image such as a tomographic image or three-dimensional image concerning an organ or blood flow in a subject to be examined or a text image or graph representing a measurement value such as a blood flow rate or its change. The memory unit 112*c* stores the above display data. The display unit 112*d* performs display operation based on the display data.

The operation of the ultrasound diagnostic apparatus having the above arrangement will be described next.

When medical diagnosis on a subject to be examined is to be performed by using the ultrasound probe 200, information useful for medical diagnosis can be presented by activating the medical diagnosing unit 112 in the same manner as a known ultrasound diagnostic apparatus.

In diagnosing the ultrasound probe 200, a maintenance operator places a test object in a medium such as water in a vessel such as a water bath and also makes the head unit 202 face the test object in advance, as shown in FIG. 1.

Figure 2A:
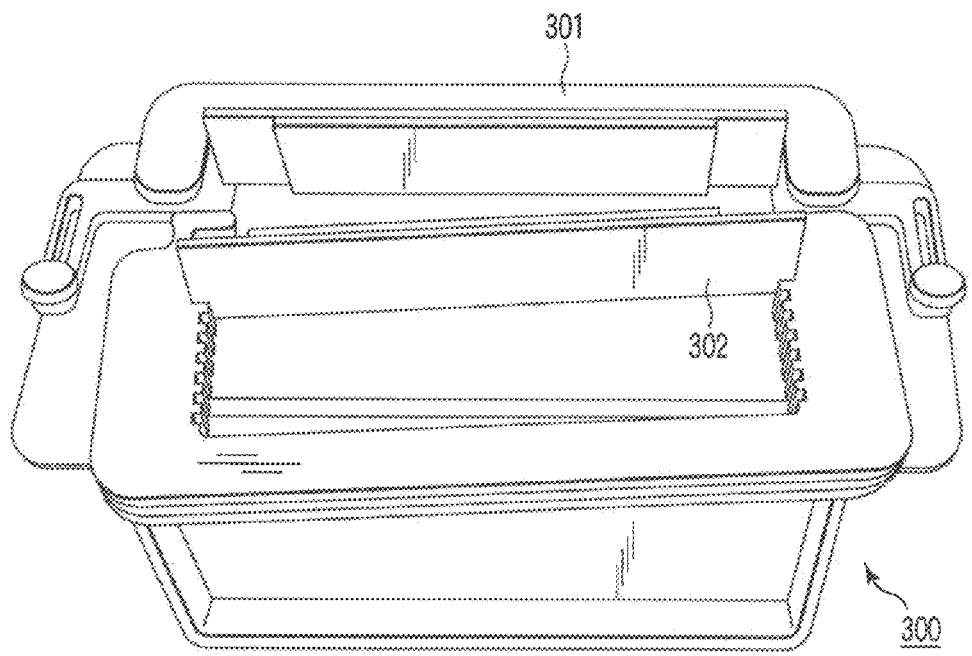
FIGS. 2A, 2B are views showing the outer appearance of a probe holder.
Figure 2B:
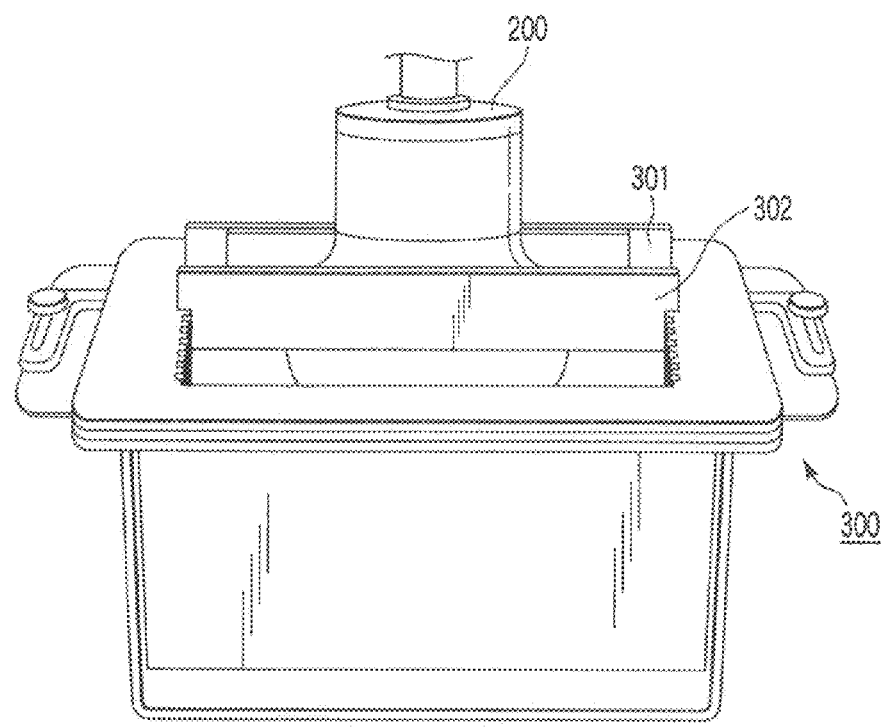

At this time, the ultrasound probe 200 is held by the probe holder 300 shown in FIG. 2A in a state like that shown in FIG. 2B. A probe holder 300 holds the ultrasound probe 200 by clamping it between two opposing restraining members 301 and 302. This allows the ultrasound probe 200 to only rotate about an axis along the pressing direction of the restraining members 301 and 302 and slide in a direction perpendicular to the pressing direction while fixing the posture of the probe in other directions.

Figure 3:
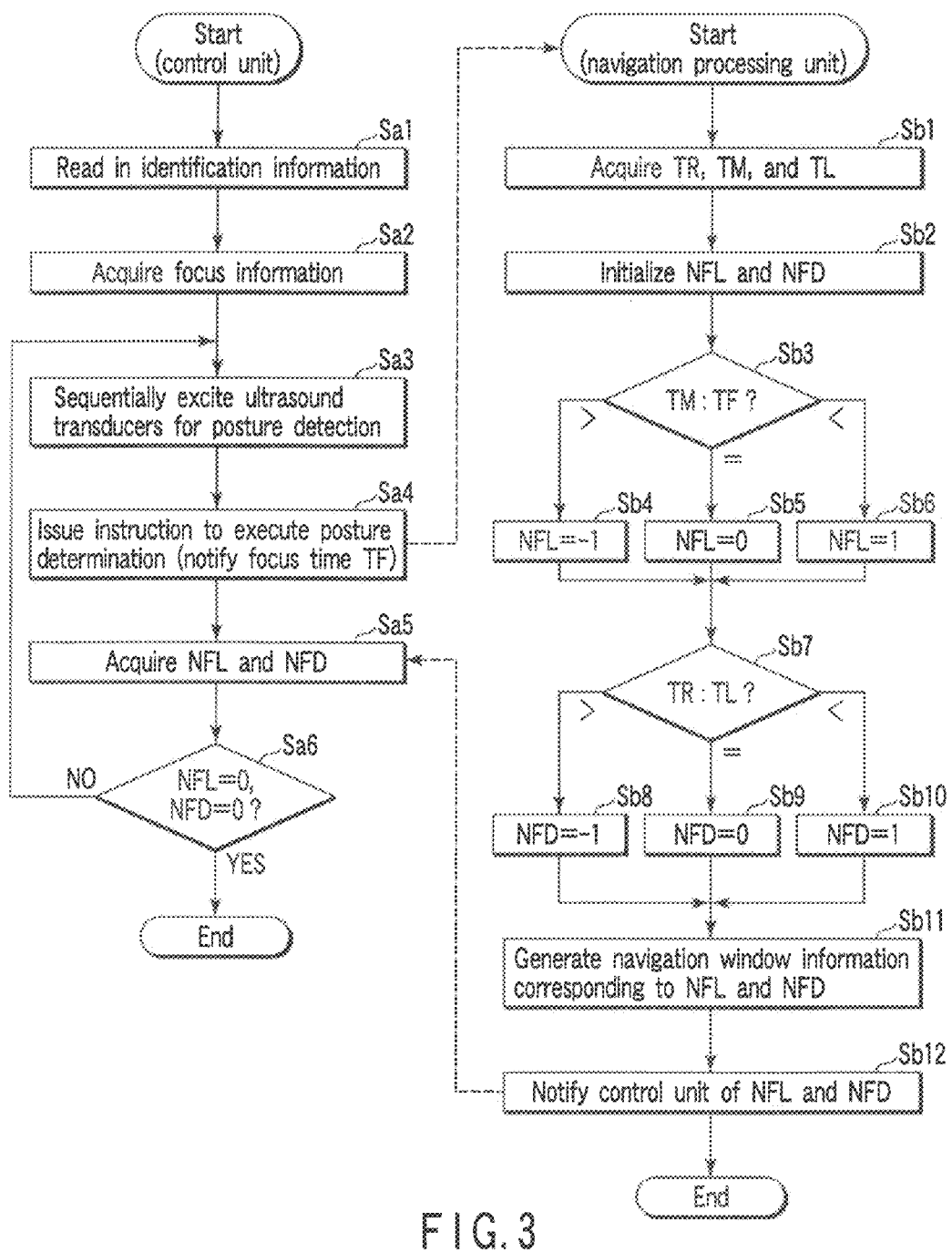
FIG. 3 is a flowchart showing a processing sequence for navigation by a control unit and navigation processing unit in FIG. 1.

If it is required to diagnose the ultrasound probe 200, the control unit 111 executes processing like that shown in FIG. 3. In step Sa1, the control unit 111 reads in the identification information output from the identification information output unit 204. In step Sa2, the control unit 111 acquires focus information concerning the model of the ultrasound probe 200 connected to the connector 101. The model of the ultrasound probe 200 is determined on the basis of the above identification information. The identification information is information for specifying each ultrasound probe 200, and does not generally include information indicating a model. The control unit 111 determines the model of the ultrasound probe 200 by referring to a database in which pieces of model information are written in correspondence with various kinds of identification information. The database may be acquired in advance from the external device connected to the connector 102 or stored in advance in the storage medium 107. Alternatively, information indicating a model may be contained in identification information, and the control unit 111 may directly determine the model of the ultrasound probe 200 from this information. Focus information is information containing the focus time TF which is the time required for an ultrasound wave to reciprocate to a focus point. The control unit 111 acquires focus information from the above database or another database. Note that when only the single model of the ultrasound probe 200 is to be diagnosed, such processing can be omitted.

In step Sa3, the control unit 111 causes the transmitting unit 104 to sequentially excite the ultrasound transducing elements 202*a* for posture detection which are selected in advance from all the ultrasound transducing elements 202*a*. In this case, the number of ultrasound transducing elements 202*a* for posture detection may be arbitrary as long as it is plural. The ultrasound transducing elements 202*a* for posture detection which are to be excited are preferably spaced apart as far as possible. In this embodiment, two ultrasound transducing elements 202*a* located on the two ends of the head unit 202 and one ultrasound transducing element 202*a* located in the middle of the head unit 202, i.e., a total of three ultrasound transducing elements 202*a*, are used as the ultrasound transducing elements 202*a* for posture detection. In the following description, for the sake of descriptive convenience, these three ultrasound transducing elements will be referred to as transducers R, L, and M. The transducer M is the ultrasound transducing element 202*a* located in the middle of the head unit 202. In addition, channels including the transducers R, L, and M will be referred to as channels CHR, CHL, and CHM, respectively.

When the transducers R, M, and L are excited, reflected ultrasound signals from the test object are received by the receiving unit 105 through the above exited transducers R, M, and L, signal lines 203*a*, contacts 201*a*, and contacts 101*a*. As a consequence, the digital signals of the reflected ultrasound signals from the channels CHR, CHM, and CHL are obtained and input to the measuring unit 106. The measuring unit 106 then measure times TR, TM, and TL taken between exciting the transducers. R, M, and L and receiving the corresponding reflected ultrasound signals.

In step Sa4, the control unit 111 instructs the navigation processing unit 110 to execute posture determination. At this time, the control unit 111 notifies the navigation processing unit 110 of a focus time TF indicated by the focus information acquired in step Sa2.

In response to this instruction, the navigation processing unit 110 starts processing like that shown in FIG. 3. In step Sb1, the navigation processing unit 110 acquires the times TR, TM, and TL measured by the measuring unit 106 in the above manner. In step Sb2, the navigation processing unit 110 initializes variables NFL and NFD.

In step Sb3, the navigation processing unit 110 compares the time TM with the focus time TF notified from the control unit 111. If the time TM is larger than the focus time TF, the processing of the navigation processing unit 110 advances from step Sb3 to step Sb4 to set the variable NFL to "−1". If the time TM is equal to the focus time TF, the processing of the navigation processing unit 110 advances from step Sb3 to step Sb5 to set the variable NFL to "0". If the time TM is smaller than the focus time TF, the processing of the navigation processing unit 110 advances from step Sb3 to step Sb6 to set the variable NFL to "1".

Letting C be the sound velocity of an ultrasound wave propagating in the medium, L be the distance between the ultrasound transducing element 202*a* and the test object, and T be the time required between transmitting an ultrasound wave and receiving it, it is known that T=2L/C. Therefore, as shown in FIG. 5, if the time TM is larger than the focus time TF, the distance LM between the transducer M and the test object is larger than the focal length LF of the ultrasound probe 200. The variable NFL is set to "−1" when distance LM>focal length LF, "0" when distance LM=focal length LF, and "1" when distance LM<focal length LF.

The processing of the navigation processing unit 110 advances from step Sb4, step Sb5, or step Sb6 to step Sb7. In step Sb7, the navigation processing unit 110 compares the time TR with the time TL. If the time TR is larger than the time TL, the processing of the navigation processing unit 110 advances from step Sb7 to step Sb8 to set the variable NFD to "−1". If the time TM is equal to the time TL, the processing of the navigation processing unit 110 advances from step Sb7 to step Sb8 to set the variable NFD to "0". If the time TM is smaller than the time TL, the processing of the navigation processing unit 110 advances from step Sb7 to step Sb10 to set the variable NFD to "1".

As described above, the times TR and TL are proportional to distances LR and LL between the transducers R and L and the test object. If, therefore, as shown in FIG. 5, the time TL is larger than the time TR, the distance LL is larger than the distance LR. In this case, for example, the head unit takes a posture like that shown in FIG. 4. The variable NFD is set to "−1" when distance LR>distance LL, "0" when distance LR=distance LL, and "1" when distance LR<distance LL.

The processing of the navigation processing unit 110 advances from step Sb8, step Sb9, or step S10 to step Sb11. In step Sb11, the navigation processing unit 110 generates navigation window information representing a navigation window corresponding to the variables NFL and NFD.

Assume that the navigation window uses the image shown in FIG. 6A as a base image. This base image contains arrows A1, A2, A3, and A4 pointing up, down, left, and right and arrows A5 and A6 pointing clockwise and counterclockwise.

The navigation processing unit 110 changes the colors of the arrows A1 and A2 in accordance with the variable NFL. More specifically, if the variable NFL is "−1", the navigation processing unit 110 changes the color of the arrow A2 as indicated by the hatching in FIG. 6B. If the variable NFL is "0", the navigation processing unit 110 changes neither of the colors of the arrows A1 and A2, as shown in FIG. 6B. If the variable NFL is "1", the navigation processing unit 110 changes the color of the arrow A1 as indicated by the hatching in FIG. 6D.

The navigation processing unit 110 changes the colors of the arrows A5 and A6 in accordance with the variable NFD. More specifically, if the variable NFD is "−1", the navigation processing unit 110 changes the color of the arrow A5 as indicated by the hatching in FIG. 6E. If the variable NFD is "0", the navigation processing unit 110 changes neither of the colors of the arrows A5 and A6 as shown in FIG. 6F. If the variable NFD is "1", the navigation processing unit 110 changes the color of the arrow A6 as indicated by the hatching in FIG. 6G.

The navigation processing unit 110 generates a navigation window by combining one of the windows shown in FIGS. 6A to 6D with one of the windows shown in FIGS. 6E to 6G. The navigation processing unit 110 outputs the navigation window information generated in this manner to the display processing unit 109. The display processing unit 109 generates a signal for causing the monitor device to display the navigation window on the basis of the navigation window information, and outputs the information to the connector 103. The navigation window information can be output to an external device through the interface unit 108 and connector 102.

In step Sb12, the navigation processing unit 110 notifies the control unit 111 of the variables NFL and NFD. The navigation processing unit 110 terminates the processing in FIG. 3.

Figure 7:
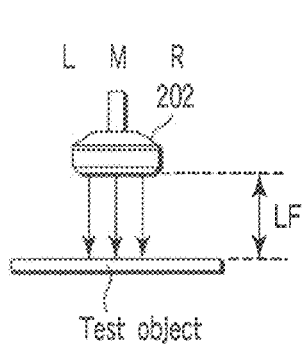
FIG. 7 is a view showing a state wherein the posture of the head unit in FIG. 1 is appropriate.
Figure 8:
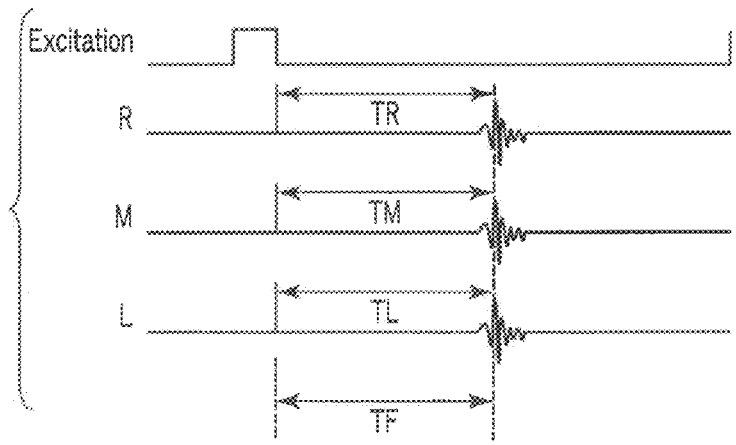
FIG. 8 is a timing chart showing the state of a reflected ultrasound signal in the state shown in FIG. 7.

If the maintenance operator changes the posture of the head unit 202 in accordance with the navigation window, the difference between the time TM and the focus time TF or the difference between the time TL and the time TR is reduced. As shown in FIG. 8, if the time TM coincides with the focus time TF, the distance LM coincides with the focal length LF. In addition, if the time TR coincides with the time TL, the distances LR, LM, and LL coincide with each other. Therefore, all the distances LR, LM, and LL coincide with the focal length LF. That is, as shown in FIG. 7, the test object is located at the focus point of the ultrasound probe 200, and the array surface of the ultrasound transducing elements 202*a* becomes parallel to the test object. In this state, since the time TM coincides with the focus time TF and the time TR coincides with the time TL, both the variables NFL and NFD become "0".

Upon issuing an instruction to execute posture determination in step Sa4, the control unit 111 advances to step Sa5. In step S5, the control unit 111 acquires the variables NFL and NFD notified from the navigation processing unit 110 in the above manner. In step Sa6, the control unit 111 checks whether both the variables NFL and NFD are "0". If either of the variables NFL and NFD is not "0", the control unit 111 repeats the processing in step Sa3 and the subsequent steps. If the head unit 202 takes the posture shown in FIG. 7, and both the variables NFL and NFD become "0", the control unit 111 terminates the processing in FIG. 3.

As described above, according to the first embodiment, the maintenance operator can place the test object at the focus point of the head unit 202 and make the array surface of the ultrasound transducing elements 202*a* parallel to the test object by changing the posture of the head unit 202 as indicated by the arrows whose colors are changed in the navigation window. This therefore facilitates the operation by the maintenance operator, reduces the load on the maintenance operator, and allows the maintenance operator to properly adjust the posture of the ultrasound probe.

The first embodiment can be variously modified as follows.

Figure 9:
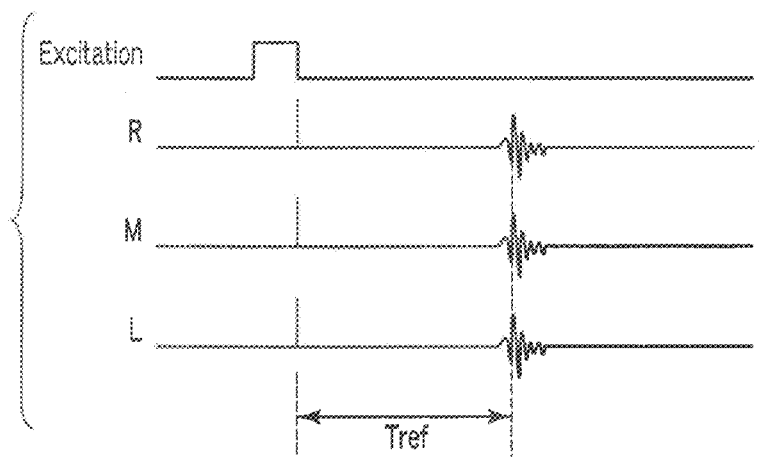
FIG. 9 is a timing chart showing how times TR, TM, and TL are matched with a reference time Tref irrelevant to a focus time TF.

As shown in FIG. 9, navigation may be performed to match the respective times TR, TM, and TL with the reference time Tref irrelevant to the focus time TF. At this time, although the reference time Tref may be arbitrarily set, any one of the times TR, TM, and TL measured at first or a time predetermined for each of the ultrasound probes 200 may be used.

Navigation may be performed to match the respective times TR, TM, and TL with each other without referring to a reference time like the focus time TF.

Figure 10:
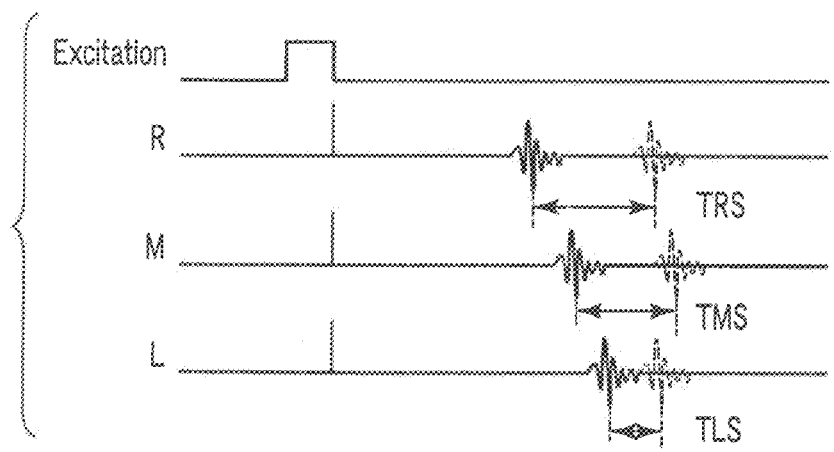
FIG. 10 is a timing chart showing how navigation is performed with reference to the posture of the head unit set in the past.

Navigation may be performed with reference to the posture of the head unit 202 which is set in the past. More specifically, the times TR, TM, and TL measured by the measuring unit 106 in the past are stored as times TRold, TMold, and TLold in the storage medium 107. Navigation is performed to bring newly measured times TRnew, TMnew, and TLnew to the times TRold, TMold, and TLold, respectively. For example, as TRS=TRnew−TRold, TMS=TMnew−TMold, and TLS=TLnew−TLold, differential times TRS, TMS, and TLS like those shown in FIG. 10 are obtained. If the signs of the differential times TRS, TMS, and TLS are (+), navigation may be performed to bring the right end, middle, and left end of the head unit 202 close to the test object. If the signs of the differential times TRS, TMS, and TLS are (−), navigation may be performed to move the right end, middle, and left end of the head unit 202 away from the test object. Although the times TR, TM, and TL measured at an arbitrary time point may be set as the times TRold, TMold, and TLold, these times may be measured at a time point when a registration instruction is issued by the maintenance operator.

Figure 11:
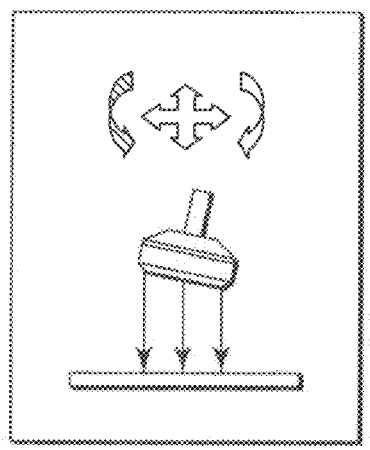
FIG. 11 is a view showing a modification of the navigation window.

The navigation window may include a photograph of the head unit 202 or computer graphics image as shown in FIG. 11. This makes it easy for the maintenance operator to recognize which posture change of the head unit 202 is indicated by a given arrow. In addition, the tilt angle of the head unit 202 may be obtained on the basis of the times TR, TM, and TL to tilt the photograph of the head unit 202 or computer graphics image on the basis of the tilt angle, as shown in FIG. 11. This allows the maintenance operator to intuitively recognize what posture the head unit 202 is in. Note that if a photograph or computer graphics image is tilted in this manner, navigation display with arrows can be omitted.

Figure 12:
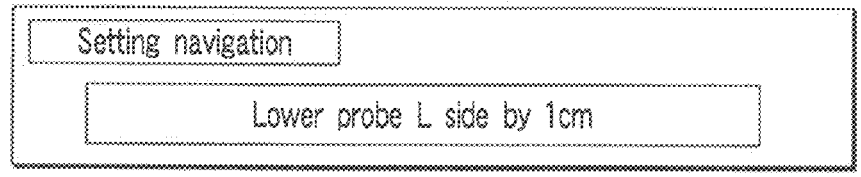
FIG. 12 is a view showing another modification of the navigation window.

A navigation window may be designed to display a character message as shown in FIG. 12. Alternatively, the navigation processing unit 110 may generate sound information for outputting the above character message in the form of sound.

Figure 13:
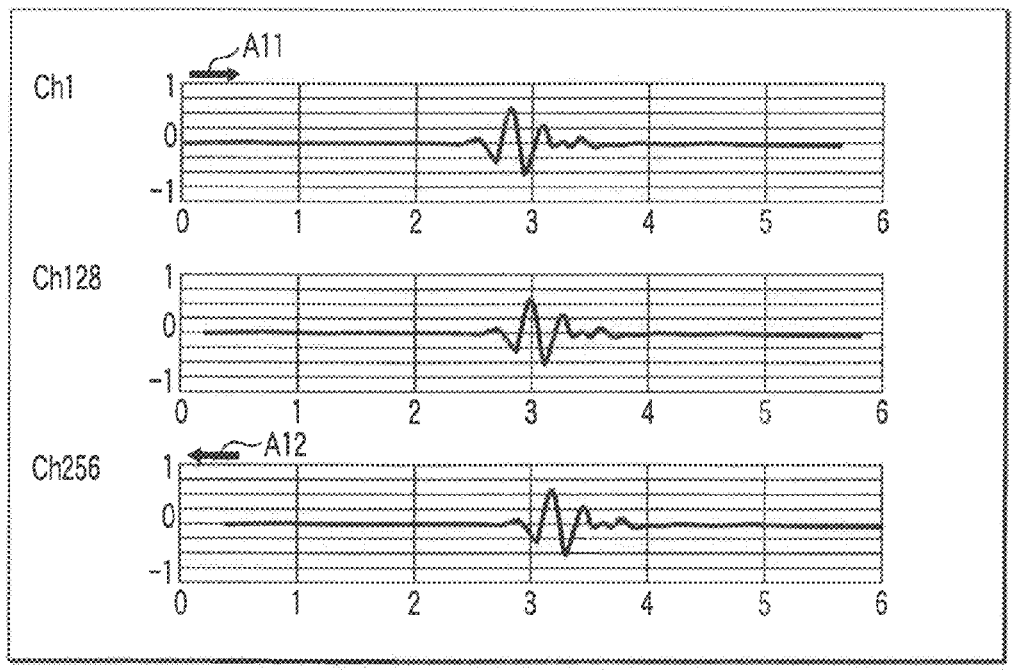
FIG. 13 is a graph showing still another modification of the navigation window.

As shown in FIG. 13, a navigation window may be designed such that arrows A11 and A12 for navigation are displayed while being superimposed on images respectively indicating the waveforms of reflected ultrasound signals received through the channels CHR, CHM, and CHL.

A moving image or animation which indicates how the posture of the head unit 202 is changed may be prepared, and may be included in a navigation window.

If the resolution with which the times TR, TM, and TL are measured by the measuring unit 106 is high, it is difficult to adjust the posture of the head unit 202 so as to match the time TM with the focus time TF and also match the time TR with the time TL. In such a case, allowable ranges are preferably provided in comparing the time TM with the focus time TF and comparing the time TR with the time TL. If, for example, the difference between the time TM and the focus time TF falls within the allowable range, it may be determined that the time TM coincides with the focus time TF. If the difference between the time TR and the time TL falls within the allowable range, it may be determined that the time TR coincides with the time TL.

Figure 14:
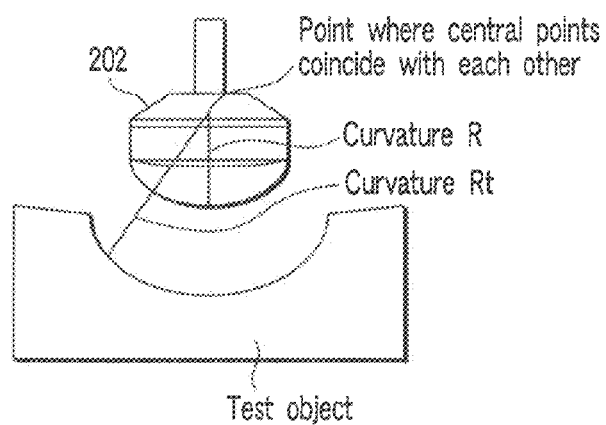
FIG. 14 is a view showing the appropriate posture of the head unit when the ultrasound probe is of a convex system.

If the ultrasound probe 200 is of a convex type, as shown in FIG. 14, a test object to be used is the one that has a reflecting surface with a curvature Rt corresponding to a curvature R of the emitting surface of the ultrasound probe 200. In this case, the curvature Rt is given by Rt=R+F where F is the focal length of the ultrasound probe 200. In this case, it is necessary to match the central point of the curvature of the emitting surface of the ultrasound probe 200 with the central point of the curvature of the reflecting surface of the test object. In this case as well, according to this embodiment, it suffices if reference values are set for the times TR, TM, and TL, respectively, to satisfy the above condition and navigation is performed so as to match the times TR, TM, and TL with the respective reference values.

The transmitting unit 104 and receiving unit 105 each may be designed to have a 1-channel arrangement by using a matrix switch with a multiplexer arrangement. This makes it possible to reduce the circuit sizes of the transmitting unit 104 and receiving unit 105.

Display operation based on a signal generated by the display processing unit 109 may be performed by the display unit 112d. In this case, the display processing unit 109 is connected to the image generating unit 112b. The image generating unit 112b generates display data from the signal generated by the display processing unit 109. The display data is written in the memory unit 112c.

This apparatus may be realized as an ultrasound probe diagnosing apparatus by omitting the medical diagnosing unit 112.

Second and Third Embodiments

FIG. 15 is a block diagram showing the arrangement of an ultrasound diagnostic apparatus having a function of diagnosing an ultrasound probe according to the second and third embodiments.

This ultrasound diagnostic apparatus includes a main unit 400 and ultrasound probe 200.

The main unit 400 includes connectors 401, 402, and 403, a transmitting unit 404, a receiving unit 405, a measuring unit 406, a storage medium 407, an interface unit 408, a display processing unit 409, a control unit 410, and a medical diagnosing unit 411.

The connector 201 provided in the ultrasound probe 200 to be diagnosed is attached to a connector 401. The connector 401 has contacts 401a equal in number to contacts 201a provided on the connector 201. The contacts 401a are so arranged as to come into contact with the contacts 201a, respectively, when the connector 201 is attached to the connector 401. An external device (not shown) is connected to the connector 402 through a communication cable (not shown) such as a USB cable. This external device is, for example, a printer, network, personal computer, keyboard, and pointing device. A monitor device (not shown) is connected to the connector 403 through a monitor cable (not shown).

The transmitting unit 404 transmits excitation signals for exciting ultrasound transducing elements 202a. The transmitting unit 404 can transmit excitation signals for the respective ultrasound transducing elements 202a in parallel. The receiving unit 405 receives the signals received by the ultrasound transducing elements 202a. The receiving unit 405 can receive the signals received by the respective ultrasound transducing elements 202a in parallel. The receiving unit 405 holds reception signals sequentially received by repetitive transmission/reception performed for each ultrasound transducing element 202a, and adds them together. The receiving unit 405 outputs the reception signals or a signal obtained by the above addition (to be referred to as a composite signal hereinafter).

The measuring unit 406 measures the feature value of the composite signal output from the receiving unit 405. The measuring unit 406 outputs measurement information indicating the feature value obtained by the above measurement processing to the storage medium 407, interface unit 408, display processing unit 409, or control unit 410 under the control of the control unit 410. The storage medium 407 is, for example, a semiconductor memory. The storage medium 407 stores various kinds of information such as the above measurement information. The interface unit 408 performs communication processing conforming to, for example, the USB standard to realize communication with the external device connected to the connector 402. The display processing unit 409 generates an image signal for causing the monitor device connected to the connector 403 to display an image on the basis of the above measurement information, information supplied from the control unit 410, and the like.

The control unit 410 comprises, for example, a microprocessor. The control unit 410 systematically controls the respective units of the main unit 400 to realize operation for the diagnosis of the ultrasound probe 200. The control unit 410 also has a function of determining the focal length of the ultrasound probe 200. The control unit 410 has a function of variably setting the repetition period of transmission/reception of ultrasound waves. The control unit 410 has a function of controlling the transmitting unit 404 to transmit ultrasound signals to the ultrasound probe 200 in a transmission interval starting from each period set as described above. In addition, the control unit 410 has a function of diagnosing the ultrasound probe 200 on the basis of the measurement information obtained by the measuring unit 406, e.g., the feature value of the composite signal.

The medical diagnosing unit 411 also includes an imaging control unit 411a, image generating unit 411b, memory unit 411c, and display unit 411d. The imaging control unit 411a controls the transmitting unit 404, receiving unit 405, and image generating unit 411b so as to perform proper imaging processing in accordance with diagnosis contents or the like. The image generating unit 411b generates display data for displaying an image for medical diagnosis on the basis of the signals output from the receiving unit 405. The image represented by display data includes, for example, a reconstructed image such as a tomographic image or three-dimensional image concerning an organ or blood flow in a subject to be examined or a text image or graph representing a measurement value such as a blood flow rate or its change. The memory unit 411c stores the above display data. The display unit 411d performs display operation based on the display data.

The above arrangement is common to the second and third embodiments. The second and third embodiments differ in the contents of processing performed by the control unit 410 as will be described below concerning the following operation.

Second Embodiment

The operation of the ultrasound diagnostic apparatus according to the second embodiment will be described below.

When medical diagnosis on a subject to be examined is to be performed by using an ultrasound probe 200, information useful for medical diagnosis can be presented by activating a medical diagnosing unit 411 in the same manner as a known ultrasound diagnostic apparatus.

In diagnosing the ultrasound probe 200, a maintenance operator places a test object in a medium such as water in a vessel such as a water bath and also makes a head unit 202 face the test object in advance, as shown in FIG. 15. The maintenance operator adjusts the distance between the ultrasound probe 200 and the test object so as to position the reflecting surface of the test object at the focus point of the ultrasound probe 200.

If it is required to diagnose the ultrasound probe 200, a control unit 410 reads in the identification information output from an identification information output unit 204. The control unit 410 then acquires focus information concerning the model of the ultrasound probe 200. Subsequently, the control unit 410 acquires focus information concerning the model of the ultrasound probe 200. The model of the ultrasound probe 200 is determined on the basis of the above identification information. The identification information is information for specifying each ultrasound probe 200, and does not generally include information indicating a model. The control unit 410 determines the model of the ultrasound probe 200 by referring to a database in which pieces of model information are written in correspondence with various kinds of identification information. The database may be acquired in advance from the external device connected to a connector 402 or stored in advance in a storage medium 407. Alternatively, information indicating a model may be contained in identification information, and the control unit 410 may directly determine the model of the ultrasound probe 200 from this information. Focus information is information concerning the focus of the ultrasound probe 200, and indicates at least a focal length F. Focus information may be prepared for each ultrasound probe 200. In this case, focus information corresponding to the ultrasound probe 200 connected to a connector 401 may be acquired in accordance with identification information.

The control unit 410 determines a repetition period Tf on the basis of the focal length F indicated by the acquired focus information in the following manner. First of all, the control unit 410 calculates a time Ta required between transmitting an ultrasound signal from the ultrasound probe 200 and receiving the ultrasound signal reflected by the test object as $Ta=2F/C$ where C is the propagation velocity of an ultrasound wave in the medium in the vessel. The control unit 410 obtains the repetition period Tf as $Tf=ts+Ta+td$ where ts is the length of an interval during which an ultrasound wave is transmitted, and td is the time taken for the reflected ultrasound signal which has reached the ultrasound probe 200 to disappear.

The control unit 410 causes a transmitting unit 404 to excite an ultrasound transducing element 202a to transmit an ultrasound signal at the repetition period Tf determined in the above manner. As described above, the length of one ultrasound signal transmission interval is represented by ts. A reflected ultrasound signal from the test object is received by a receiving unit 405 through the above excited ultrasound transducing element 202a and a signal line 203a. The receiving unit 405 holds this reception signal for each period. Upon receiving signals throughout n periods (n is an arbitrary integer), the receiving unit 405 adds the reception signals corresponding to the n periods with reference to the transmission start timing of the ultrasound signal in each period. The receiving unit 405 then outputs the composite signal obtained by addition to a measuring unit 406. The measuring unit 406 then measures the feature value of the composite signal and generates measurement information indicating the feature value.

The control unit 410 diagnoses the ultrasound probe 200 on the basis of the above measurement information. The control unit 410 diagnoses whether, for example, the ultrasound probe 200 is normal. However, an item concerning the ultrasound probe 200 which is to be diagnosed may be arbitrary.

The repetition period Tf is determined in consideration of the focal length of the ultrasound probe 200 as described above. For this reason, when the ultrasound probe 200 with $2F/C=Ta1$ is connected to the connector 401 and when the ultrasound probe 200 with $2F/C=Ta2$ ($Ta2<Ta1$) is connected to the connector 401, repetition periods Tf1 and Tf2 are set, respectively, as shown in FIGS. 16A and 16B. In this case, since $Ta2<Ta1$, $Tf1<Tf2$. Each of the repetition periods Tf1 and Tf2 is set by adding a time Ts and time Td to a time Ta1 or Time Ta2, an ultrasound signal is transmitted immediately after the disappearance of the reflected ultrasound signal in either case.

According to the second embodiment, therefore, the idle time between the reception of a reflected ultrasound signal and the transmission of the next reflected ultrasound signal can be eliminated. This makes it possible to minimize the time corresponding to the n periods. As a consequence, the ultrasound probe 200 can be efficiently and quickly diagnosed.

Third Embodiment

The operation of an ultrasound diagnostic apparatus according to the third embodiment will be described below.

Conditions for diagnosis of an ultrasound probe 200 are set in the same manner as described in the second embodiment. A control unit 410 operates in the same manner as in the second embodiment up to the acquisition of focus information.

The control unit 410 determines repetition periods Tf1, Tf2, Tf3, . . . , Tfn on the basis of a focal length F indicated by acquired focus information in the following manner. First of all, the control unit 410 calculates a time Ta required between transmitting an ultrasound signal from the ultrasound probe 200 and receiving the ultrasound signal reflected by a test object as Ta=2F/C. The control unit 410 obtains a reference value Tf of the repetition period as Tf=ts+Ta+td. The control unit 410 obtains a repetition period Tfi (i=1, 2, 3, . . . , n) as Tfi=Tf+j×(i−1) where j is a constant. That is, the repetition period Tf1 is set to the reference value Tf, and Tf2, Tf3, . . . , Tfn are sequentially incremented by the constant j at a time.

Figure 17:
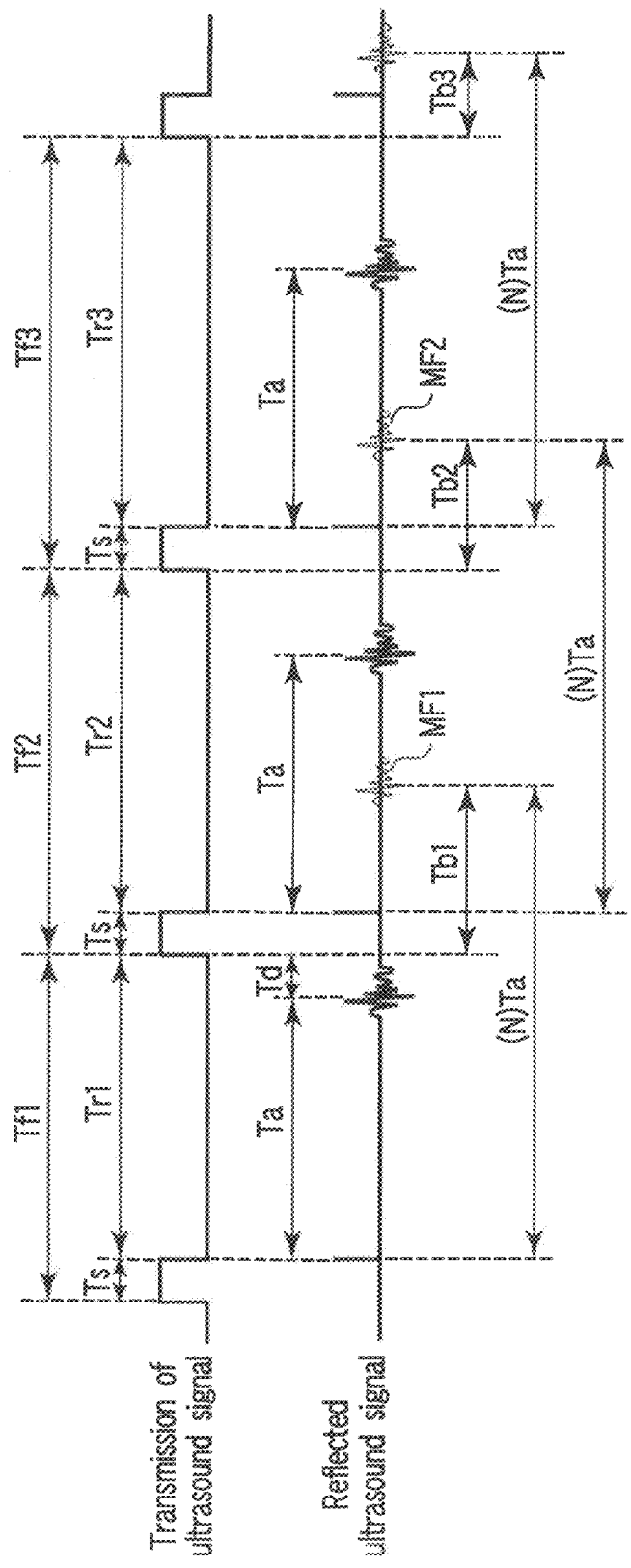
FIG. 17 is a timing chart showing how the repetition period is changed in the second embodiment.

The control unit 410 causes a transmitting unit 404 to excite ultrasound transducing elements 202a to repeatedly transmit ultrasound signals. As the repetition period of this ultrasound transmission, Tf1, Tf2, Tf3, . . . , Tfn determined in the above manner are sequentially used for each period. That is, as shown in FIG. 17, the first repetition period is set to Tf1, and the second repetition period is set to Tf2. Assume that the length of the transmission interval of one ultrasound signal is kept set to ts. Therefore, the lengths Tr1, Tr2, Tr3, . . . , Trn of a reception interval sequentially increase.

A receiving unit 405 receives a reflected ultrasound signal in a reception interval. The receiving unit 405 then obtains a composite signal by adding reception signals corresponding to n periods in the same manner as in the first embodiment.

Since the ultrasound probe 200 and test object are maintained in the state described above, a reflected ultrasound signal is supposed to reach the ultrasound probe 200 at a point of time when almost the time Ta has elapsed since the transmission of the ultrasound signal in each period. When a multiplex reflected signal is generated, the multiplex reflected signal reaches the ultrasound probe 200 at a point of time when an almost time (N)Ta has elapsed since the transmission of the ultrasound signal in each period. If the time (N)Ta is larger than Tfi, the multiplex reflected signal reaches the ultrasound probe 200 in the subsequent period. In this case, a time Tbi between the start timing of the period in which the multiplex reflected signal is received and the reception of the multiplex reflected signal is obtained as (N)Ta−Tri. As shown in FIG. 17, a time Tb1 associated with a multiplex reflected signal MF1 of an ultrasound signal transmitted in the first period is given by (N)Ta−Tr1. A time Tb2 associated with a multiplex reflected signal MF2 of the ultrasound signal transmitted in the second period is given by (N)Ta−Tr2. Since times Tr1, Tr2, Tr3, . . . , Trn sequentially change, the times Tb1, Tb2, Tb3, . . . , Tbn also sequentially change. Therefore, the timing at which a multiplex reflected signal is received within one period changes for each period.

Figure 18:
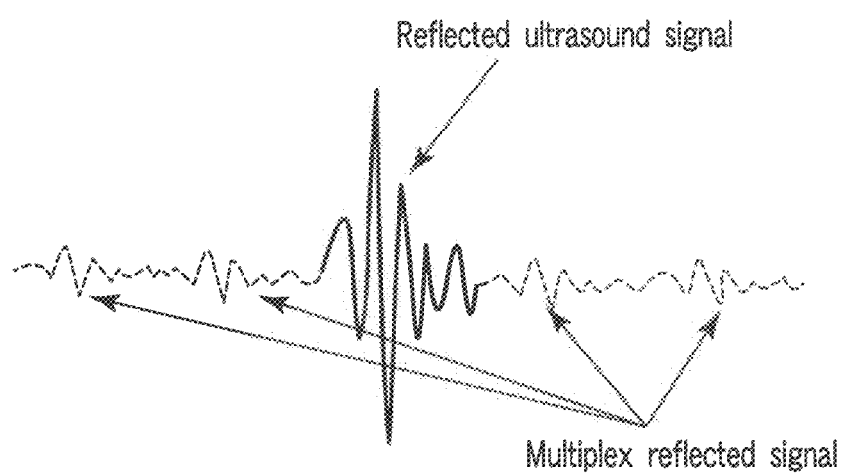
FIG. 18 is a view showing an example of a composite signal obtained by a receiving unit in FIG. 15 in the second embodiment.

When reception signals in the respective n periods are added together with reference to the transmission start timings of ultrasound signals in the respective periods, since the reflected signals are supposed to appear at the same timing, they are added together. As a consequence the level of the resultant signal increases by almost n times. However, multiplexed reflected signals appear discretely and hence are hardly added. As a result, the original reflected ultrasound signal components of the composite signal become sufficiently larger than the multiplex reflected signal components, as shown in FIG. 18.

As described above, according to the third embodiment, the reflected ultrasound signal component of a composite signal can be easily discriminated from the multiplex reflected signal components. Therefore, proper diagnosis can be performed, while the influences of multiplex reflected signals are reduced, by diagnosing the ultrasound probe 200 with attention being paid only to the feature amount of a composite signal associated with reflected ultrasound signal components.

According to the third embodiment, the minimum value of a repetition period is set in the same manner as in the second embodiment. For this reason, suppressing the repetition periods Tf1, Tf2, Tf3, Tfn to necessary minimum values makes it possible to efficiently and quickly perform diagnosis.

The second and third embodiments described above can be variously modified as follows.

The repetition period Tf in the second embodiment and the reference value Tf in the third embodiment may be determined with slight margins being added.

According to the second and third embodiments, a value input by the maintenance operator can be acquired as a focal length.

In the second or third embodiment, on the assumption that the distance between the ultrasound probe 200 and a test object is adjusted to coincide with the focal length of the ultrasound probe 200, a repetition period is determined with the focal length being regarded as the distance. However, the above distance need not always be matched with the focal length. If the distance is not set to coincide with the focal length, the distance should be determined, and a repetition period should be determined on the basis of the distance. If, for example, a distance is set for each ultrasound probe 200 or each type of ultrasound probe, a necessary distance may be acquired from a database or the like. Alternatively, a distance input by the maintenance operator can be acquired.

In the second or third embodiment, the ultrasound probe 200 may be diagnosed by referring to the feature amount measured for each signal without combining signals in a plurality of periods.

In the third embodiment, the minimum value of a repetition period may be set regardless of the focal length.

In the third embodiment, a repetition period can be changed in an arbitrary manner. For example, an increase in repetition period may be varied. Alternatively, a repetition period may be sequentially decreased or may be repeatedly increased and decreased.

In the second or third embodiment, the transmitting unit 404 and receiving unit 405 each may be designed to have a 1-channel arrangement by using a matrix switch with a multiplexer arrangement. This makes it possible to reduce the circuit sizes of the transmitting unit 404 and receiving unit 405.

Display operation based on a signal generated by a display processing unit 409 may be performed by a display unit 411d. In this case, the display processing unit 409 is connected to the image generating unit 411b. The image generating unit 411b generates display data from the signal generated by the display processing unit 409. The display data is written in the memory unit 411c.

This apparatus may be realized as an ultrasound probe diagnosing apparatus by omitting a medical diagnosing unit 411.

Fourth Embodiment

FIG. 19 is a block diagram showing the arrangement of an ultrasound diagnostic apparatus having a function of diagnosing an ultrasound probe according to the fourth embodiment. This ultrasound diagnostic apparatus includes a main unit 500 and ultrasound probe 600.

The main unit 500 includes connectors 501, 502, and 503, a transmitting unit 504, a receiving unit 505, a measuring unit 506, a storage medium 507, an interface unit 508, a display processing unit 509, a voltage generating unit 510, resistors 511-1 to 511-*n*, first switches 512-1 to 512-*n*, second switches 513-1 and 513-2, a control unit 514, and a medical diagnosing unit 515.

A connector provided on the ultrasound probe 600 to be diagnosed is attached to the connector 501. An external device (not shown) is connected to the connector 502 through a communication cable (not shown) such as a USB cable. This external device is, for example, a printer, network, personal computer, keyboard, and pointing device. A monitor device (not shown) is connected to the connector 503 through a monitor cable (not shown).

The transmitting unit 504 transmits excitation signals for exciting the ultrasound transducing elements provided for the ultrasound probe 600. The transmitting unit 504 can transmit excitation signals corresponding to many channels (n channels) in parallel. The receiving unit 505 receives signals output from the above ultrasound probe. The receiving unit 505 can receive n-channel signals in parallel. The receiving unit 505 outputs the received signals. The receiving unit 505 also has a function of detecting the voltages of signal lines which are provided for the ultrasound probe 600 to transmit n-channel signals. The receiving unit 505 outputs detected voltage V(CH) corresponding to the respective channels to the control unit 514.

The measuring unit 506 performs predetermined measurement processing on the basis of the reception signals output from the receiving unit 505. The measuring unit 506 outputs the measurement information obtained by the above measurement processing to the storage medium 507, interface unit 508, display processing unit 509, and control unit 514 under the control of the control unit 514. The storage medium 507 is, for example, a semiconductor memory. The storage medium 507 stores various kinds of information such as the above measurement information. The interface unit 508 performs communication processing conforming to, for example, the USB standard to realize communication with the external device connected to the connector 502. The display processing unit 509 generates an image signal for causing the monitor device connected to the connector 503 to display an image on the basis of the above measurement information, information supplied from the control unit 514, and the like.

The voltage generating unit 510 generates voltages Vsup1, ±Vsup2, and ±Vsup3 under the control of the control unit 514. The voltage generating unit 510 can outputs the voltages Vsup1 corresponding to the n channels in parallel. The voltage generating unit 510 can output the voltages +Vsup2, −Vsup2, +Vsup3, and −Vsup3, respectively, in parallel. The voltages Vsup1 are respectively applied to the B terminals of the first switches 512-1 to 512-*n*. The n-channel excitation signals output from the transmitting unit 504 are respectively supplied to the A terminals of the first switches 512-1 to 512-*n*. The first switches 512-1 to 512-*n* select these excitation signals and voltages Vsup1 and output them to the connector 501 under the control of the control unit 514. The voltages ±Vsup2 are applied to the C terminals of the second switches 513-1 and 513-2. The voltages ±Vsup3 are applied to the D terminals of the second switches 513-1 and 513-2. The second switches 513-1 and 513-2 select and output the voltages ±Vsup2 and ±Vsup3 to the connector 501 under the control of the control unit 514.

The control unit 514 comprises, for example, a microprocessor. The control unit 514 systematically controls the respective units of the main unit 500 to realize operation for the diagnosis of the ultrasound probe 600. The control unit 514 also has a function of determining the state of a signal line associated with each channel on the basis of the voltage V(CH) output from the receiving unit 505. The control unit 514 further has a function of acquiring the identification information of the ultrasound probe connected to the connector 501 through the connector 501, and identifying the type of the ultrasound probe 600. In addition, the control unit 514 has a function of controlling the operation states of the receiving unit 505, voltage generating unit 510, first switches 512-1 to 512-*n*, and second switches 513-1 and 513-2 in accordance with the identified type.

The medical diagnosing unit 515 further includes an imaging control unit 515*a*, image generating unit 515*b*, memory unit 515*c*, and display unit 515*d*. The imaging control unit 515*a* controls the transmitting unit 504, receiving unit 505, and image generating unit 515*b* to perform appropriate imaging processing in accordance with diagnosis contents or the like. The image generating unit 515*b* generates display data for displaying an image for medical diagnosis on the basis of the signals output from the receiving unit 505. The image represented by display data includes, for example, a reconstructed image such as a tomographic image or three-dimensional image concerning an organ or blood flow in a subject to be examined or a text image or graph representing a measurement value such as a blood flow rate or its change. The memory unit 515*c* stores the above display data. The display unit 515*d* performs display operation based on the display data.

The operation of the ultrasound diagnostic apparatus having the above arrangement will be described next.

When medical diagnosis on a subject to be examined is performed by using the ultrasound probe 600, activating the medical diagnosing unit 515 makes it possible to present information useful for medical diagnosis as in a known ultrasound diagnostic apparatus.

In diagnosing ultrasound probes 600, the ultrasound probes 600 of three types, i.e., the first to third types (to be referred to as probe types hereinafter), can be set as diagnosis targets. Note that in the following description, reference numerals 600-1 and 600-2 denote an ultrasound probe of the first type and an ultrasound probe of the second or third type, respectively, thereby discriminating them.

FIG. 20 is a view showing how the ultrasound probe 600-1 is connected to the connector 501 shown in FIG. 19. Note that in FIG. 20, an illustration of some of the constituent elements of the main unit 500 shown in FIG. 19 is omitted.

The ultrasound probe 600-1 includes a connector 601, head unit 602, cable unit 603, and identification information output unit 604.

The connector 601 is attached to the connector 501. The head unit 602 is formed by arraying n ultrasound transducing elements 602*a* at the maximum one-dimensionally or two-dimensionally. Each of the ultrasound transducing elements 602*a* is connected to the connector 601 through a signal line 603a provided in the cable unit 603. The connectors 501 and 601 connect signal lines 603a to the receiving unit 505 and first switches 512-1 to 512-n.

The identification information output unit 604 outputs identification information assigned to the ultrasound probe 600-1. The connectors 501 and 601 supply the identification information output from the identification information output unit 604 to the control unit 514.

Figure 21:
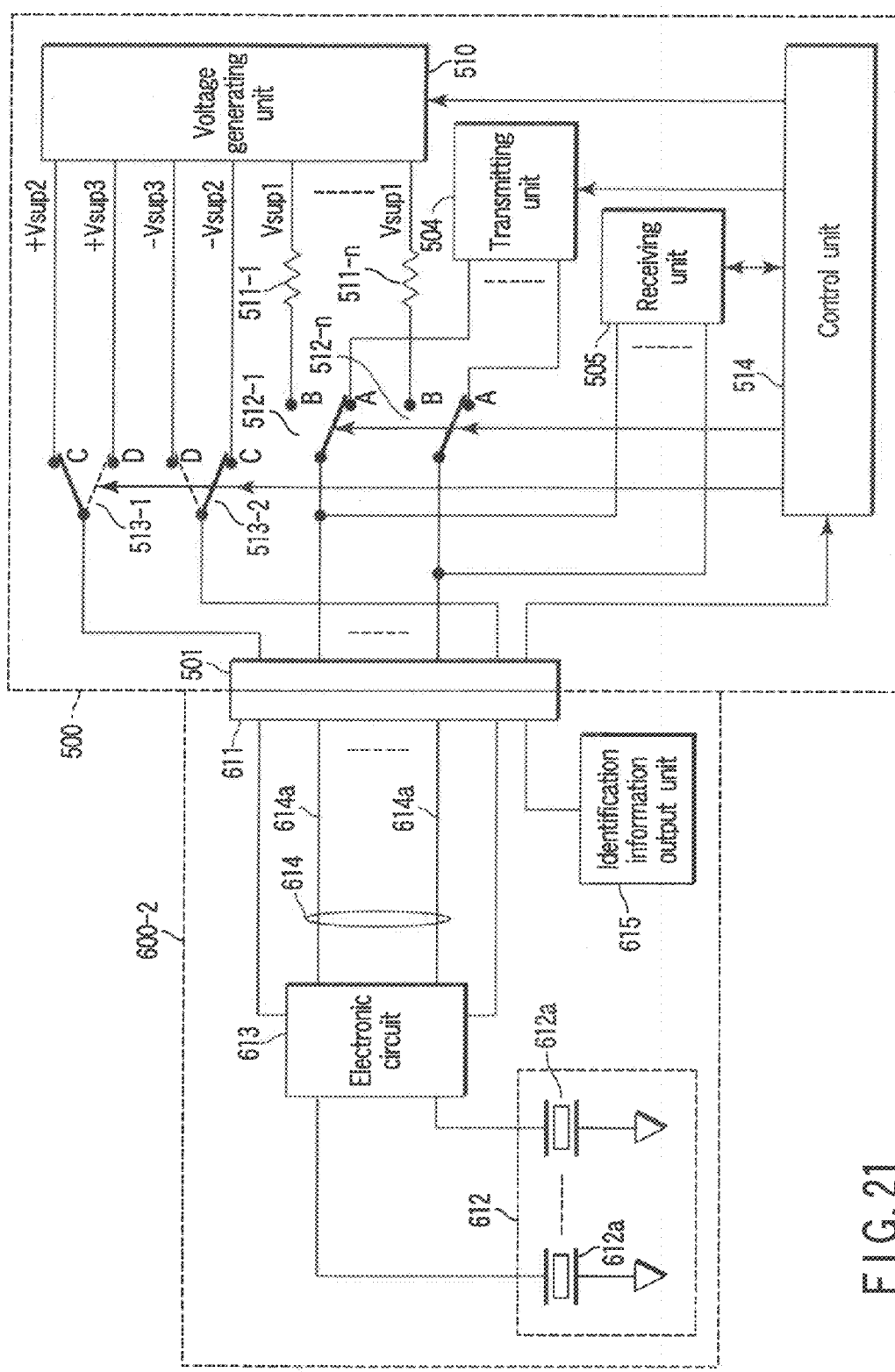
FIG. 21 is a view showing how an ultrasound probe of the second or third type is connected to the connector in FIG. 19.

FIG. 21 is a view showing how the ultrasound probe 600-2 is connected to the connector 501 shown in FIG. 19. Note that in FIG. 21, an illustration of some of the constituent elements of the main unit 500 shown in FIG. 19 is omitted.

The ultrasound probe 600-2 includes a connector 611, head unit 612, electronic circuit 613, cable unit 614, and identification information output unit 615.

The connector 611 is attached to the connector 501. The head unit 612 is formed by arraying n ultrasound transducing elements 612a at the maximum one-dimensionally or two-dimensionally. Each of the ultrasound transducing elements 612a is connected to the electronic circuit 613. The electronic circuit 613 is connected to the connector 611 through signal lines 614a equal in number to the ultrasound transducing elements 612a provided in the cable unit 614. The connectors 501 and 611 connect the signal lines 614a to the receiving unit 505 and first switches 512-1 to 512-n.

The identification information output unit 615 outputs identification information assigned to the ultrasound probe 600-2. The connector 501 and 611 supply the identification information output from the identification information output unit 615 to the control unit 514.

The electronic circuit 613 has a function of applying bias voltages to the signal lines 614a. In the second and third probe types, the electronic circuits 613 output different bias voltages. The electronic circuit 613 in the second probe type outputs a bias voltage equal to or higher than a voltage Vth upon reception of the voltage ±Vsup2. The electronic circuit 613 in the third probe type outputs a bias voltage less than the voltage Vth upon reception of the voltage ±Vsup2. However, upon reception of the voltage ±Vsup3, the electronic circuit 613 outputs a bias voltage equal to or higher than the voltage Vth. The connectors 501 and 611 connect third switches 513-1 and 513-2 to the voltage feed lines connected to the electronic circuit 613.

Figure 22:
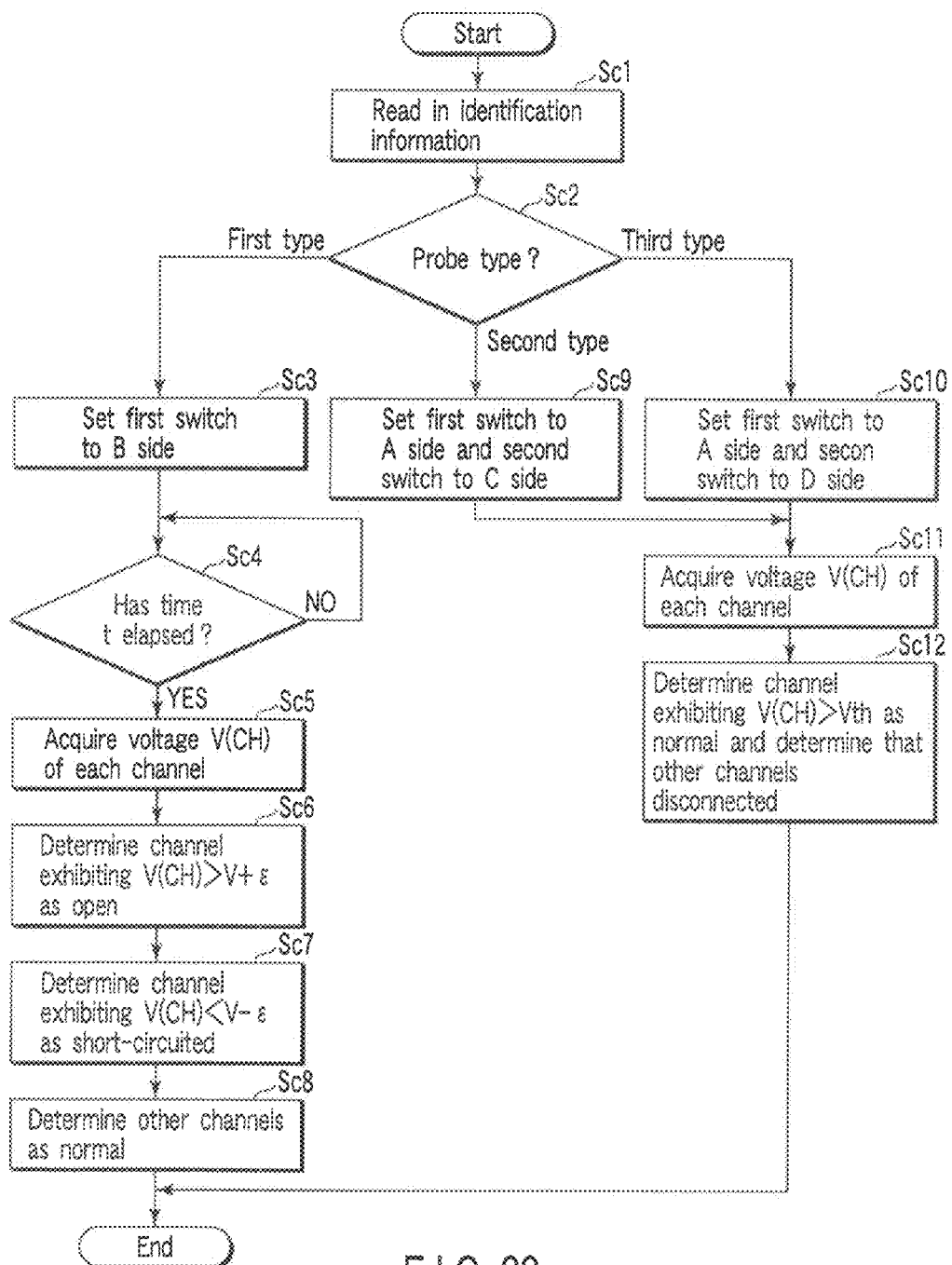
FIG. 22 is a flowchart showing a processing sequence executed by a control unit when the state of a signal line of the ultrasound probe connected to the connector in FIG. 19 is diagnosed.

If it is required to diagnose the states of signal lines connected to the ultrasound probe 600, the control unit 514 executes processing like that shown in FIG. 22.

In step Sc1, the control unit 514 reads in the identification information output from the identification information output unit 604 or identification information output unit 615. In step Sc2, the control unit 514 determines the probe type of the ultrasound probe 600 on the basis of the above identification information. The identification information is information which specifies each ultrasound probe but does not contain information indicating a probe type. The control unit 514 determines a probe type by referring to a database in which probe types are written in correspondence with various kinds of identification information. The database may be acquired in advance from the external device connected to the connector 502 or may be stored in the storage medium 507 in advance. Alternatively, information indicating a probe type may be contained in identification information, and a probe type may be directly determined from this information.

If the probe type is the first type, the control unit 514 advances from step Sc2 to step Sc3. In step Sc3, the control unit 514 causes the first switches 512-1 to 512-n to select the B-terminal sides, as shown in FIG. 20. Note that the first switches 512-1 to 512-n normally select the A-terminal sides. Therefore, the application of the voltage Vsup1 to each signal line 603a is started.

Figure 23:
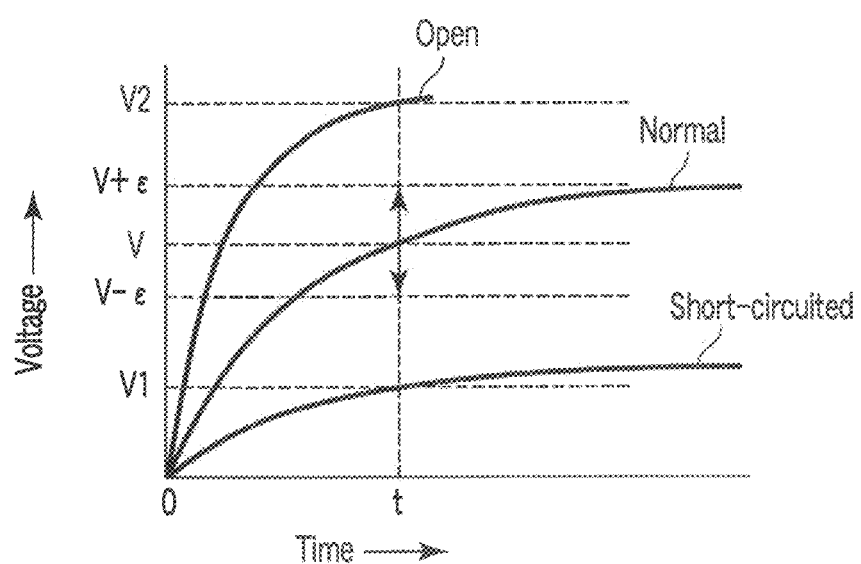
FIG. 23 is a graph showing how the voltage of a signal line changes after the start of application of a voltage to the signal line.

The voltage of the signal line 603a does not immediately reach the voltage Vsup1 but gradually rises. This is because a capacitive load component exists when the head unit 602 is viewed from the connector 601. The voltage of the signal line 603a at time t, with reference to the time when the application of a voltage to the signal line 603a starts, changes in accordance with the state of the signal line 603a, as shown in FIG. 23. Letting V be the voltage of the signal line 603a at time t when the signal line 603a is normal, the voltage of the signal line 603a at time t when the signal line 603a is short-circuited becomes V1 lower than V, and the voltage of the signal line 603a at time t when the signal line 603a is in the open state becomes V2 higher than V.

In step Sc4, the control unit 514 waits for a time t after the first switches 512-1 to 512-n are switched in step Sc3, and acquires the voltage of each signal line 603a at time t, i.e., a voltage V(CH) of each channel, from the receiving unit 505 in step Sc5. In step Sc6, the control unit 514 determines that any channel whose voltage V(CH) is higher than the value obtained by adding an allowable error $\epsilon$ to the voltage V is in the open state. In step Sc7, the control unit 514 determines that any channel whose voltage V(CH) is lower than the value obtained by subtracting the allowable error $\epsilon$ from the voltage V is short-circuited. In step Sc8, the control unit 514 determines that other channels, i.e., channels whose voltages V(CH) fall within the range of V±$\epsilon$, are normal.

Note that the proper values of time t, the voltage V, and the allowable error $\epsilon$ for the above determination vary depending on the type of ultrasound probe. If, therefore, values to be used as time t, the voltage V, and the allowable error $\epsilon$ are written in the above database in advance, and the values of time t, the voltage V, and the allowable error $\epsilon$ are acquired from the above database on the basis of the identification information read by the control unit 514 in step Sc1 and are used, the detection precision can be improved. In this case, the voltage generating unit 510 changes the voltage Vsup1 to be generated under the control of the control unit 514. Likewise, variable resistors may be used as the resistors 511-1 to 511-n, and their resistance values can be changed.

If the probe type is the second type, the control unit 514 advances from step Sc2 to step Sc9. In step Sc9, the control unit 514 causes the first switches 512-1 to 512-n to select the A-terminal sides, and also causes the second switches 513-1 and 513-2 to select the C-terminal sides, as indicated by the solid lines in FIG. 21. The control unit 514 then advances to step Sc1.

If the probe type is the third type, the control unit 514 advances from step Sc2 to step Sc10. In step Sc10, the control unit 514 causes the first switches 512-1 to 512-n to select the A-terminal sides, and also causes the second switches 513-1 and 513-2 to select the D-terminal sides, as indicated by broken lines in FIG. 21. The control unit 514 then advances to step Sc11.

In the ultrasound probe 600-2 of the third type, the electronic circuit 613 does not apply a bias voltage sufficient for detection to the signal line 614a unless the voltage ±Vsup3 different from the voltage ±Vsup2 is supplied, the voltage ±Vsup3 is applied to the electronic circuit 613 through the second switches 513-1 and 513-2. In contrast, in the ultrasound probe 600-2 of the second type, if the voltage ±Vsup2 is applied to the electronic circuit 613, the electronic circuit 613 applies a bias voltage sufficient for detection to the signal line 614a. Therefore, the voltage ±Vsup2 is applied to the electronic circuit 613 through the second switches 513-1 and 513-2.

In step Sc11, the control unit 514 acquires the voltage of each signal line 614a, i.e., the voltage V(CH) of each channel, from the receiving unit 505. In step Sc12, the control unit 514 determines that any channel whose voltage V(CH) is equal to or higher than a threshold Vth is normal, and other channels are broken.

Note that the values of the voltage ±Vsup2, voltage ±Vsup3, and threshold Vth suitable for the above determination vary depending on the type of ultrasound probe. If, therefore, values to be used as the voltage ±Vsup2, voltage ±Vsup3, and threshold Vth are written in the above database in advance, and the values of the voltage ±Vsup2, voltage ±Vsup3, and threshold Vth are acquired from the above database on the basis of the identification information read by the control unit 514 in step Sc1 and are used, the detection precision can be improved.

As described above, according to the fourth embodiment, if abnormality has occurred in the signal lines 603a and 614a or the connectors 601 and 611 of the ultrasound probes 600-1 and 600-2, the abnormality can be determined. This makes it possible to easily diagnose that a cause of malfunction of the ultrasound probes 600-1 and 600-2 resides in an ultrasound transducing element failure or a cable or connector failure.

The fourth embodiment also comprises a means for determining the state of each signal line by paying attention to the transient response characteristic of the voltage of the signal line and a means for determining the state of each signal line by paying attention to the bias voltage applied to the signal line, and selectively uses the two means depending on whether the diagnosis target connected to the connector 501 is the ultrasound probe 600-1 or the ultrasound probe 600-2 of the second or third type. In addition, in the fourth embodiment, the voltage ±Vsup2 and voltage ±Vsup3 can be selectively applied to the electronic circuit 613, and the voltage to be applied to the electronic circuit 613 is switched depending on whether the ultrasound probe 600-2 connected to the connector 501 is the second or third type. These make it possible to diagnose any types of ultrasound probes, i.e., any of the first to third types, and diagnose many types of ultrasound probes by using one main unit 500.

In the fourth embodiment, the probe type of the ultrasound probe 600 connected to the connector 501 is determined on the basis of the identification information of the ultrasound probe, and diagnosing operations are automatically switched in accordance with this determination. This makes it unnecessary for the operator to pay any attention to the probe type of the ultrasound probe 600 as a diagnosis target. Therefore, the load on the operator can be reduced.

The fourth embodiment can be variously modified as follows.

Although the fourth embodiment can diagnose the three probe types, i.e., the first to third types, the embodiment may be designed to diagnose only one or two probe types.

The ultrasound probe 600-1 may be diagnosed on the basis of the time required for the voltage of the signal line 603a to reach the voltage V.

The ultrasound probe 600-1 may be diagnosed to only determine whether the probe is normal.

The transmitting unit 504 and receiving unit 505 each may be designed to have a 1-channel arrangement by using a matrix switch with a multiplexer arrangement. This makes it possible to reduce the circuit sizes of the transmitting unit 504 and receiving unit 505. In addition, the voltage Vsup1 outputs of the voltage generating unit 510 can be integrated into one output, and the resistors 511 and first switches 512 can be integrated into one resistor and one first switch, respectively.

The applied state of the voltage Vsup1 can be changed in an arbitrary manner. For example, the voltage Vsup1 may be a negative voltage. The level of the already applied voltage Vsup1 may be raised or lowered. When the level of the voltage Vsup1 is to be changed, the polarity of the voltage Vsup1 may be kept unchanged or inversed.

Display operation based on a signal generated by the display processing unit 509 may be performed by the display unit 515d. In this case, the display processing unit 509 is connected to the image generating unit 515b. The image generating unit 515b generates display data from the signal generated by the display processing unit 509. The display data is written in the memory unit 515c.

This apparatus may be realized as an ultrasound probe diagnosing apparatus by omitting the medical diagnosing unit 515.

Fifth to Eighth Embodiments

A basic arrangement common to the fifth to eighth embodiments will be described first. FIG. 24 is a block diagram showing the basic arrangement of an ultrasound diagnostic apparatus having a function of diagnosing an ultrasound probe according to each embodiment.

This ultrasound diagnostic apparatus includes a main unit 700 and ultrasound probe 200.

The main unit 700 includes connectors 701, 702, and 703, a transmitting unit 704, a receiving unit 705, a measuring unit 706, a storage medium 707, an interface unit 708, a display processing unit 709, a determining unit 710, a control unit 711, and a medical diagnosing unit 712.

A connector 201 provided in the ultrasound probe 200 is attached to the connector 701. The connector 701 has contacts 701a equal in number to contacts 201a provided on the connector 201. Electrodes 701a are so arranged as to come into contact with the contacts 201a, respectively, when the connector 201 is attached to the connector 701. An external device (not shown) is connected to the connector 702 through a communication cable (not shown) such as a USB cable. This external device is, for example, a printer, network, personal computer, keyboard, and pointing device. A monitor device (not shown) is connected to the connector 703 through a monitor cable (not shown).

The transmitting unit 704 transmits excitation signals for exciting ultrasound transducing elements 202a. The transmitting unit 704 can transmit excitation signals for the respective ultrasound transducing elements 202a in parallel. The receiving unit 705 receives the signals received by the ultrasound transducing elements 202a. The receiving unit 705 can receive the signals received by the ultrasound transducing elements 202a in parallel. The receiving unit 705 outputs the received signals.

The measuring unit 706 measures the feature values of the signals output from the receiving unit 705. The measuring unit 706 outputs the measurement information obtained by the above measurement processing to the storage medium 707, interface unit 708, display processing unit 709, determining unit 710, or control unit 111 under the control of the control unit 711. The storage medium 707 is, for example, a semiconductor memory. The storage medium 707 stores various kinds of information such as the above measurement information. The interface unit 708 performs communication processing conforming to, for example, the USB standard to realize communication with the external device connected to the connector 702. The display processing unit 709 generates an image signal for causing the monitor device connected to the connector 703 to display an image on the basis of the above measurement information, information supplied from the control unit 711, and the like.

The determining unit 710 determines, on the basis of the measurement information output from the measuring unit 706 and data supplied from the storage medium 707 under the control of the control unit 711, whether the ultrasound probe 200 is normal. The determining unit 710 supplies the determination result to the control unit 711.

The control unit 711 comprises, for example, a microprocessor. The control unit 711 systematically controls the respective units of the main unit 700 to realize operation for the diagnosis of the ultrasound probe 200. The control unit 711 also has a function of sending data necessary for the above determination from the storage medium 707 to the determining unit 710 in synchronism with the determination processing performed by the determining unit 710.

The medical diagnosing unit 712 also includes an imaging control unit 712a, image generating unit 712b, memory unit 712c, and display unit 712d. The imaging control unit 712a controls the transmitting unit 704, receiving unit 705, and image generating unit 712b so as to perform proper imaging processing in accordance with diagnosis contents or the like. The image generating unit 712b generates display data for displaying an image for medical diagnosis on the basis of the signals output from the receiving unit 705. The image represented by display data includes, for example, a reconstructed image such as a tomographic image or three-dimensional image concerning an organ or blood flow in a subject to be examined or a text image or graph representing a measurement value such as a blood flow rate or its change. The memory unit 712c stores the above display data. The display unit 712d performs display operation based on the display data.

The above arrangement is the basic arrangement of the ultrasound diagnostic apparatus according to the fifth to eighth embodiments. The details of the fifth to eighth embodiments will be described below.

Fifth Embodiment

FIG. 25 is a block diagram showing the characteristic arrangement of a main unit 700 according to the fifth embodiment. The same reference numerals as in FIG. 24 denote the same parts in FIG. 25, and a detailed description thereof will be omitted.

As shown in FIG. 25, a measuring unit 706 includes a buffer memory 706a, amplitude analyzing unit 706b, center frequency analyzing unit 706c, and bandwidth analyzing unit 706d.

A receiving unit 705 outputs a received signal as a digital signal. The buffer memory 706a temporarily stores the digital signal output from the receiving unit 705. The amplitude analyzing unit 706b analyzes the digital signal stored in the buffer memory 706a, and measures the amplitude value and amplitude variation degree of the digital signal. The center frequency analyzing unit 706c analyzes the digital signal stored in the buffer memory 706a, and measures the center frequency value and frequency variation degree of the digital signal. The bandwidth analyzing unit 706d analyzes the digital signal stored in the buffer memory 706a, and measures the bandwidth value and bandwidth variation degree of the digital signal.

A determining unit 710 includes a V level determining unit 710a, Fo level determining unit 710b, BW level determining unit 710c, V variation determining unit 710d, Fo variation determining unit 710e, BW variation determining unit 710f, and comprehensive determining unit 710g. The storage medium 707 is provided with a reference database (reference DB) 707a.

The V level determining unit 710a performs quality determination on the basis of the amplitude value measured by the amplitude analyzing unit 706b and the level reference data for amplitude output from the reference database 707a. The Fo level determining unit 710b performs quality determination on the basis of the center frequency value measured by the center frequency analyzing unit 706c and the level reference data for center frequency output from the reference database 707a. The BW level determining unit 710c performs quality determination on the basis of the bandwidth value measured by the bandwidth analyzing unit 706d and the level reference data for bandwidth output from the reference database 707a.

The V variation determining unit 710d performs quality determination on the basis of the amplitude variation degree measured by the amplitude analyzing unit 706b and the variation reference data for amplitude output from the reference database 707a. The Fo variation determining unit 710e performs quality determination on the basis of the center frequency variation degree measured by the center frequency analyzing unit 706c and the variation reference data for center frequency output from the reference database 707a. The BW variation determining unit 710f performs quality determination on the basis of the bandwidth variation degree measured by the bandwidth analyzing unit 706d and the variation reference data for bandwidth output from the reference database 707a.

The comprehensive determining unit 710g comprehensively determines, on the basis of the quality determination results obtained by the V level determining unit 710a, Fo level determining unit 710b, BW level determining unit 710c, V variation determining unit 710d, Fo variation determining unit 710e, and BW variation determining unit 710f, whether the ultrasound probe 200 is normal.

FIG. 26 is a view showing the arrangement of the reference database 707a.

The reference database 707a includes a plurality of probe-specific reference databases (probe-specific reference DBs) 771. In the probe-specific reference databases 771, reference data determined in consideration of the characteristics of different types of ultrasound probes are written respectively. Each probe-specific reference database 771 includes a V reference database (V reference DB) 771a, Fo reference database (Fo reference DB) 771b, and BW reference database (BW reference DB) 771c.

As shown in FIG. 26, in the V reference database 771a, in correspondence with each channel of the ultrasound probe 200, level reference data for amplitude and variation reference data for quality determination concerning the corresponding channel are written in correspondence with the corresponding channel. In the Fo reference database 771b, as shown in FIG. 26, level reference data for center frequency and variation reference data for quality determination concerning the corresponding channel are written. In the BW reference database 771c, as shown in FIG. 26, level reference data for bandwidth and variation reference data for quality determination concerning the corresponding channel are written.

The operation of the ultrasound diagnostic apparatus according to the fifth embodiment having the above arrangement will be described next.

When medical diagnosis on a subject to be examined is performed by using the ultrasound probe 200, activating the medical diagnosing unit 712 makes it possible to present information useful for medical diagnosis as in a known ultrasound diagnostic apparatus.

In diagnosing the ultrasound probe 200, a maintenance operator places a test object in a medium such as water in a vessel such as a water bath and also makes a head unit 202 face the test object in advance, as shown in FIG. 24.

If it is required to diagnose the ultrasound probe 200, the control unit 711 causes the transmitting unit 704 to sequentially excite the ultrasound transducing elements 202a. The control unit 711 causes the receiving unit 705 to receive reflected ultrasound signals from the test object through the excited ultrasound transducing elements 202a, signal lines 203a, the contacts 201a, and the contacts 701a. As a consequence, the digital signals of the reflected ultrasound signals in the respective channels are sequentially stored in the buffer memory 706a. The control unit 711 causes the amplitude analyzing unit 706b to measure the amplitude values and amplitude variation degrees of the reflected ultrasound signals, causes the center frequency analyzing unit 706c to measure the center frequency values and center frequency variation degrees of the reflected ultrasound signals, and causes the bandwidth analyzing unit 706d to measure the bandwidth values and bandwidth variation degrees of the reflected ultrasound signals.

Figure 27A:
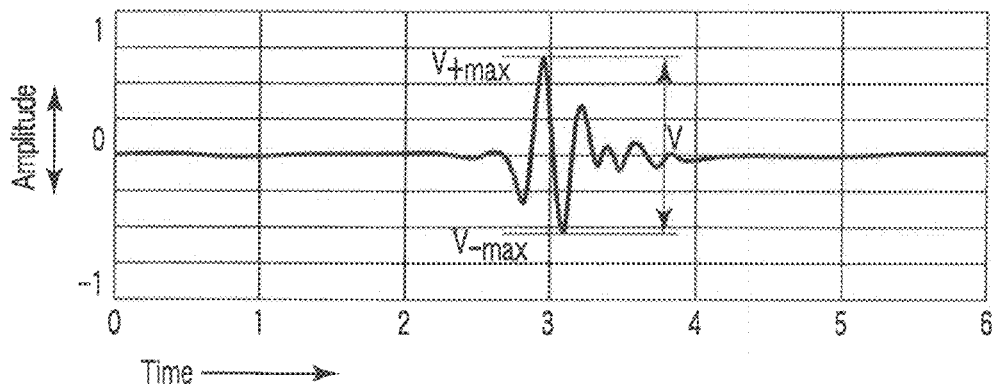
FIGS. 27A, 27B are graphs showing an example of a change in the amplitude of a reflected ultrasound signal and a frequency spectrum.

FIG. 27A is a graph showing an example of a change in the amplitude of a reflected ultrasound signal. The amplitude analyzing unit 706b sets the value of (V+max)+|(V−max)| or a larger one of the values of V+max and |(V−max)| in FIG. 27A as an amplitude value. The amplitude analyzing unit 706b sets the difference or ratio between the measured amplitude value and predetermined specified value as an amplitude variation degree.

Figure 27B:
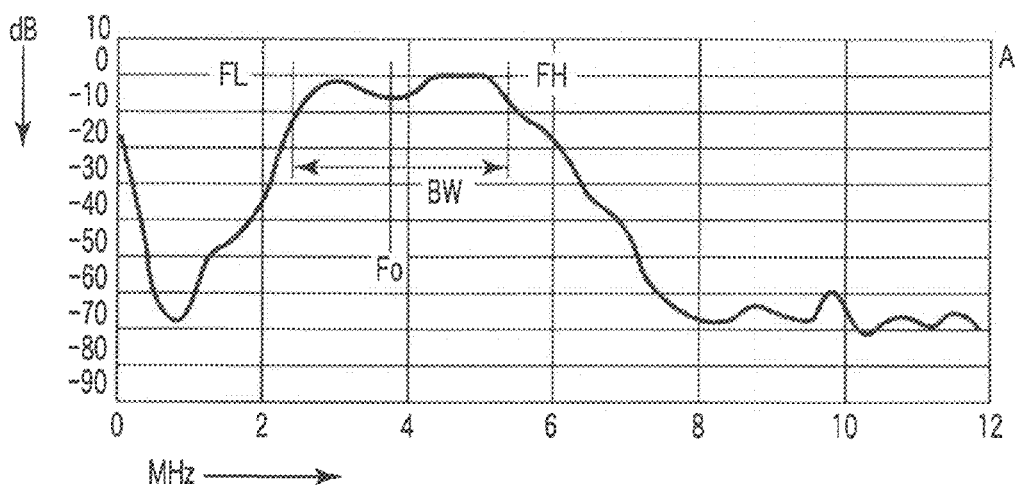

FIG. 27B is a graph showing an example of a frequency spectrum of a reflected ultrasound signal. The center frequency analyzing unit 706c sets (FL+FH)/2 in FIG. 27B as a center frequency value. The center frequency analyzing unit 706c also sets the difference or ratio between the measured center frequency value and the predetermined specified value as a center frequency variation degree. The bandwidth analyzing unit 706d sets (FH−FL) in FIG. 27B as a bandwidth value. The bandwidth analyzing unit 706d sets the difference or ratio between the bandwidth value and the predetermined specified value as a bandwidth variation degree.

The control unit 711 sends level reference data for amplitude, level reference data for center frequency, level reference data for bandwidth, variation reference data for amplitude, variation reference data for center frequency, and variation reference data for bandwidth which correspond to each channel from the reference database 707a to the V level determining unit 710a, Fo level determining unit 710b, BW level determining unit 710c, V variation determining unit 710d, Fo variation determining unit 710e, and BW variation determining unit 710f, respectively, in accordance with the timing at which an amplitude value, center frequency value, bandwidth value, amplitude variation degree, center frequency variation degree, and bandwidth variation degree are measured for each channel. Note that the control unit 711 determines the type of ultrasound probe 200 on the basis of the identification information output from an identification information output unit 204, and outputs each reference data from the probe-specific reference database 771 corresponding to the type of ultrasound probe 200.

Note that identification information is information which specifies each ultrasound probe 200 but does not generally include information indicating a model. The control unit 711 determines the model of the ultrasound probe 200 by referring to a database in which pieces of model information are written in correspondence with various kinds of identification information. The database may be acquired in advance from the external device connected to a connector 702 or stored in advance in the storage medium 707. Alternatively, information indicating a model may be contained in identification information, and the control unit 711 may directly determine the model of the ultrasound probe 200 from this information.

The V level determining unit 710a, Fo level determining unit 710b, and BW level determining unit 710c determine the quality of each channel depending on whether the amplitude value, center frequency value, and bandwidth value fall within the reference ranges indicated by the level reference data for amplitude, center frequency, and bandwidth, respectively. Each of the V level determining unit 710a, Fo level determining unit 710b, and BW level determining unit 710c output "PASS" as a determination result when a corresponding value falls within a corresponding reference range, and outputs "FAIL" as a determination result when a corresponding value falls outside a corresponding reference range. Note that level reference data for amplitude, center frequency, and bandwidth may indicate thresholds or allowable ranges. If the level reference data indicate thresholds, the V level determining unit 710a, Fo level determining unit 710b, and BW level determining unit 710c perform the above quality determination by comparing the thresholds with the respective values. If the level reference data indicate allowable ranges, these units perform the above quality determination by checking whether the respective values fall within the allowable ranges.

The V variation determining unit 710d, Fo variation determining unit 710e, and BW variation determining unit 710f determines the quality of each channel depending on whether the amplitude variation degree, center frequency variation degree, and bandwidth variation degree fall within the ranges indicated by the variation reference data for amplitude, center frequency, and bandwidth, respectively. Each of the V variation determining unit 710d, Fo variation determining unit 710e, and BW variation determining unit 710f outputs "PASS" as a determination result when each value falls within the corresponding reference range, and outputs "FAIL" when each value falls outside the corresponding reference range. Note that variation reference data for amplitude, center frequency, and bandwidth may indicate thresholds or allowable ranges. If the variation reference data indicate thresholds, the V variation determining unit 710d, Fo variation determining unit 710e, and BW variation determining unit 710f perform the above quality determination by comparing the thresholds with the respective variation degrees. If the variation reference data indicate allowable ranges, these units perform the above quality determination by checking whether the respective variation degrees fall within the allowable ranges.

The comprehensive determining unit 710g finally determines the quality of each channel on the basis of the respective determination results obtained by the V level determining unit 710a, Fo level determining unit 710b, BW level determining unit 710c, V variation determining unit 710d, Fo variation determining unit 710e, and BW variation determining unit 710f with respect to the same channel. The comprehensive determining unit 710g further determines the quality of the ultrasound probe 200 on the basis of quality determination results with respect to all the channels. The comprehensive determining unit 710g notifies the control unit 711 of the quality determination result concerning each channel and the quality determination result concerning the ultrasound probe 200.

The control unit 711 generates a display image indicating the quality determination result concerning each channel and the quality determination result concerning the ultrasound probe 200. A signal for causing the monitor device to display the display image is generated by a display processing unit 709 under the control of the control unit 711, and is output from a connector 703. The control unit 711 can generate the print data of a report containing the display image. This print data is sent to a printer through an interface unit 708 and the connector 702 and printed.

As described above, according to the fifth embodiment, the quality of the ultrasound probe 200, i.e., whether the ultrasound probe 200 is normal, is automatically determined. For quality determination, reference ranges corresponding to the types of ultrasound probes 200 are used. The above determination can therefore be properly performed in consideration of the characteristics of each type of ultrasound probe. The maintenance operator can easily and reliably recognize the necessity of maintenance for the ultrasound probe 200 by checking the determination result.

In addition, according to the fifth embodiment, quality determination is performed for each channel, and an individual reference range is used for this quality determination. This makes it possible to perform more appropriate determination considering also differences in characteristics between channels.

Furthermore, according to the fifth embodiment, since an amplitude value, center frequency value, and bandwidth value are used as feature values, appropriate determination can be performed by quality determination considering the characteristics of reflected ultrasound signals in many aspects.

Moreover, according to the fifth embodiment, quality determination is performed considering not only the feature value of a reflected ultrasound signal but also the variation degree of the feature value. This makes it possible to determine, as abnormal, a state wherein although each feature value falls within a corresponding reference range, variations in feature value are large.

Sixth Embodiment

FIG. 28 is a block diagram showing the characteristic arrangement of a main unit 700 according to the sixth embodiment. FIG. 28 shows only different points from the arrangement in the fifth embodiment, and the arrangement of the portion which is not shown is the same as in the fifth embodiment. The same reference numerals as in FIGS. 24 and 25 denote the same parts in FIG. 28, and a detailed description thereof will be omitted.

As shown in FIG. 28, a determining unit 710 includes a V level determining unit 710a, Fo level determining unit 710b, BW level determining unit 710c, V variation determining unit 710d, Fo variation determining unit 710e, BW variation determining unit 710f, and weighted determining unit 710h. A storage medium 707 is provided with a determination weight database (determination weight DB) 707b in addition to a reference database 707a.

Like the comprehensive determining unit 710g, the weighted determining unit 710h comprehensively determines, on the basis of the quality determination results obtained by the V level determining unit 710a, Fo level determining unit 710b, BW level determining unit 710c, V variation determining unit 710d, Fo variation determining unit 710e, and BW variation determining unit 710f, whether an ultrasound probe 200 is normal. Note, however, that the weighted determining unit 710h weights each determination result on the basis of the weighting data stored in the determination weight database 707b. The weighted determining unit 710h then performs the above comprehensive determination on the basis of each weighted determination result.

In the determination weight database 707b, weighting data indicating a weighting method for each determination result is written in correspondence with each type of ultrasound probe 200.

In the main unit 700 of the sixth embodiment having the above arrangement, weighting data corresponding to the type of ultrasound probe 200 is sent from the determination weight database 707b to the weighted determining unit 710h under the control of a control unit 711. The weighted determining unit 710h weights the quality determination results obtained by the V level determining unit 710a, Fo level determining unit 710b, BW level determining unit 710c, V variation determining unit 710d, Fo variation determining unit 710e, and BW variation determining unit 710f on the basis of the above weighting data, and finally determines the quality of each channel on the basis of the weighted determination results. In addition, the weighted determining unit 710h determines the quality of the ultrasound probe 200 on the basis of the quality determination results concerning all the channels. The weighted determining unit 710h notifies the control unit 711 of the quality determination result concerning each channel and the quality determination result concerning the ultrasound probe 200.

According to the sixth embodiment, the same effects as those of the fifth embodiment can be achieved. In addition, according to the sixth embodiment, when the influences of an amplitude value, center frequency value, bandwidth value, amplitude variation degree, center frequency variation degree, and bandwidth variation degree on the performance of the ultrasound probes 200 vary in degree depending on the types of ultrasound probes 200, more appropriate quality determination can be performed in consideration of this.

Seventh Embodiment

Figure 29:
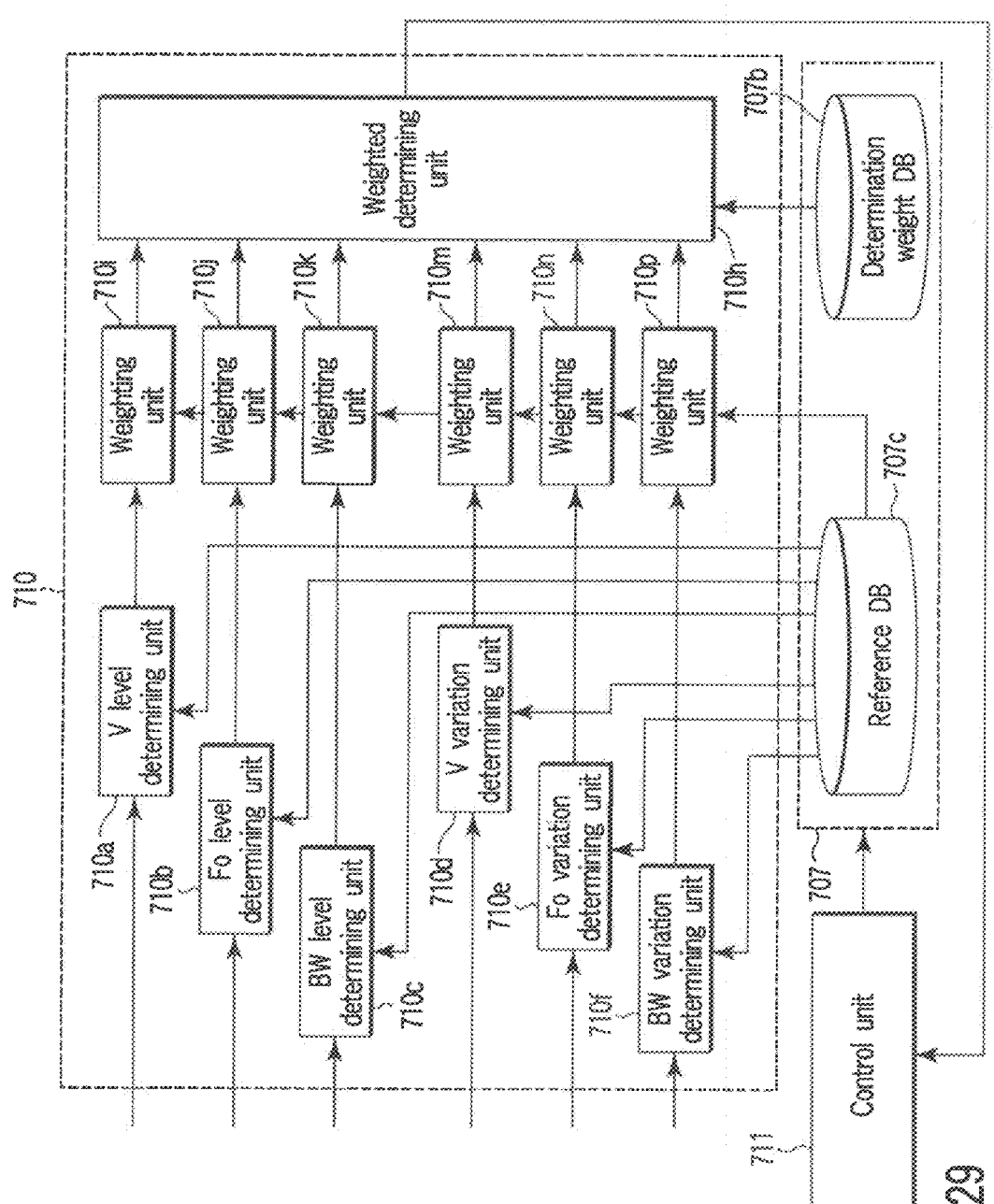
FIG. 29 is a block diagram showing the characteristic arrangement of an ultrasound diagnostic apparatus according to the seventh embodiment.

FIG. 29 is a block diagram showing the characteristic arrangement of a main unit 700 according to the seventh embodiment. FIG. 29 shows only different points from the arrangement in the fifth embodiment, and the arrangement of the portion which is not shown is the same as in the fifth embodiment. The same reference numerals as in FIGS. 24, 25, and 28 denote the same parts in FIG. 29, and a detailed description thereof will be omitted.

As shown in FIG. 29, a determining unit 710 includes weighting units 710i, 710j, 710k, 710m, 710n, and 710p in addition to a V level determining unit 710a, Fo level determining unit 710b, BW level determining unit 710c, V variation determining unit 710d, Fo variation determining unit 710e, BW variation determining unit 710f, and weighted determining unit 710h. The storage medium 707 is provided with a reference database 707c in addition to a determination weight database 707b.

The determination results obtained by the V level determining unit 710a, Fo level determining unit 710b, BW level determining unit 710c, V variation determining unit 710d, Fo variation determining unit 710e, and BW variation determining unit 710f are input to the weighting units 710i, 710j, 710k, 710m, 710n, and 710p, respectively. The weighting units 710i, 710j, 710k, 710m, 710n, and 710p weight the above input determination results on the basis of the weighting data stored in the reference database 707c. The respective determination results weighted by the weighting units 710i, 710j, 710k, 710m, 710n, and 710p are input to the weighted determining unit 710h.

Figure 30:
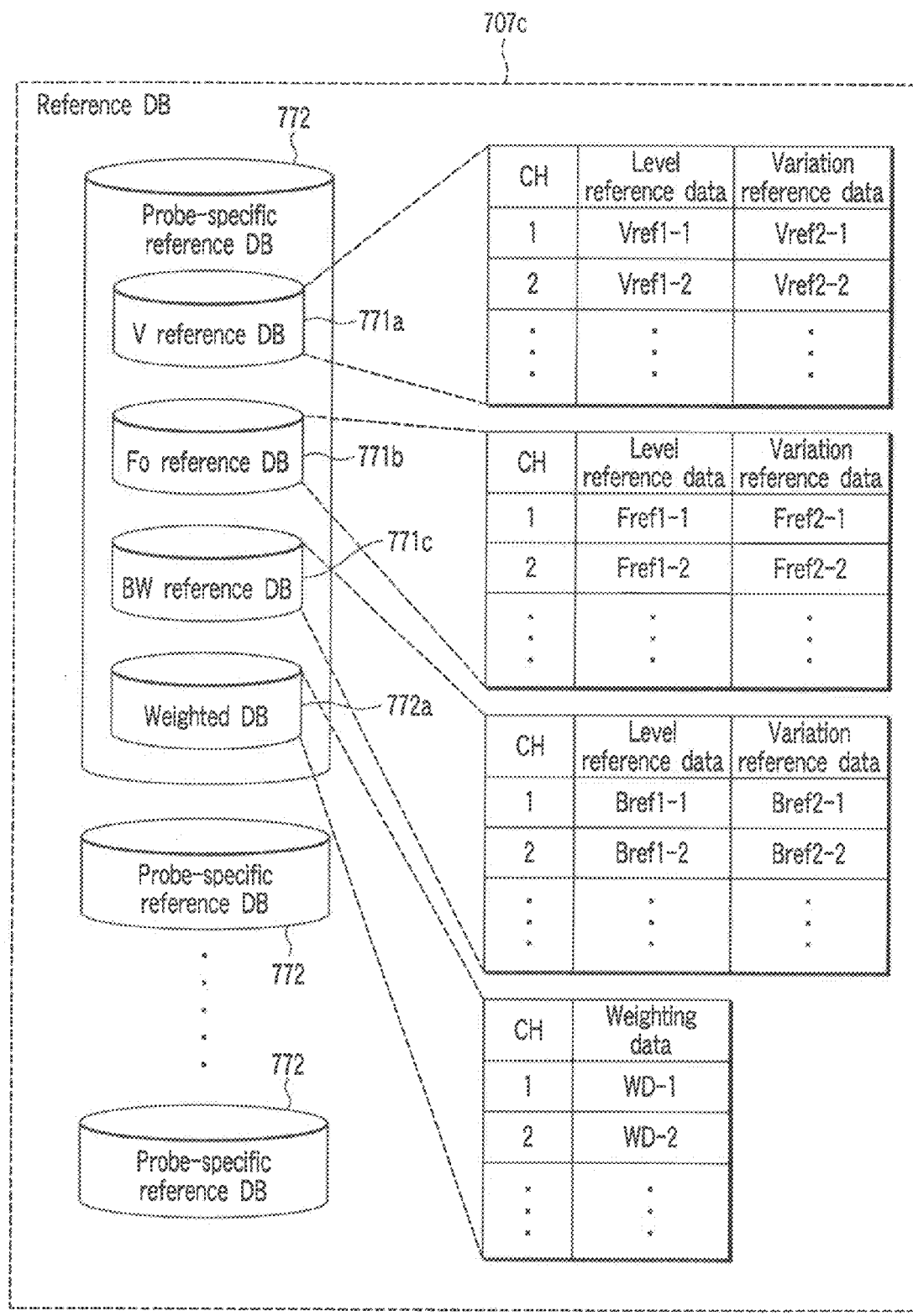
FIG. 30 is a view showing the arrangement of a reference database in FIG. 29.

FIG. 30 is a view showing the arrangement of the reference database 707c. The same reference numerals as in FIG. 26 denote the same parts in FIG. 30, and a detailed description thereof will be omitted.

The reference database 707c includes a plurality of probe-specific reference databases 772. In the probe-specific reference databases 772, reference data and weighting data which are set in consideration of the characteristics of different types of ultrasound probes are written. Each probe-specific reference database 772 includes a weighted database (weighted DB) 772a in addition to a V reference database 771a, Fo reference database 771b, and BW reference database 771c.

As shown in FIG. 30, in the weighted database 772a, weighting data concerning each channel is written in correspondence with each channel of the ultrasound probe 200. Weighting data indicates a weighting method set in consideration of differences in characteristics between channels.

In the main unit 700 of the seventh embodiment having the above arrangement, weighting data are sent from the reference database 707c to the weighting units 710i, 710j, 710k, 710m, 710n, and 710p under the control of a control unit 711. Note that the control unit 711 sends weighting data corresponding to each channel from the reference database 707c to the weighting units 710i, 710j, 710k, 710m, 710n, and 710p in accordance with the timing at which determination results concerning each channel are output from the V level determining unit 710a, Fo level determining unit 710b, BW level determining unit 710c, V variation determining unit 710d, Fo variation determining unit 710e, and BW variation determining unit 710f. The control unit 711 causes the probe-specific reference databases 772 to output weighting data in accordance with the types of ultrasound probes 200.

The weighting units 710i, 710j, 710k, 710m, 710n, and 710p weight the input determination results on the basis of the weighting data sent from the reference database 707c. With this operation, each determination result is weighted for each channel. Each determination result weighted in this manner is input to the weighted determining unit 710h, and final determination is performed in the same manner as in the sixth embodiment.

According to the seventh embodiment, the same effects as those of the fifth and sixth embodiments can be achieved. In addition, according to the seventh embodiment, since the determination results based on amplitude values, center frequency values, bandwidth values, amplitude variation degrees, center frequency variation degrees, and bandwidth variation degrees are weighted for each channel, more appropriate quality determination can be performed in consideration of differences in characteristics between channels.

Eighth Embodiment

Figure 31:
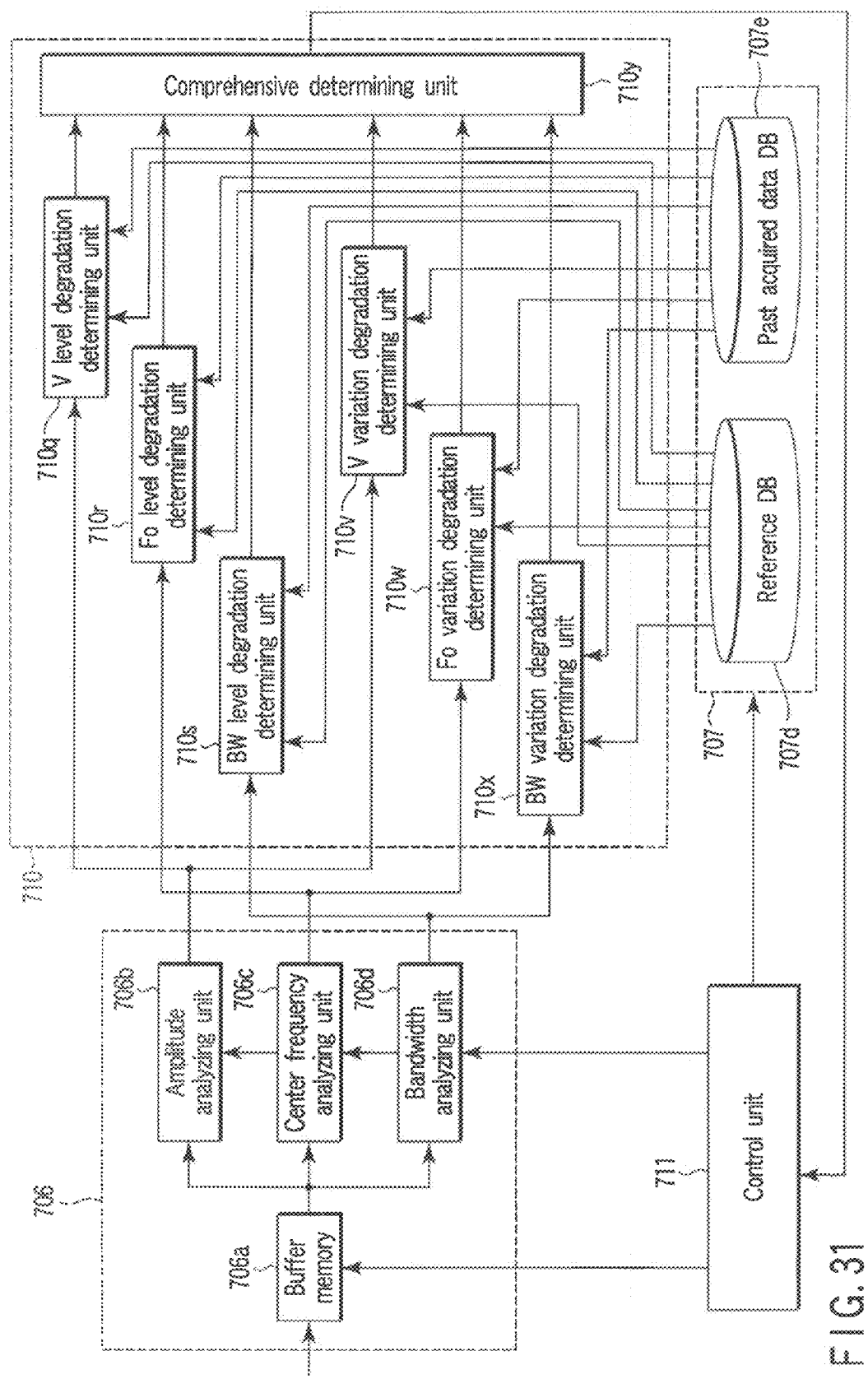
FIG. 31 is a block diagram showing the characteristic arrangement of an ultrasound diagnostic apparatus according to the eighth embodiment.

FIG. 31 is a block diagram showing the characteristic arrangement of a main unit 700 according to the eighth embodiment. FIG. 31 shows only different points from the arrangement in the fifth embodiment, and the arrangement of the portion which is not shown is the same as in the fifth embodiment. The same reference numerals as in FIGS. 24 and 25 denote the same parts in FIG. 31, and a detailed description thereof will be omitted.

As shown in FIG. 31, a determining unit 710 includes a V level degradation determining unit 710q, Fo level degradation determining unit 710r, BW level degradation determining unit 710s, V variation degradation determining unit 710v, Fo variation degradation determining unit 710w, BW variation degradation determining unit 710x, and comprehensive determining unit 710y. A storage medium 707 is provided with a reference database 707d and past acquired data database (past acquired data DB) 707e.

The V level degradation determining unit 710q obtains a degradation degree of an amplitude value (to be referred to as an amplitude degradation degree hereinafter) on the basis of the amplitude value newly measured by an amplitude analyzing unit 706b and the past measured amplitude value output from the past acquired data database 707e. The V level degradation determining unit 710q performs quality determination on the basis of the obtained amplitude degradation degree and the level degradation degree reference data for amplitude output from the reference database 707d. The Fo level degradation determining unit 710r obtains a degradation degree of a center frequency value (to be referred to as a center frequency degradation degree hereinafter) on the basis of the center frequency value newly measured by a center frequency analyzing unit 706c and the past measured center frequency value output from the past acquired data database 707e. The Fo level degradation determining unit 710r performs quality determination on the basis of the obtained center frequency degradation degree and the level degradation degree reference data for center frequency output from the reference database 707d. The BW level degradation determining unit 710s obtains a degradation degree of a bandwidth value (to be referred to as a bandwidth degradation degree hereinafter) on the basis of the bandwidth value newly measured by a bandwidth analyzing unit 706d and the past measured bandwidth value output from the past acquired data database 707e. The BW level degradation determining unit 710s performs quality determination on the basis of the obtained bandwidth degradation degree and the level degradation degree reference data for bandwidth output from the reference database 707d.

The V variation degradation determining unit 710v obtains a degradation degree of an amplitude variation (to be referred to as an amplitude variation degradation degree hereinafter) on the basis of the amplitude variation degree newly measured by the amplitude analyzing unit 706b and the past measured amplitude variation degree output from the past acquired data database 707e. The V variation degradation determining unit 710v performs quality determination on the basis of the obtained amplitude variation degradation degree and the variation degradation degree reference data for amplitude output from the reference database 707d. The Fo variation degradation determining unit 710w obtains a degradation degree of a center frequency variation (to be referred to as a center frequency variation degradation degree hereinafter) on the basis of the center frequency variation degree newly measured by the center frequency analyzing unit 706c and the past measured center frequency variation degree output from the past acquired data database 707e. The Fo variation degradation determining unit 710w performs quality determination on the basis of the obtained center frequency variation degradation degree and the variation degradation degree reference data for center frequency output from the reference database 707d. The BW variation degradation determining unit 710x obtains a degradation degree of a bandwidth variation (to be referred to as a bandwidth variation degradation degree hereinafter) on the basis of the bandwidth variation degree newly measured by the bandwidth analyzing unit 706d and the past measured bandwidth variation degree output from the past acquired data database 707e. The BW variation degradation determining unit 710x performs quality determination on the basis of the obtained bandwidth variation degradation degree and the variation degradation degree reference data for bandwidth output from the reference database 707d.

The comprehensive determining unit 710y comprehensively determines, on the basis of the quality determination results obtained by the V level degradation determining unit 710q, Fo level degradation determining unit 710r, BW level degradation determining unit 710s, V variation degradation determining unit 710v, Fo variation degradation determining unit 710w, and BW variation degradation determining unit 710x, whether the ultrasound probe 200 is normal.

The reference database 707d has an arrangement similar to that of the reference database 707a. In the reference database 707d, however, level degradation degree reference data are written instead of level reference data, and variation degradation degree reference data are written instead of variation reference data.

In the past acquired data database 707e, the amplitude values, amplitude variation degrees, center frequency values, center frequency variation degrees, bandwidth values, and bandwidth variation degrees measured in the past by the amplitude analyzing unit 706b, center frequency analyzing unit 706c, and bandwidth analyzing unit 706d are written as past measured amplitude values, past measured amplitude variation degrees, past measured center frequency values, past measured center frequency variation degrees, past measured bandwidth values, and past measured bandwidth variation degrees, respectively.

In the main unit 700 of the eighth embodiment having the above arrangement, an amplitude value degradation degree, center frequency value degradation degree, bandwidth degradation degree, amplitude variation degradation degree, center frequency degradation degree, and bandwidth degradation degree are obtained. The operation of the eighth embodiment differs from that of the fifth embodiment only in that quality determination on each channel is performed depending on whether each of the degradation degrees, instead of each feature value or its variation degree, falls within the reference range indicated by corresponding reference data.

The eighth embodiment can therefore achieve the same effects as those of the fifth embodiment.

The fifth to eighth embodiments described above can be variously modified as follows.

Normality or abnormality degrees may be ranked by indicating a plurality of reference ranges using reference data. For example, ranking normality degrees as shown in FIG. 32 allows the maintenance operator to recognize the degradation degree of the ultrasound probe 200 on the basis of this rank. This makes it possible to take some measures, e.g., preparing for future occurrence of abnormality.

Each reference value may be common to the respective channels.

Quality determination may be performed on the basis of only feature values without any consideration of variation degrees.

Only arbitrary one or two of an amplitude value, center frequency value, and bandwidth value may be set as a feature value or values to be considered. Alternatively, values other than those described above may be used.

A reference database 707a, a determination weight database 707b, a reference database 707c, and the reference database 707d or past acquired data database 707e may be prepared outside the main unit 700. In this case, each database is made accessible through, for example, a connector 702 in advance.

Level reference data and variation reference data may be written in different databases.

Display operation based on a signal generated by the display processing unit 709 may be performed by a display unit 712d. In this case, the display processing unit 709 is connected to the image generating unit 712b. The image generating unit 712b generates display data from the signal generated by the display processing unit 709. The display data is written in the memory unit 712c.

This apparatus may be realized as an ultrasound probe diagnosing apparatus by omitting a medical diagnosing unit 712.

Ninth Embodiment

FIG. 33 is a block diagram showing the arrangement of an ultrasound diagnostic apparatus having a function of diagnosing an ultrasound probe according to the ninth embodiment. This ultrasound diagnostic apparatus includes a main unit 800 and ultrasound probe 200.

As shown in FIG. 33, the main unit 800 includes connectors 801, 802, and 803, a transmitting unit 804, a receiving unit 805, a measuring unit 806, a storage medium 807, an interface unit 808, a display processing unit 809, a control unit 810, and a medical diagnosing unit 811.

A connector 201 provided in the ultrasound probe 200 to be diagnosed is attached to the connector 801. The connector 801 has contacts 801a equal in number to contacts 201a provided on the connector 201. The contacts 801a are so arranged as to come into contact with the contacts 201a, respectively, when the connector 201 is attached to the connector 801. An external device (not shown) is connected to the connector 802 through a communication cable (not shown) such as a USB cable. This external device is, for example, a printer, network, personal computer, keyboard, pointing device, and digital camera.

The transmitting unit 804 transmits excitation signals for exciting ultrasound transducing elements 202a. The transmitting unit 804 can transmit excitation signals for the respective ultrasound transducing elements 202a in parallel. The receiving unit 805 receives the signals output from the ultrasound transducing elements 202a. The receiving unit 805 can receive the signals output from the respective ultrasound transducing elements 202a in parallel. The receiving unit 805 outputs the received signals.

The measuring unit 806 performs predetermined measurement processing on the basis of the reception signals output from the receiving unit 805. The measuring unit 806 outputs the measurement information obtained by the above measurement processing to the storage medium 807, interface unit 808, display processing unit 809, and control unit 810 under the control of the control unit 810. The storage medium 807 is, for example, a semiconductor memory. The storage medium 807 stores various kinds of information such as the above measurement information. The interface unit 808 performs communication processing conforming to, for example, the USB standard to realize communication with the external device connected to the connector 802. The display processing unit 809 generates an image signal for causing the monitor device connected to the connector 803 to display an image on the basis of the above measurement information, information supplied from the control unit 810, and the like.

The control unit 810 comprises, for example, a microprocessor. The control unit 810 systematically controls the respective units of the main unit 800 to realize operation for the diagnosis of the ultrasound probe 200. The control unit 810 has a function of determining the electrical state of the ultrasound probe 200 on the basis of the voltage of each channel detected by the receiving unit 805 and the measurement result obtained by the measuring unit 806. The control unit 810 has a function of acquiring information indicating the quality of the appearance state of the ultrasound probe 200 by receiving designating operation by the maintenance operator. The control unit 810 has a function of acquiring digital photographic data from the external device connected to the connector 802. The control unit 810 has a function of generating report data indicating a report representing the electrical state determined by the above function, the information indicating the quality of the appearance state acquired by the above function, and the digital photograph acquired by the above function.

The medical diagnosing unit 811 also includes an imaging control unit 811a, image generating unit 811b, memory unit 811c, and display unit 811d. The imaging control unit 811a controls a transmitting unit 804, receiving unit 805, and image generating unit 811b so as to perform proper imaging processing in accordance with diagnosis contents or the like. The image generating unit 811b generates display data for displaying an image for medical diagnosis on the basis of the signals output from the receiving unit 805. The image represented by display data includes, for example, a reconstructed image such as a tomographic image or three-dimensional image concerning an organ or blood flow in a subject to be examined or a text image or graph representing a measurement value such as a blood flow rate or its change. The memory unit 811c stores the above display data. The display unit 811d performs display operation based on the display data.

The operation of the ultrasound diagnostic apparatus having the above arrangement will be described next.

When medical diagnosis on a subject to be examined is to be performed by using the ultrasound probe 200, information useful for medical diagnosis can be presented by activating the medical diagnosing unit 811 in the same manner as a known ultrasound diagnostic apparatus.

If it is required to diagnose the ultrasound probe 200, the control unit 810 reads in the identification information output from an identification information output unit 204. This identification information is information for specifying each ultrasound probe 200. The control unit 810 acquires probe information concerning the ultrasound probe 200 from a database on the basis of the above identification information. The database may be acquired in advance from the external device connected to the connector 802 or may be stored in advance in the storage medium 807. Probe information includes, for example, information concerning the user of the ultrasound probe 200 (e.g., a hospital name, customer site, section name, and address), the probe name of the ultrasound probe 200, outer appearance picture data of the ultrasound probe 200, and a maintenance contract number.

The control unit 810 executes processing for determining the electrical state of the ultrasound probe 200. The electrical state of the ultrasound probe 200 can be determined on the basis, for example, the state of a reflected ultrasound signal which can be received by using the ultrasound probe 200. More specifically, as shown in FIG. 33, a test object is placed in a medium such as water in a vessel such as a water bath, and ultrasound transducing elements 202a are excited. The receiving unit 805 receives reflected ultrasound signals from the test object through the ultrasound transducing elements 202a, signal lines 203a, the contacts 201a, and the contacts 801a, and causes the measuring unit 806 to measure various feature values concerning the reflected ultrasound signals (e.g., amplitude values, center frequency values, frequency band values, and group delay time values). The control unit 810 then determines the electrical state of the ultrasound probe 200 on the basis of the feature values measured by the measuring unit 806. The determination of this electrical state is, for example, quality determination on the reception quality of a reflected ultrasound signal, determination of whether the signal line 203a is broken, or comprehensive quality determination of the ultrasound probe 200 based on the above determining operations.

The control unit 810 prompts the maintenance operator to designate quality determination concerning several items associated with appearance states. In this embodiment, the maintenance operator is prompted to designate quality determination concerning the appearance states of the head unit (lens surface), case unit, capable unit, and connector unit. The maintenance operator visually checks the outer appearance of the ultrasound probe 200 to perform quality determination concerning each of the above items. Note that in performing quality determination of the head unit, the maintenance operator considers, for example, the occurrence of lens peeling/loosening, lens discoloration, lens expansion, lens gap, and lens indentation/flaws. In quality determination of the case unit, the maintenance operator considers, for example, fracture, contamination, flaws, and defects. In performing quality determination of the cable unit, the maintenance operator considers, for example, flaws, cladding peeling, contamination, and hardening. In performing quality determination of the connector unit, the maintenance operator considers, for example, bents in contact pins, terminal contamination, and defects. The control unit 810 acquires information indicating the quality of the appearance state of the ultrasound probe 200 by receiving the designation made by the maintenance operator. Note that since the designation of the appearance state is made by, for example, operating the keyboard, pointer, or the like connected to the connector 802, the control unit 810 receives information indicating this designating operation.

When the maintenance operator issues a request to capture a digital photograph, the control unit 810 can acquires digital photographic data from an external device such as a digital camera connected to the connector 802 through the connector 802 and interface unit 808.

Figure 34:
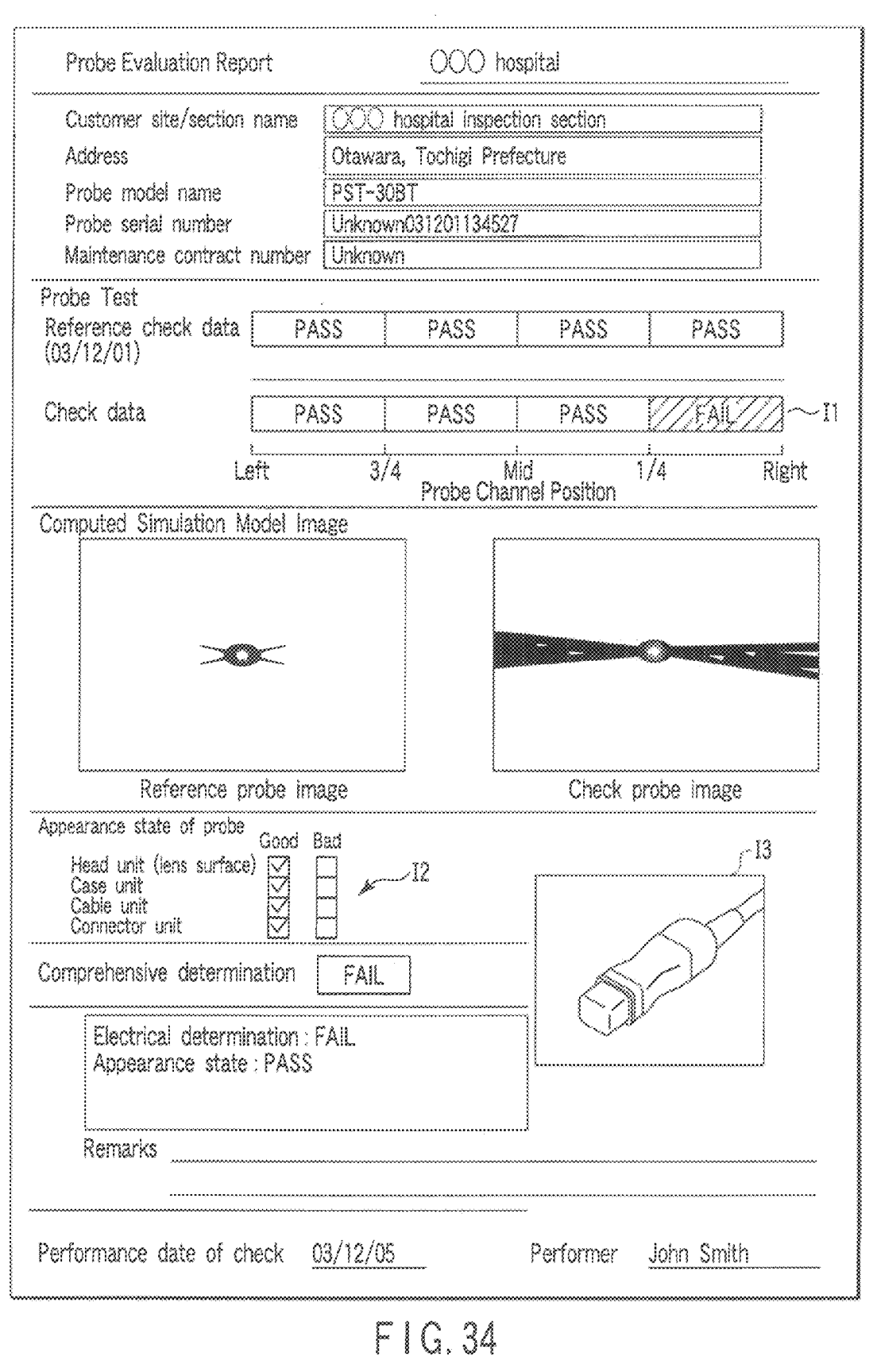

The control unit 810 generates report data indicating a report like that shown in FIG. 34 by using the above determination result concerning the electrical state, the acquired information indicating the quality of the appearance states, outer appearance picture data of the ultrasound probe 200, the acquired digital photographic data, and acquired probe information. This report data is output to the external device connected to the connector 802 through the interface unit 808. If, for example, the above report data is output to, for example, a printer connected as an external device to the connector 802, a report like that shown in FIG. 34 is printed by the printer. Referring to FIG. 34, an image I1 indicates a determination result concerning the electrical state; an image I2, the quality of appearance states; and an image I3, a outer appearance picture of the ultrasound probe 200. The image I3 may be replaced by a photograph obtained by the digital camera if the maintenance operator demands that the photograph be presented. In this case, the image I3 shows flaws, cladding peeling, contamination or the like, if any at the time of photographing. The photograph is therefore useful in diagnosing the ultrasound probe 200.

As described above, according to the ninth embodiment, a report indicating the electrical state of the ultrasound probe 200 and appearance states can be automatically generated. Using this report allows the maintenance operator to easily and properly report the owner or user. Since a outer appearance picture of the ultrasound probe 200 is presented, the maintenance operator can more easily know which ultrasound probe 200 is reported, than in the case where only the name of the ultrasound probe 200 is shown.

The ninth embodiment can be variously modified in as follows.

Figure 35:
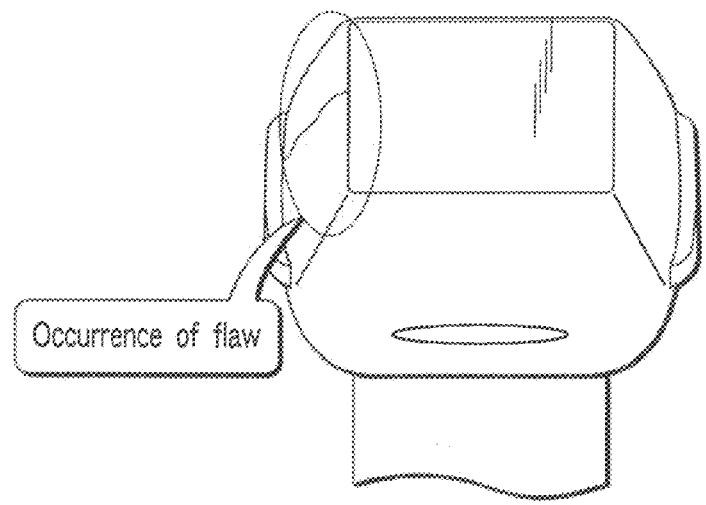
FIG. 35 is a view showing a modification of the image displayed on the report shown in FIG. 34.

For example, as shown in FIG. 35, a graphics image indicating an abnormality occurrence portion and abnormality contents may be generated by inputting the designations of the abnormality occurrence portion and abnormality contents in a digital photograph, and may be combined with the digital photograph to be presented in a report.

Either the quality of appearance states or a digital photograph may be presented alone in a report. Alternatively, another information such as a character string indicating a finding by the maintenance operator may be input to be presented in a report.

The transmitting unit 804 and receiving unit 805 each may be designed to have a 1-channel arrangement by using a matrix switch with a multiplexer arrangement. This makes it possible to reduce the circuit sizes of the transmitting unit 804 and receiving unit 805.

Various kinds of outer appearance information concerning various failure cases (listed cases in practice) concerning the head unit, case unit, cable unit, and connector unit are stored in the storage medium in association with probe information and appearance state determination information. Outer appearance information stored in the above storage medium may be acquired and presented by reading out the information by searching/specifying operation in accordance with the selection of probe information/appearance state determination by the maintenance operator. In practice, one or a plurality of pieces of representative failure outer appearance information concerning each of the head unit, case unit, cable unit, connector unit, and the like are stored in association with a probe information/determination item, and are read out (graphically processed as needed) in accordance with the probe information/determination item selected by the maintenance operator, thereby acquiring the corresponding outer appearance information. Note that a computer graphics image indicating an appearance state can be used as outer appearance information.

Display operation based on a signal generated by the display processing unit 809 may be performed by a display unit 811d. In this case, the display processing unit 809 is connected to the image generating unit 811b. The image generating unit 811b generates display data from the signal generated by the display processing unit 809. The display data is written in the memory unit 811c.

This apparatus may be realized as an ultrasound probe diagnosing apparatus by omitting a medical diagnosing unit 811.

10th Embodiment

FIG. 36 is a block diagram showing the arrangement of an ultrasound diagnostic apparatus having a function of diagnosing an ultrasound probe according to the 10th embodiment.

This ultrasound diagnostic apparatus includes a main unit 900 and ultrasound probe 200.

The main unit 900 includes connectors 901, 902, and 903, a transmitting unit 904, a receiving unit 905, a measuring unit 906, a storage medium 907, an interface unit 908, a display processing unit 909, a control unit 910, and a medical diagnosing unit 911.

A connector 201 is attached to the connector 901. The connector 901 has contacts 901a equal in number to contacts 201a provided on the connector 201. The contacts 901a are so arranged as to come into contact with the contacts 201a, respectively, when the connector 201 is attached to the connector 901. An external device (not shown) is connected to the connector 902 through a communication cable (not shown) such as a USB cable. This external device is, for example, a printer, network, personal computer, keyboard, and pointing device. A monitor device (not shown) is connected to the connector 903 through a monitor cable (not shown).

The transmitting unit 904 transmits excitation signals for exciting ultrasound transducing elements 202a. The transmitting unit 904 can transmit excitation signals for the respective ultrasound transducing elements 202a in parallel. The receiving unit 905 receives the signals output from the ultrasound transducing elements 202a. The receiving unit 905 can receive the signals output from the plurality of ultrasound transducing elements 202a in parallel. The receiving unit 905 outputs the received signals.

The measuring unit 906 performs predetermined measurement processing on the basis of the reception signals output from the receiving unit 905. The measuring unit 906 outputs the measurement information obtained by the above measurement processing to the storage medium 907, interface unit 908, display processing unit 909, and control unit 910 under the control of the control unit 910. The storage medium 907 is, for example, a semiconductor memory. The storage medium 907 stores various kinds of information such as the above measurement information. The interface unit 908 performs communication processing conforming to, for example, the USB standard to realize communication with the external device connected to the connector 902. The display processing unit 909 generates an image signal for causing the monitor device connected to the connector 903 to display an image on the basis of the above measurement information, information supplied from the control unit 910, and the like.

The control unit 910 comprises, for example, a microprocessor. The control unit 910 systematically controls the respective units of the ultrasound diagnostic apparatus 900 to realize operation for the diagnosis of the ultrasound probe 200. The control unit 910 has a function of diagnosing the state of each channel on the basis of the voltage of each channel detected by the receiving unit 905 and the measurement result obtained by the measuring unit 906. The control unit 910 also has a function of controlling the display processing unit 909 to generate display data for graphically displaying the positions of the contacts 201a in the connector 201 in correspondence with the above check results concerning channels including the contacts 201a.

The medical diagnosing unit 911 also includes an imaging control unit 911a, image generating unit 911b, memory unit 911c, and display unit 911d. The imaging control unit 911a controls the transmitting unit 904, receiving unit 905, and image generating unit 911b so as to perform proper imaging processing in accordance with diagnosis contents or the like. The image generating unit 911b generates display data for displaying an image for medical diagnosis on the basis of the signals output from the receiving unit 905. The image represented by display data includes, for example, a reconstructed image such as a tomographic image or three-dimensional image concerning an organ or blood flow in a subject to be examined or a text image or graph representing a measurement value such as a blood flow rate or its change. The memory unit 911c stores the above display data. The display unit 911d performs display operation based on the display data.

Figure 37:
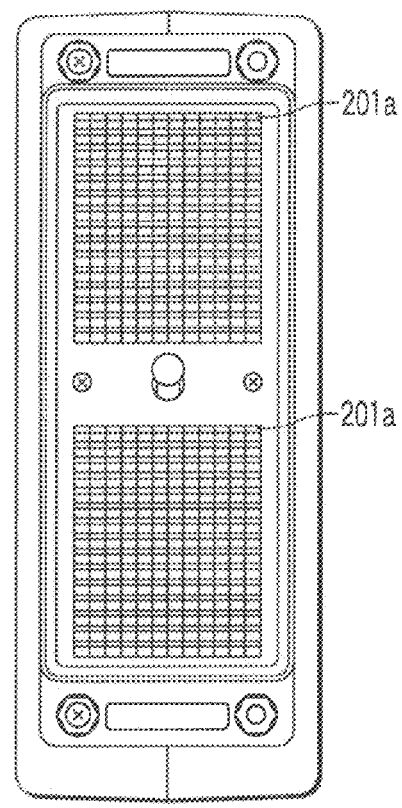
FIG. 37 is a view showing an example of the outer appearance of a connector in FIG. 36.

FIG. 37 is a view showing an example of the outer appearance of the connector 201 in FIG. 36. The connector 201 shown in FIG. 37 has many contacts 201a arranged in the form of a matrix. The connector 201 shown in FIG. 37 has a total of 360 contacts 201a, more specifically, two contact groups each having contacts arranged in a 15×12 matrix. Signal lines 203a are connected to some of the 360 contact 201a. If, for example, the ultrasound probe 200 has a 128-channel arrangement, 128 signal lines 203a are respectively connected to 128 contacts 201a. Other contacts 201a are connected to the identification information output unit 204 or to power supply lines and ground lines (none of which are shown in FIG. 36). There are a plurality of models of ultrasound probes 200, e.g., ultrasound probes having different numbers of channels. The connector 201 shown in FIG. 37 can be commonly used for these models. Therefore, which contacts of the 360 contacts are to be connected to the signal lines 203a varies depending on the model.

The operation of the ultrasound diagnostic apparatus having the above arrangement will be described next.

When medical diagnosis on a subject to be examined is to be performed by using the ultrasound probe 200, information useful for medical diagnosis can be presented by activating the medical diagnosing unit 911 in the same manner as a known ultrasound diagnostic apparatus.

If it is required to diagnose the state of each channel in the ultrasound probe 200, the control unit 910 determines to which one of the many contacts 201a of the connector 201 the channel whose state is to be diagnosed belongs. More specifically, the control unit 910 reads in the identification information output from the identification information output unit 204. The control unit 910 determines the model of the ultrasound probe 200 connected to the connector 901 on the basis of the above identification information. The identification information is information for specifying each ultrasound probe 200, and does not generally include information indicating a model. The control unit 910 determines the model of the ultrasound probe 200 by referring to a database in which pieces of model information are written in correspondence with various kinds of identification information. The database may be acquired in advance from the external device connected to the connector 902 or stored in advance in the storage medium 907. Alternatively, information indicating a model may be contained in identification information, and the control unit 910 may directly determine the model of the ultrasound probe 200 from this information. The control unit 910 determines the function of each contact 201a in the mode determined above by referring to the above database or another database. Note that when only the ultrasound probe 200 of the model in which the functions of the respective contacts 201a are the same is to be diagnosed, such processing can be omitted.

The control unit 910 diagnoses the state of each channel to be diagnosed which is determined in the above manner. A method of diagnosing the state of a channel may be arbitrary. For example, the state of each channel can be diagnosed on the basis of the state of a reflected ultrasound signal which can be received by using the channel. More specifically, as shown in FIG. 36, a test object is placed in a medium such as water in a vessel such as a water bath, and the ultrasound transducing elements 202a are excited. The receiving unit 905 receives reflected ultrasound signals from the test object through the ultrasound transducing elements 202a, signal lines 203a, the contacts 201a, and the contacts 901a, and causes the measuring unit 906 to collect various data concerning the reflected ultrasound signals. The control unit 910 then determines the state of each channel on the basis of the data collected by the measuring unit 906. Alternatively, the state of each channel can be diagnosed on the basis of the transient response characteristic of the voltage of the signal line 203a when a DC voltage is applied to the signal line 203a or the bias voltage output from an electronic circuit (not shown) provided for the ultrasound probe 200.

Upon completing diagnosis concerning all the channels whose states are to be diagnosed, the control unit 910 causes the display processing unit 909 to generate display data indicating this diagnosis result. The display data generated by the display processing unit 909 is sent to the monitor device through the connector 903. The monitor device displays the image indicating the diagnosis result on the basis of the above display data.

The ultrasound diagnostic apparatus 900 can display a diagnosis result by three display methods, i.e., the first to third display methods. Determining which one of the three display methods is to be used in accordance with designation by the user makes it possible to perform display operation in accordance with user's need.

Figures 38, 39:
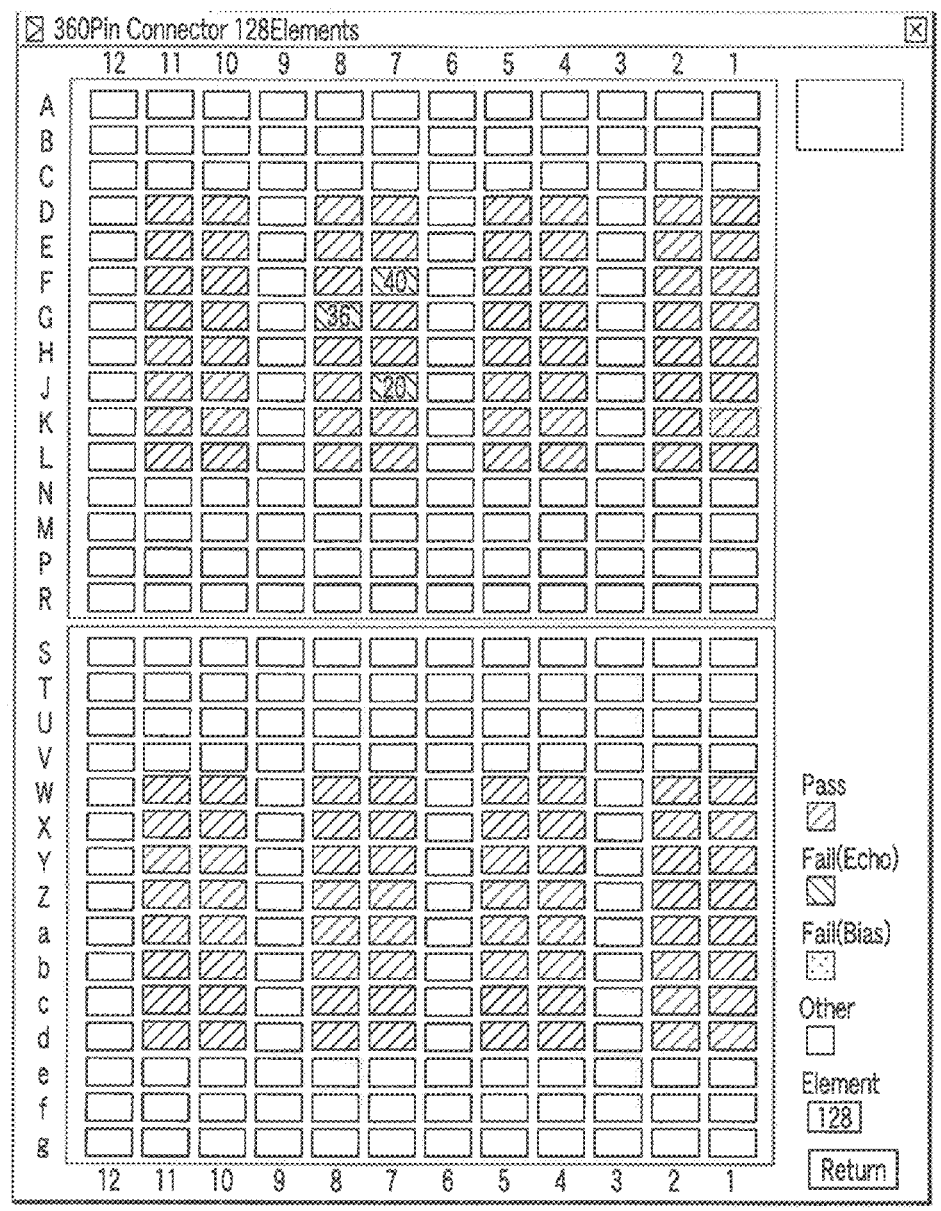
FIG. 38 is a view showing an example of an image displayed by the first display method.
FIG. 39 is a view showing an example of an image displayed by the second display method.

FIG. 38 is a view showing an example of the image displayed by the first display method.

The image shown in FIG. 38 is based on a computer graphics image indicating the arrangement pattern of the contacts 201a of the connector 201. A computer graphics image indicating diagnosis results concerning channels belonging to the contacts 201a arranged at the respective positions in the graphics image serving as this base is combined with the graphics image serving as the above base. Referring to FIG. 38, color differences are indicated by different kinds of hatchings. In the image shown in FIG. 38, at the position of the contact 201a to which a channel in which abnormality has been found belongs, a numeral indicating the corresponding channel number is combined.

FIG. 39 is a view showing an example of the image displayed by the second display method.

The image shown in FIG. 39 indicates, by using characters, pieces of connector location information indicating the positions of the contacts 201a of the connector 201 to which the respective channels belong and diagnosis results in correspondence with the respective channel numbers.

Connector location information comprises a combination of a row number assigned to each row of the matrix of the contacts 201a of the connector 201 and a column number assigned to each column. For example, the connector 201 shown in FIG. 37 has the contacts 201a arranged in a 30 (rows)×12 (columns) matrix, and the 30 rows are assigned A to Z and a to g as row numbers, and the 12 columns are assigned 1 to 12 as column numbers. In the case shown in FIG. 39, connector location information concerning the channel whose channel number is "1" is represented by "A-12". This indicates that the contact 201a belonging to the channel whose channel number is "1" is located at the Ath row and 12th column.

FIGS. 40a and 40B are views showing an example of the image displayed by the third display method.

The image shown in each of FIGS. 40A and 40B is based on an actual image I11 of the outer appearance of the connector 201 which is imaged to indicate the arrangement of the contacts 201a in the connector 201. In the initial state, only the actual image I11 described above and a pointer P are indicated, as shown in FIG. 40A.

In this state, the control unit 910 receives pointer operation by the user with, for example, the pointing device connected to the connector 902. The control unit 910 moves the pointer P in accordance with this pointer operation.

If the pointer P is moved to a position designating any one of the contacts on the actual image I11 as shown in FIG. 40B, the control unit 910 updates the image to display an image I12 indicating a diagnosis result concerning the channel belonging to the designated contact by combining it with the above image, as shown in FIG. 40B.

As described above, according to this embodiment, a diagnosis result concerning each channel is displayed in correspondence with the position of the corresponding contact 201a belonging to the channel in the connector 201. If, therefore, a failure has occurred in any of the channels, the maintenance operator can easily know, by only visual observation, to which one of the contacts 201a the channel belongs. It is easy to discriminate the signal line 203a connected to the specific contact 201a. It is also easy to discriminate the ultrasound transducing element 202a belonging to the same channel as that of the specific contact 201a by tracing the signal line 203a discriminated in this manner. As described above, the maintenance operator can easily discriminate the contact 201a, ultrasound transducing element 202a, and signal line 203a which constitute the channel in which abnormality has occurred. This makes it easy for the maintenance operator to recognize the portion in which the failure has occurred. Since this makes it possible to shorten the time required to recognize a failure occurrence portion, the time required to repair the ultrasound probe 200 can be shortened.

The 10th embodiment can be variously modified as follows.

Although a diagnosis result can be displayed by each of the three display methods, i.e., the first to third display methods, the embodiment may be designed to display the diagnosis result by only one or two display methods.

The base image in the first display method may be replaced with the actual image used in the third display method.

The base image in the third display method may be replaced with the computer graphics image as the base used in the first display method.

Information for presenting a diagnosis result may be generated by a presenting method other than the display methods. For example, print data for causing the printer to print an image like that described above may be generated. In this case, generating print data indicating the image obtained by combining the above image with a predetermined form for a report makes it possible to easily and automatically generate a report indicating diagnosis results so as to make them easy to understand as described above.

The transmitting unit 904 and receiving unit 905 each may be designed to have a 1-channel arrangement by using a matrix switch with a multiplexer arrangement. This makes it possible to reduce the circuit sizes of the transmitting unit 904 and receiving unit 905.

Display operation based on a signal generated by a display processing unit 909 may be performed by a display unit 911d. In this case, the display processing unit 909 is connected to the image generating unit 911b. The image generating unit 911b generates display data from the signal generated by the display processing unit 909. The display data is written in the memory unit 911c.

This apparatus may be realized as an ultrasound probe diagnosing apparatus by omitting a medical diagnosing unit 911.

11th Embodiment

FIG. 41 is a block diagram showing the arrangement of an ultrasound diagnostic apparatus having a function of diagnosing an ultrasound probe according to the 11th embodiment. This ultrasound diagnostic apparatus includes a main unit 1000 and ultrasound probe 200.

The main unit 1000 includes connectors 1001, 1002, and 1003, a transmitting unit 1004, a receiving unit 1005, a measuring unit 1006, a storage medium 1007, an interface unit 1008, a display processing unit 1009, an image simulation processing unit 1010, a control unit 1011, and a medical diagnosing unit 1012.

A connector 201 provided in the ultrasound probe 200 is attached to the connector 1001. The connector 1001 has contacts 1001a equal in number to contacts 201a provided on the connector 201. The contacts 1001a are so arranged as to come into contact with the contacts 201a, respectively, when the connector 201 is attached to the connector 1001. An external device (not shown) is connected to the connector 1002 through a communication cable (not shown) such as a USB cable. This external device is, for example, a printer, network, personal computer, keyboard, and pointing device. A monitor device (not shown) is connected to the connector 1003 through a monitor cable (not shown).

The transmitting unit 1004 transmits excitation signals for exciting ultrasound transducing elements 202a. The transmitting unit 1004 can transmit excitation signals for the respective ultrasound transducing elements 202a in parallel. The receiving unit 1005 receives the signals output from the ultrasound transducing elements 202a. The receiving unit 1005 can receive the signals output from the ultrasound transducing elements 202a in parallel. The receiving unit 1005 outputs the received signals.

The measuring unit 1006 performs predetermined measurement processing on the basis of the reception signals output from the receiving unit 1005. The measuring unit 1006 outputs the measurement information obtained by the above measurement processing to the storage medium 1007, interface unit 1008, display processing unit 1009, and control unit 1011 under the control of the control unit 1011. The storage medium 1007 is, for example, a semiconductor memory. The storage medium 1007 stores various kinds of information such as the above measurement information. The interface unit 1008 performs communication processing conforming to, for example, the USB standard to realize communication with the external device connected to the connector 1002. The display processing unit 1009 generates an image signal for causing the monitor device connected to the connector 1003 to display an image on the basis of the above measurement information, information supplied from the control unit 1011, and the like.

The image simulation processing unit 1010 comprises, for example, a microprocessor. The image simulation processing unit 1010 generates a simulation image by image simulation simulating an ultrasound diagnostic apparatus using a virtual ultrasound probe or ideal ultrasound probe which is constructed by the control unit 1011.

The control unit 1011 comprises, for example, a microprocessor. The control unit 1011 systematically controls the respective units of the main unit 1000 to realize operation for the diagnosis of the ultrasound probe 200. The control unit 1011 also has a function of obtaining the feature value of a reflected ultrasound signal on the basis of the measurement result obtained by the measuring unit 1006. The control unit 1011 has a function of constructing a virtual ultrasound probe on the basis of the above feature amount. The control unit 1011 has a function of generating report data indicating a report with which the simulation image generated by the image simulation processing unit 1010 is combined.

The medical diagnosing unit 1012 also includes an imaging control unit 1012a, image generating unit 1012b, memory unit 1012c, and display unit 1012d. The imaging control unit 1012a controls the transmitting unit 1004, receiving unit 1005, and image generating unit 1012*b* so as to perform proper imaging processing in accordance with diagnosis contents or the like. The image generating unit 1012*b* generates display data for displaying an image for medical diagnosis on the basis of the signals output from the receiving unit 1005. The image represented by display data includes, for example, a reconstructed image such as a tomographic image or three-dimensional image concerning an organ or blood flow in a subject to be examined or a text image or graph representing a measurement value such as a blood flow rate or its change. The memory unit 1012*c* stores the above display data. The display unit 1012*d* performs display operation based on the display data.

The operation of the ultrasound diagnostic apparatus having the above arrangement will be described next.

When medical diagnosis on a subject to be examined is to be performed by using the ultrasound probe 200, information useful for medical diagnosis can be presented by activating the medical diagnosing unit 1012 in the same manner as a known ultrasound diagnostic apparatus.

In diagnosing the ultrasound probe 200, a maintenance operator places a test object in a medium such as water in a vessel such as a water bath and also makes the head unit 202 face the test object in advance, as shown in FIG. 41.

Figure 42A:
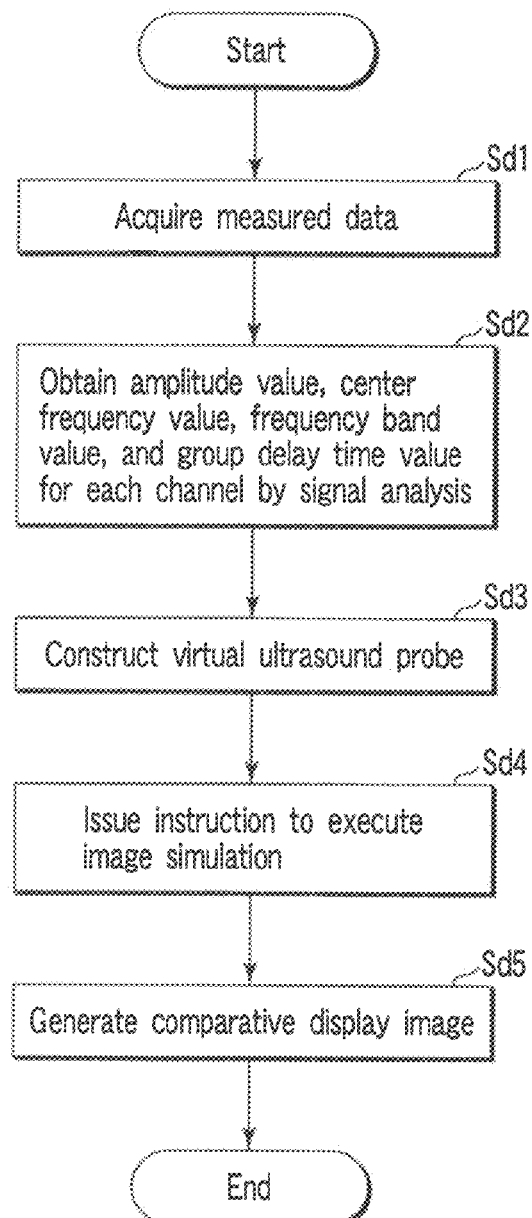
FIGS. 42A, 42B are flowcharts showing a processing sequence executed by a control unit for diagnosing an ultrasound probe in FIG. 41.
Figure 42B:
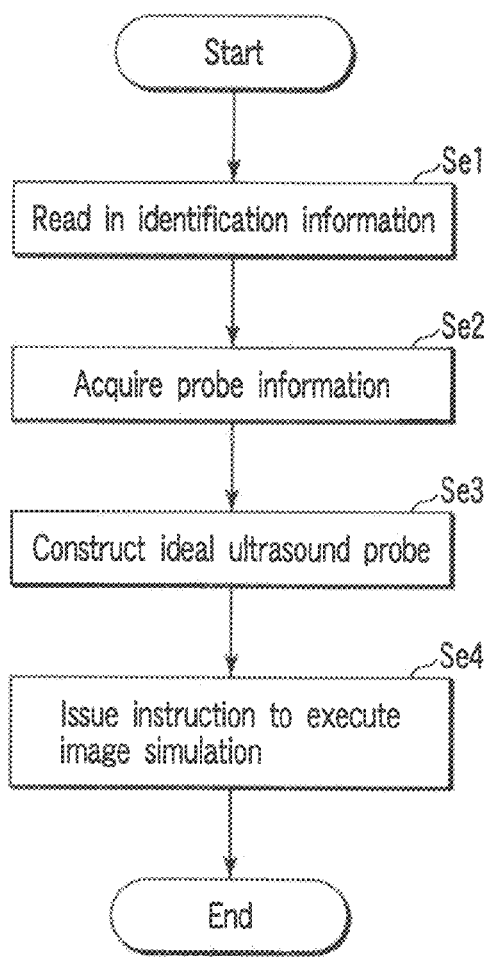

If it is required to diagnose the ultrasound probe 200 connected to the connector 1001, the control unit 1011 executes the processing shown in FIG. 42A and the processing shown in FIG. 42B.

In step Sd1 in FIG. 42A, the control unit 1011 causes the respective units to acquire measured data. More specifically, the control unit 1011 causes the transmitting unit 1004 to excite the ultrasound transducing elements 202*a*. The 1011 also causes the receiving unit 1005 to receive reflected ultrasound signals from the test object through the ultrasound transducing elements 202*a*, signal lines 203*a*, contacts 201*a*, and contacts 1001*a*. The control unit 1011 further causes the measuring unit 1006 to collect various kinds of data concerning the reflected ultrasound signals. The measuring unit 1006 stores the collected data in the storage medium 1007. This measured data acquisition is performed for each channel.

In step Sd2, the control unit 1011 performs signal analysis. That is, the control unit 1011 analyzes the reflected ultrasound signals on the basis of the measured data stored in the storage medium 1007, and obtains the feature values of the reflected ultrasound signals for each channel. As feature values, amplitude values, center frequency values, frequency band values, group delay time values, and the like are conceivable. In this embodiment, these amplitudes, center frequencies, frequency bands, and group delays are obtained. In step Sd3, the control unit 1011 stores amplitude data, center frequency data, frequency band data, and group delay data representing the respective values obtained in the above manner in the storage medium 1007.

In step Sd4, the control unit 1011 instructs the image simulation processing unit 1010 to construct a virtual ultrasound probe. Upon receiving this instruction, the image simulation processing unit 1010 constructs a virtual ultrasound probe on the basis of the amplitude values, center frequency values, frequency band values, and group delay time values calculated in the above manner. In step Sd5, the control unit 1011 issues an instruction to execute image simulation using the constructed virtual ultrasound probe. Upon receiving this instruction, the image simulation processing unit 1010 executes image simulation simulating an ultrasound diagnostic apparatus using the above ultrasound probe. A known technique can be applied to this image simulation. For example, in image simulation based on a point spread function (PSF), transmission/reception characteristic parameters of a lattice array may be obtained by using the above feature values. The image simulation processing unit 1010 stores an image obtained as a result of such image simulation as a check probe image in the storage medium 1007.

In step Se1 in FIG. 42B, the control unit 1011 reads in the identification information output from an identification information output unit 204. In step Se2, the control unit 1011 acquires probe information concerning the model of the ultrasound probe 200 connected to the connector 1001. The model of the ultrasound probe 200 is determined on the basis of the above identification information. The identification information is information for specifying each ultrasound probe 200, and does not generally include information indicating a model. The control unit 1011 determines the model of the ultrasound probe 200 by referring to a database in which pieces of model information are written in correspondence with various kinds of identification information. The database may be acquired in advance from the external device connected to the connector 1002 or stored in advance in the storage medium 1007. Alternatively, information indicating a model may be contained in identification information, and the control unit 1011 may directly determine the model of the ultrasound probe 200 from this information. Probe information is information containing the ideal value of the above feature value concerning each model. The control unit 1011 acquires probe information from the above database or another database. Note that when only the single model of the ultrasound probe 200 is to be diagnosed, such processing can be omitted.

In step Se3, the control unit 1011 constructs an ideal ultrasound probe on the basis of the feature values indicated by the above acquired probe information. In step Se4, the control unit 1011 issues an instruction to execute image simulation using the constructed ideal ultrasound probe. Upon receiving this instruction, the image simulation processing unit 1010 executes image simulation simulating an ultrasound diagnostic apparatus using the above ideal ultrasound probe. The image simulation processing unit 1010 stores an image obtained as a result of such image simulation as a reference probe image in the storage medium 1007.

In step Sd5 in FIG. 42A, the control unit 1011 reads out a check probe image and reference probe image from the storage medium 1007, and generates a comparative display image presenting these images side by side. FIG. 43 is a view showing an example of this comparative display image. A signal for causing the monitor device to display the comparative display image is generated by the display processing unit 1009 under the control of the control unit 1011, and is output from the connector 1003.

The control unit 1011 can generate the print data of a report like that shown in FIG. 34 which contains the comparative display image. This print data is sent to a printer through the interface unit 1008 and connector 1002 and printed.

As described above, according to the 11th embodiment, a check probe image can be presented, which is obtained by image simulation using a virtual ultrasound probe constructed while reflecting the state of the ultrasound probe 200 which is determined from the reception states of reflected ultrasound signals from a test object. The maintenance operator can easily and properly recognize the degree of influence of a deterioration in the ultrasound probe 200 on image diagnosis on the basis of this check probe image.

According to the 11th embodiment, the reference probe image obtained by image simulation using the ideal ultrasound probe having ideal characteristics is presented together with the above check probe image. This allows the maintenance operator to more easily and properly recognize the degree of influence of a deterioration in the ultrasound probe 200 on image diagnosis by comparing the check probe image with the reference probe image.

In addition, according to the 11th embodiment, a report containing a check probe image can be automatically printed. By using the report printed by this function, the maintenance operator can report to the user of the ultrasound probe 200 the current state of the ultrasound probe 200 so as to make it easy to understand.

The 11th embodiment can be variously modified as follows.

In image simulation, the ultrasound diagnostic apparatus may generate an image such as a B-mode image, M-mode image, or Doppler image. This allows the maintenance operator to more precisely recognize a degree of influence on actual image diagnosis.

As a reference probe image, an image prepared in advance may be used.

An ideal ultrasound probe may be constructed on the basis of the initial characteristics of the ultrasound probe 200 to be examined at the time of shipment or the like, and a reference probe image may be obtained by image simulation using the ideal ultrasound probe. In this case, the characteristics of each ultrasound probe 200 in an initial state, e.g., at the time of shipment, or average characteristics for each lot are registered in a database.

Alternatively, a check probe image obtained in the past may be stored in the storage medium 1007 or registered in an external database, and may be used as a reference probe image.

A reference probe image need not be presented.

A check probe image may be output to an external device to be arbitrarily used for, for example, display operation or the generation of a report.

The transmitting unit 1004 and receiving unit 1005 each may be designed to have a 1-channel arrangement by using a matrix switch with a multiplexer arrangement. This makes it possible to reduce the circuit sizes of the transmitting unit 1004 and receiving unit 1005.

Display operation based on a signal generated by the display processing unit 1009 may be performed by the display unit 1012d. In this case, the display processing unit 1009 is connected to the image generating unit 1012b. The image generating unit 1012b generates display data from the signal generated by the display processing unit 1009. The display data is written in the memory unit 1012c.

This apparatus may be realized as an ultrasound probe diagnosing apparatus by omitting the medical diagnosing unit 1012.

Note that a plurality of functions of the ultrasound probe diagnosing functions described in the respective embodiments described above can be provided for a single ultrasound diagnostic apparatus or ultrasound probe diagnosing apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound probe diagnosing system, comprising:
an ultrasound probe including an array of a plurality of ultrasound transducing elements configured to diagnose the ultrasound probe on the basis of how the ultrasound probe receives reflected ultrasound waves from a test object placed to face the ultrasound probe;
a control microprocessor configured to:
variably set transmission/reception periods in repetitive ultrasound wave transmission/reception for each ultrasound wave transmission/reception, the transmission/reception periods being variably set so that times of the transmission/reception periods are sequentially incremented;
execute, for at least one of the ultrasound transducing elements, a processing of adding reflected ultrasound signals repeatedly output from one of the plurality of ultrasound transducing elements for each of said set transmission/reception periods while leading edges of the reflected ultrasound signals are matched with each other; and
diagnose the ultrasound probe on the basis of at least one of the added reflected ultrasound signals by using the at least one of the added reflected ultrasound signals in a posture determination.

2. An ultrasound diagnostic system, comprising:
an ultrasound probe including an array of a plurality of ultrasound transducing elements and obtains information for ultrasound probe diagnosis on a subject to be examined on the basis of reflected ultrasound waves received from the subject by the ultrasound probe;
a microprocessor configured to:
variably set repetition transmission/reception periods for each ultrasound wave transmission/reception with respect to a test object different from the subject, the transmission/reception periods being variably set so that times of the transmission/reception periods are sequentially incremented;
execute, for at least one of the ultrasound transducing elements, a processing of adding reflected ultrasound signals repeatedly output from one of the plurality of ultrasound transducing elements for each of said set transmission/reception periods while leading edges of the reflected ultrasound signals are matched with each other; and
diagnose the ultrasound probe on the basis of at least one of the added reflected ultrasound signals by using the at least one of the added reflected ultrasound signals in a posture determination.

3. An ultrasound probe diagnosing method of diagnosing an ultrasound probe including an array of a plurality of ultrasound transducing elements on the basis of how the ultrasound probe receives reflected ultrasound waves from a test object placed to face the ultrasound probe, comprising:
variably setting transmission/reception periods in repetitive ultrasound wave transmission/reception for each ultrasound wave transmission/reception, the transmission/reception periods being variably set so that times of the transmission/reception periods are sequentially incremented;
executing, for at least one of the ultrasound transducing elements, a processing of adding reflected ultrasound signals output repeatedly output from one of the plurality of ultrasound transducing elements for each of said set transmission/reception periods while leading edges of the reflected ultrasound signals are matched with each other; and
diagnosing the ultrasound probe on the basis of at least one of the added reflected ultrasound signals by using the at least one of the added reflected ultrasound signals in a posture determination.

* * * * *